(12) United States Patent
Sinha et al.

(10) Patent No.: US 12,070,449 B2
(45) Date of Patent: *Aug. 27, 2024

(54) METHODS OF TREATING TTR AMYLOIDOSIS USING AG10

(71) Applicant: EIDOS THERAPEUTICS, INC., San Francisco, CA (US)

(72) Inventors: Uma Sinha, San Francisco, CA (US); Satish Rao, San Francisco, CA (US)

(73) Assignee: EIDOS THERAPEUTICS, INC., Palo Alto, CA (US)

( * ) Notice: Subject to any disclaimer, the term of this patent is extended or adjusted under 35 U.S.C. 154(b) by 31 days.

This patent is subject to a terminal disclaimer.

(21) Appl. No.: 17/332,359

(22) Filed: May 27, 2021

(65) Prior Publication Data
US 2022/0016081 A1  Jan. 20, 2022

Related U.S. Application Data

(63) Continuation of application No. 16/361,587, filed on Mar. 22, 2019, now Pat. No. 11,058,668.

(60) Provisional application No. 62/810,651, filed on Feb. 26, 2019, provisional application No. 62/758,235, filed on Nov. 9, 2018, provisional application No. 62/731,629, filed on Sep. 14, 2018, provisional application No. 62/765,096, filed on Aug. 17, 2018, provisional application No. 62/647,411, filed on Mar. 23, 2018.

(51) Int. Cl.
*A61K 31/415* (2006.01)

(52) U.S. Cl.
CPC .................. *A61K 31/415* (2013.01)

(58) Field of Classification Search
CPC .................................... A61K 31/415
See application file for complete search history.

(56) References Cited

U.S. PATENT DOCUMENTS

| | | |
|---|---|---|
| RE28,819 E | 5/1976 | Thompson |
| 4,117,149 A | 9/1978 | Bass |
| 4,232,161 A | 11/1980 | Diana et al. |
| 4,234,725 A | 11/1980 | Diana et al. |
| 4,255,329 A | 3/1981 | Ullman |
| 4,261,928 A | 4/1981 | Diana et al. |
| 4,328,245 A | 5/1982 | Yu et al. |
| 4,358,603 A | 11/1982 | Yu |
| 4,409,239 A | 10/1983 | Yu |
| 4,410,545 A | 10/1983 | Yu et al. |
| 4,522,811 A | 6/1985 | Eppstein et al. |
| 4,657,914 A | 4/1987 | Bernardi et al. |
| 4,668,640 A | 5/1987 | Wang et al. |
| 4,764,521 A | 8/1988 | Herron |
| 5,315,015 A | 5/1994 | Hui et al. |
| 5,521,202 A | 5/1996 | Yano et al. |
| 5,709,874 A | 1/1998 | Hanson et al. |
| 5,759,542 A | 6/1998 | Gurewich |
| 5,840,674 A | 11/1998 | Yatvin et al. |
| 5,860,957 A | 1/1999 | Jacobsen et al. |
| 5,900,252 A | 5/1999 | Calanchi et al. |
| 5,948,433 A | 9/1999 | Burton et al. |
| 5,972,366 A | 10/1999 | Haynes et al. |
| 5,983,134 A | 11/1999 | Ostrow |
| 5,985,307 A | 11/1999 | Hanson et al. |
| 5,985,317 A | 11/1999 | Venkateshwaran et al. |
| 6,004,534 A | 12/1999 | Langer et al. |
| 6,010,715 A | 1/2000 | Wick et al. |
| 6,024,975 A | 2/2000 | D et al. |
| 6,039,975 A | 3/2000 | Shah et al. |
| 6,048,736 A | 4/2000 | Kosak |
| 6,060,082 A | 5/2000 | Chen et al. |
| 6,071,495 A | 6/2000 | Unger et al. |
| 6,120,751 A | 9/2000 | Unger |
| 6,131,570 A | 10/2000 | Schuster et al. |
| 6,139,865 A | 10/2000 | Friend et al. |
| 6,167,301 A | 12/2000 | Flower et al. |
| 6,253,872 B1 | 7/2001 | Neumann |
| 6,256,533 B1 | 7/2001 | Yuzhakov et al. |
| 6,261,595 B1 | 7/2001 | Stanley et al. |
| 6,267,983 B1 | 7/2001 | Fujii et al. |
| 6,271,359 B1 | 8/2001 | Norris et al. |
| 6,274,552 B1 | 8/2001 | Tamarkin et al. |
| 6,316,652 B1 | 11/2001 | Steliou |
| 7,763,747 B2 | 7/2010 | Snow et al. |
| 8,143,424 B2 | 3/2012 | Chhipa et al. |
| 8,168,775 B2 * | 5/2012 | Sah .................. C07H 21/04  435/325 |
| 8,226,977 B2 | 7/2012 | Kolatkar et al. |

(Continued)

FOREIGN PATENT DOCUMENTS

| | | |
|---|---|---|
| DE | 2834322 A1 | 2/1979 |
| WO | 1995012815 | 5/1995 |

(Continued)

OTHER PUBLICATIONS

International Search Report corresponding to PCT/US2018/000025 mailed Jun. 15, 2018; 14 pages.
International Search Report and Written Opinion for PCT/US2019/023555, Jun. 6, 2019, 9 pages.
International Search Report and Written Opinion for PCT/US2019/046789, Oct. 21, 2019; 11 pages.
Partial Supplementary European Search Report corresponding to EP 18 75 3963 completed Oct. 29, 2020; 4 pages.
Extended European Search Report corresponding to EP 18 75 3963 completed Oct. 29, 2020, with Search Opinion mailed Feb. 10, 2021; 10 pages.
Adamski-Werner, et al., Diflunisal Analogues Stabilize the Native State of Transthyretin. Potent Inhibition of Amyloidogenesis, J Med Chem , 2004 , pp. 355-374, vol. 47, No. 2.

(Continued)

*Primary Examiner* — Svetlana M Ivanova
(74) *Attorney, Agent, or Firm* — Mintz Levin Cohn Ferris Glovsky and Popeo PC

(57) ABSTRACT

Described herein are methods for treating transthyretin (TTR) amyloidosis in a subject. The methods include specific dosing regimens that have great efficacy in treating the subjects and that are well tolerated in subjects

20 Claims, 43 Drawing Sheets

Specification includes a Sequence Listing.

(56) References Cited

U.S. PATENT DOCUMENTS

| | | |
|---|---|---|
| 8,378,118 B2 | 2/2013 | Chhipa et al. |
| 8,552,034 B2 | 10/2013 | Verwijs et al. |
| 8,642,660 B2 | 2/2014 | Goldfarb |
| 8,877,795 B2 | 11/2014 | Graef et al. |
| 9,169,214 B2 | 10/2015 | Graef et al. |
| 9,308,209 B2 | 4/2016 | Graef et al. |
| 9,642,838 B2 | 5/2017 | Graef et al. |
| 9,913,826 B2 | 3/2018 | Graef et al. |
| 10,039,726 B2 | 8/2018 | Graef et al. |
| 10,278,929 B2 | 5/2019 | Graef et al. |
| 10,398,681 B2 | 9/2019 | Graef et al. |
| 10,513,497 B2 | 12/2019 | Chand et al. |
| 10,842,777 B2 | 3/2020 | Graef et al. |
| 11,058,668 B2 * | 7/2021 | Sinha ............... A61K 31/64 |
| 11,078,162 B2 | 8/2021 | Chand et al. |
| 11,260,047 B2 | 3/2022 | Jernelius et al. |
| 2002/0048610 A1 | 4/2002 | Cima et al. |
| 2006/0160796 A1 | 7/2006 | Pfahl et al. |
| 2006/0183792 A1 | 8/2006 | Fobare et al. |
| 2007/0043096 A1 | 2/2007 | Tidmarsh et al. |
| 2008/0319077 A1 | 12/2008 | Suzuki et al. |
| 2009/0247547 A1 | 10/2009 | Shultz et al. |
| 2010/0183513 A1 | 7/2010 | Froestl et al. |
| 2010/0249094 A1 | 9/2010 | Yeung et al. |
| 2013/0095181 A1 | 4/2013 | Verwijs et al. |
| 2014/0179751 A1 * | 6/2014 | Graef ............... A61P 27/02 |
| | | 436/501 |
| 2017/0000807 A1 | 1/2017 | Koziara et al. |
| 2017/0029390 A1 | 2/2017 | Butler et al. |
| 2018/0125789 A1 | 5/2018 | Dalziel et al. |
| 2020/0016098 A1 | 1/2020 | Graef et al. |
| 2020/0054607 A1 | 2/2020 | Jernelius et al. |
| 2021/0260034 A1 | 8/2021 | Graef et al. |
| 2022/0041558 A1 | 2/2022 | Chand et al. |
| 2022/0313661 A1 | 10/2022 | Jernelius et al. |
| 2023/0105307 A1 | 4/2023 | Graef et al. |
| 2023/0390246 A1 | 12/2023 | Graef et al. |

FOREIGN PATENT DOCUMENTS

| | | |
|---|---|---|
| WO | 2004096808 A1 | 11/2004 |
| WO | 2006009826 A1 | 1/2006 |
| WO | 2008077597 A1 | 7/2008 |
| WO | 2008141020 A1 | 11/2008 |
| WO | 2008145616 A1 | 12/2008 |
| WO | 2008154241 A1 | 12/2008 |
| WO | 2010010190 A1 | 1/2010 |
| WO | 2010030592 A1 | 3/2010 |
| WO | 2010059658 A1 | 5/2010 |
| WO | 2011046771 A1 | 4/2011 |
| WO | 2011053948 A1 | 5/2011 |
| WO | 2011140333 A1 | 11/2011 |
| WO | 2012082566 A1 | 6/2012 |
| WO | 2016025129 A1 | 2/2016 |
| WO | 2018/071678 A1 | 4/2018 |

OTHER PUBLICATIONS

Aldred, The cerebral expression of plasma protein genes in different species, Comp Biochem Physiol B Biochem Mol Biol., 1995, pp. 1-15, vol. 1, No. 1.

Alhamadsheh, et al., Potent Kinetic Stabilizers that Prevent Transthyretin-Mediated Cardiomyocyte Proteotoxicity, Sci. Transl. Med., 2011, pp. 1-9, vol. 3, No. 97.

Arkin, et al., Small-molecule inhibitors of protein—protein interactions: progressing towards the dream, Nat Rev Drug Disco., 2004, pp. 301-317, vol. 3, No. 4.

Bartalena, et al., Thyroid hormone transport proteins, Clin Lab Med, 1993, pp. 583-598, vol. 13, No. 3.

Baures, STN International HCAPLUS database, (Columbus, Ohio), Accession No. 1998:617889, 1998.

Blake, et al., Structure of prealbumin: Secondary, tertiary and quaternary interactions determined by Fourier refinement at 1.8 A, J Mol Biol, 1978, pp. 339-356, vol. 121, No. 3.

Buxbaum, et al., Significance of the Amyloidogenic Transthyretin Val 122 ile allele in African Americans in the Arteriosclerosis Risk in Communities (ARIC) and Cardiovascular Health (CHS) Studies, Am Heart J, 2010, pp. 864-870, vol. 159.

Buxbaum, et al., Transthyretin protects Alzheimer's mice from the behavioral and biochemical effects of A. toxicity, Proc Natl Acad Sci., 2008, pp. 2681-2686, vol. 105, No. 7.

Caira, Mino R., "Crystalline Polymorphism of Organic Compounds," Topics in Current Chemistry (Jan. 1, 1998) 198:163-208.

Chang, et al., Evolution of thyroid hormone binding by transthyretins in birds and mammals, Eur J Biochem., 1999, pp. 534-542, vol. 259.

Choi, et al., "Accelerated AB Deposition in APPswe/PS1 delta E9 Mice with Hemizygous Deletions of TTR (Transthyretin)", J Neurosci, 2007, pp. 7006-7010, 27(26).

Choi, et al., Antidiabetic actions of a non-agonist PPARy ligand blocking Cdk5-mediated phosphorylation, Nature, 2011, pp. 477-481.

Coelho, Familial amyloid polyneuropathy: new developments in genetics and treatment, Current opinion in neurology, 1996, pp. 355-359, vol. 9, No. 5.

Connelly, et al., Structure-based design of kinetic stabilizers that ameliorate the transthyretin amyloidosis, Current Opinion in Structural Biology, 2010, pp. 54-62, vol. 20, No. 1.

Connors, et al., Cardiac amyloidosis in African Americans: Comparison of clinical and laboratory features of transthyretin V122I amyloidosis and immunoglobulin light chain amyloidosis, Am Heart J, 2009, pp. 607-614, vol. 158, No. 4.

Diana, et al., Synthesis and antiherpetic activity of some 4-[(aryloxy)alkyl]pyrazoles, Journal of Medicinal Chemistry, 1981, pp. 731-735, vol. 24, No. 6.

Emerson, et al., NMR characterization of interleukin-2 in complexes with the IL-2Ralpha receptor component, and with low molecular weight compounds that inhibit the IL-2/IL-Ralpha interaction, Protein Sci., 2003, pp. 811-822, vol. 12, No. 4.

Falk, et al., The Systemic Amyloidoses, N. Eng. J. Med., 1997, pp. 898-909, vol. 337.

Farr, et al., STN International HCAPLUS database, Accession No. 2001:338762, 2007.

Fujiwara, Mitsuko et al., "First-principles and direct design approaches for the control of pharmaceutical crystallization," Journal of Process Control (Aug. 1, 2005) 15(5):493-504.

Gell, et al. The Detection and Quantitation of Protein Oligomerization, Adv Exp Med Biol., 2012, pp. 19-41, vol. 747.

Haigis, et al., The Aging Stress Response, Mol Cell, 2010, pp. 333-344, vol. 40, No. 2.

He, et al., Small-molecule inhibition of TNF-alpha, Science, 2005, pp. 1022-1025, vol. 310, No. 5750.

Hull, et al., Islet amyloid: a critical entity in the pathogenesis of type 2 diabetes, J. Clin. Endocrinol & Metab, 2004, pp. 3629-3643, vol. 89, No. 8.

Jacobson, et al., Variant-Sequence Transthyretin (Isoleucine 122) in Late-Onset Cardiac Amyloidosis in Black Americans, N Engl J Med, 1997, pp. 466-473, vol. 336.

Jiang, et al., The V122I cardiomyopathy variant of transthyretin increases the velocity of rate-limiting tetramer dissociation, resulting in accelerated amyloidosis, Proc Natl Acad Sci USA, 2001, pp. 14943-14948, vol. 98, No. 26.

Joao, et al., Transthyretin mutations in health and disease, Hum Mutat, 1995, pp. 191-196, vol. 5.

Johnson, et al., Native State Kinetic Stabilization as a Strategy To Ameliorate Protein Misfolding Diseases: A on the Transthyretin Amyloidoses, Ace Chem Res, 2005, pp. 911-921, vol. 38, No. 12.

Katritzky, et al., Mannich reactions of carbonyl compounds and enamines with benzotriazole as the NH component, Journal of Heterocyclic Chemistry, 1994, pp. 917-923, vol. 31, No. 4.

Koehler, et al., Discovery of an inhibitor of a transcription factor using small molecule microarrays and diversity-oriented synthesis, J Am Chem Soc, 2003, pp. 8420-8421, vol. 125, No. 28.

Maher, et al., Synthesis of some new 3-(2'-heterocyclicethyl)-2-methyl-3,4-dihydroquinazolin-4-one derivatives as antimicrobial agents, J Chem Tech & Biotech, 1992, pp. 209-215, vol. 55, No. 3.

(56) References Cited

OTHER PUBLICATIONS

Miller, et al., Enthalpy-Driven Stabilization of Transthyretin by AG10 Mimics a Naturally Occurring Genetic Variant That Protects from Transthyretin Amyloidosis, Journal of Medicinal Chemistry, Aug. 22, 2018, pp. 7862-7876, vol. 61, No. 17.

Miyawaki, Development of Probes for Cellular Functions Using Fluorescent Proteins and Fluorescence Resonance Energy Transfer, Annu Rev Biochem., 2011, pp. 357-373, vol. 7, No. 80.

Monaco, et al., Structure of a complex of two plasma proteins: transthyretin and retinol-binding protein, Science, 1995, pp. 1039-1047, vol. 268, No. 5231.

Morissette, Sherry L. et al., "High-throughput crystallization: polymorphs, salts, co-crystals and solvates of pharmaceutical solids," *Advanced Drug Delivery Reviews* (Feb. 23, 2004) 56(3):275-300.

National Center for Biotechnology Information. PubChem Compound Database; CID=71464713, https://pubchenn.ncbi.nlnn.nih.gov/ compound/71464713 (accessed Jan. 17, 2019).

Ouyang, et al., Syntheses of 4-(2-Hydroperoxy-2,2- diarylethyl)-3,5-dimethylpyrazoles, 4-(2-Hydroxy-2,2-diarylethyl)-3,5-dimethylpyrazoles, and the Related Compounds, Journal of Heterocyclic Chemistry, 1996, pp. 1291-1302, vol. 33, No. 4.

Penchala, et al., A Biomimetic Approach for Enhancing the in Vivo Half-Life of Peptides, Nature Chemical Biology, 2015, vol. 11, No. 10.

Penchala, et al., AG10 inhibits amyloidogenesis and cellular toxicity of the familial amyloid cardiomyopathy-associated V122I transthyretin, Proc Natl Acad Sci USA, Jun. 11, 2013, pp. 9992-9997, vol. 110, No. 24.

Peterson, et al., Inhibiting transthyretin conformational changes that lead to amyloid fibril formation, Proc Natl Acad Sci USA, 1998, pp. 12956-12960, vol. 95, No. 22.

Prapunpoj, et al., Change in structure of the N-terminal region of transthyretin produces change in affinity of transthyretin to T4 and T3, FEBS J, 2006, pp. 4013-4023, vol. 273, No. 17.

Opadry AQ: Film coatings Opadry QX, Colorcon, 2016; pib_opadry QX_v1_04.2018; 6 pages.

Ran, et al., Non-Conjugated Small Molecule FRET for Differentiating Monomers from Higher Molecular Weight Amyloid Beta Species, PLoS ONE, Apr. 2011, pp. 1-6, vol. 6, No. 4.

Reixach, et al., Tissue damage in the amyloidoses: Transthyretin monomers and nonnative oligomers are the major cytotoxic species in tissue culture, PNAS, Mar. 2, 2004, pp. 2817-2822.

Rickert, et al., The Structure of Interleukin-2 Complexed with its Alpha Receptor, Science, 2005, pp. 1477-1480, vol. 308, No. 5727.

Saraiva, et al., Transthyretin mutations in hyperthyroxinemia and amyloid diseases, Hum Mut., 2001, pp. 493-503, vol. 17, No. 6.

Sekijima, et al., Pathogenesis of and Therapeutic Strategies to Ameliorate the Transthyretin Amyloidoses, Curr Pharm Des, 2008, pp. 3219-3230, vol. 14, No. 30.

Selkoe, et al., Cell Biology of protein misfolding: The examples of Alzheimer's and Parkinson's diseases, Nat Cell Biol 6, 2004, pp. 1054-1061.

Selkoe, et al., Folding proteins in fatal ways, Nature, 2003, pp. 900-904, vol. 426.

Stefani, Protein misfolding and aggregation: new examples in medicine and biology of the dark side of the protein world, Biochimica et biophysica acta, 2004, pp. 5-25, vol. 1739.

Suhr, et al., Liver Transplantation for Hereditary Transthyretin Amyloidosis, Transpl, 2000, pp. 263-276, vol. 6, No. 3.

Variankaval, Narayan et al., "From form to function: Crystallization of avctive pharmaceutical ingredients," *Aiche Journal* (published online Jun. 3, 2008) 54(7):1682-1688.

Wiseman, et al., Kinetic Stabilization of an Oligomeric Protein by a Single Ligand Binding Event, Am Chem Soc, 2005, pp. 5540-5551, vol. 127.

Wojtczak, et al., Structures of Human Transthyretin Complexed with Thyrixine at 2.0 A Resolution and 3', 5'-Dinitro-N-aceytyl-L-thyronine at 2,2 A Resolution, Acta Cryst., 1996, pp. 758-765, vol. D52.

Yamauchi, et al., STN International HCAPLUS database, (Columbus, Ohio), Accession No. 2003:155526.

Zefirov, et al., Ring-Opening Reactions of 1, 1-diacetylcyclopropane with Hydrazine and Hydroxylamine Derivatives as the Novel Synthesis of p-X-ethyl Substituted Pyrazoles and Isoxazoles, Tetrahedron, 1982, pp. 1693-1697, vol. 38, No. 11.

Byrn, Stephen et al., "Pharmaceutical Solids: A Strategic Approach to Regulatory Considerations," *Pharmaceutical Research* (1995) 12(7):945-954.

Seppic: "Ceolus™ Microcrystalline Cellulose (MCC) used as compression excipients," retrieved from the internet at URL:<https://www.seppic.com/en/ceolus> (Jan. 27, 2017; retrieved on Aug. 27, 2023); 4 pages.

Kawaguchi, Yoko et al., "Drug and crystal polymorphism," *Seikatsu Kogaku Kenkyu*, vol. 4, No. 2, (2002), pp. 310-317.

Pharmaceuticals and Medical Devices Act, No. 568, 3.3.1. New drug substances, c) Polymorphic forms (May 1, 2001), 46 pages.

Oshima, Hiroshi, Professor, Osaka City University Hospital, Dept. of Engineering Research, 3-3-138 Sugimoto, Sumiyoshi Ward, Osaka City 558-8585, Tel: 06-6605-2700 Fax: 06-6605-2701, E-mail: ooshima@bioa.eng.osaka-cu.ac.jp; "Crystallization of Polymorphs and Pseudo-polymorphs and Its Control," *Pharm Stage*, 2007, 6, 48-53.

Takada, Noriyuki, Researcher, Chugai Pharmaceutical Co., (formerly) Clinical Research Dept., 1-135 Komakado, Gotemba, Shizuoka Prefecture, 412-8513, Tel: 0550-87-6717 Fax: 0550-87-5397 E-mail: takatanry@chugai-pharm.co.jp; "API form screening and selection in drug discovery stage," *Pharm Stage*, 2007, 6, 20-25.

Yamano, Mitsuhisa, "Approach to Crystal Polymorph in Process Research of New Drug," *Journal of Synthetic Organic Chemistry*, 2007, 65, 907-913.

Extended European Search Report corresponding to EP 19770416.6 dated Nov. 10, 2021 (completed Oct. 27, 2021); 9 pages.

Extended European Search Report corresponding to EP 19849948.5 dated Mar. 15, 2022 (completed Mar. 4, 2022); 6 pages.

Castano, Adam et al., "Natural history and therapy of TTR-cardiac amyloidosis: emerging disease-modifying therapies from organ transplantation to stabilizer and silencer drugs," *Heart Fail Rev* (2015; published online: Nov. 19, 2014) 20:163-178.

Dinunzio, James C. et al., "Use of highly compressible Celous™ microcrystalline cellulose for improved dosage form proeprties containing a hydrophilic solid dispersion," *Drug Development and Industrial Pharmacy* (2012; Published online Jul. 21, 2011) 38(2):180-189.

Kucera, Sandra U. et al., "Evaluation of Ceolus™ microcrystalline cellulose grades for the direct compression of enteric-coated pellets," *Drug Development and Industrial Pharmacy* (2012; Published online Aug. 26, 2011) 38(3):341-350.

Obae, Kasuiro, Ph.D., "Improving of compatibility and friability in high dose tablets living novel microcrystalline cellulose Ceolus™ KG-1000," *Asahi Kasei Chemical Corporation* (Apr. 16, 2008); 43 pages.

Serajuddin, Abu T.M., "Salt formation to improve drug solubility," *Advanced Drug Delivery Reviews* (May 29, 2007) 59:603-616.

Shukla, J.S. et al. "Studies on Neuropharmacological and Biochemical Properties of 5-Substituted Tetrazoles," Ind. J. Physiol. Pharmac. (Oct.-Dec. 1981; rec'd Oct. 8, 1980), 25(4):369-373.

\* cited by examiner

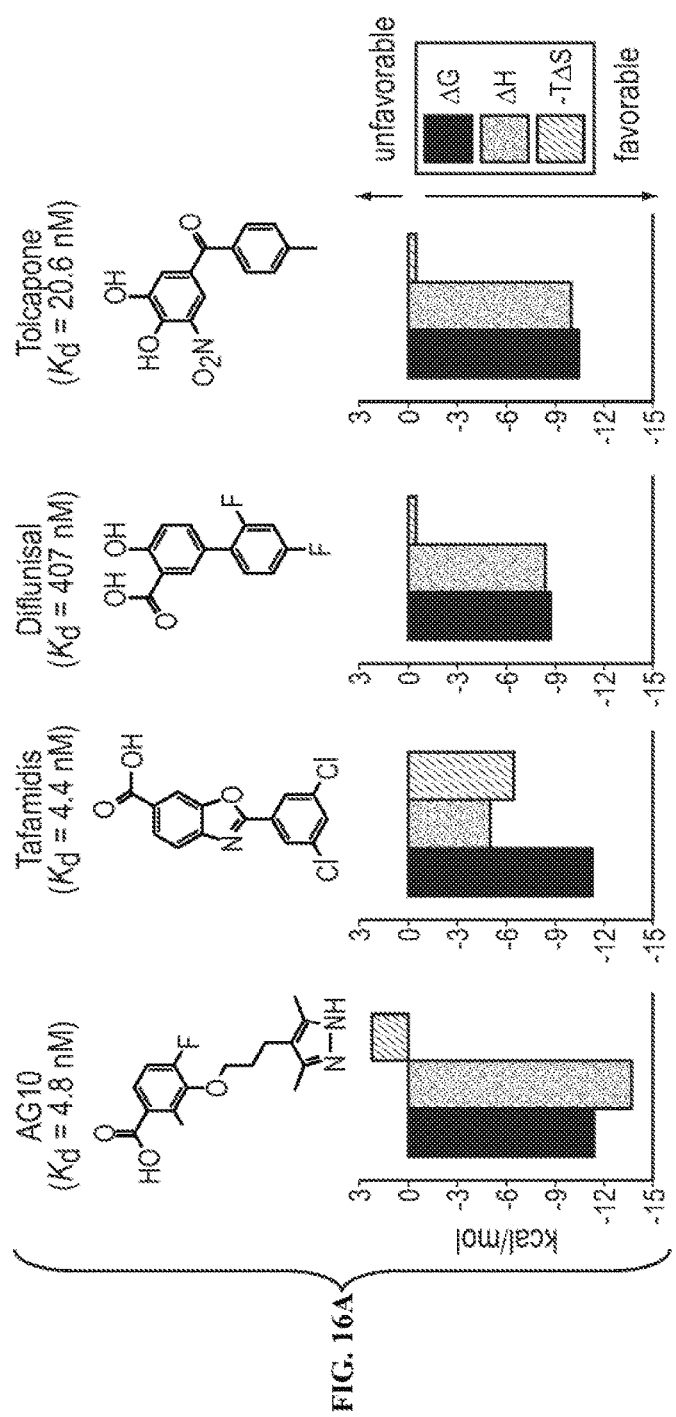
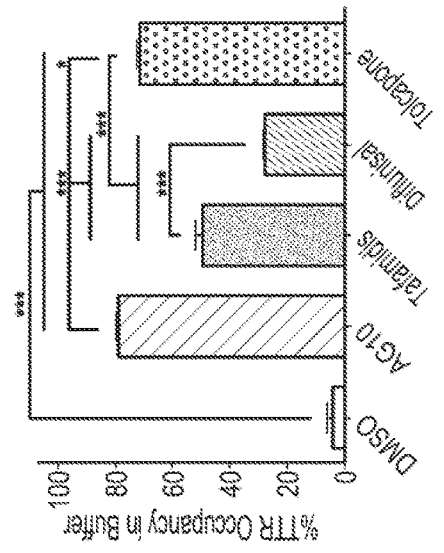
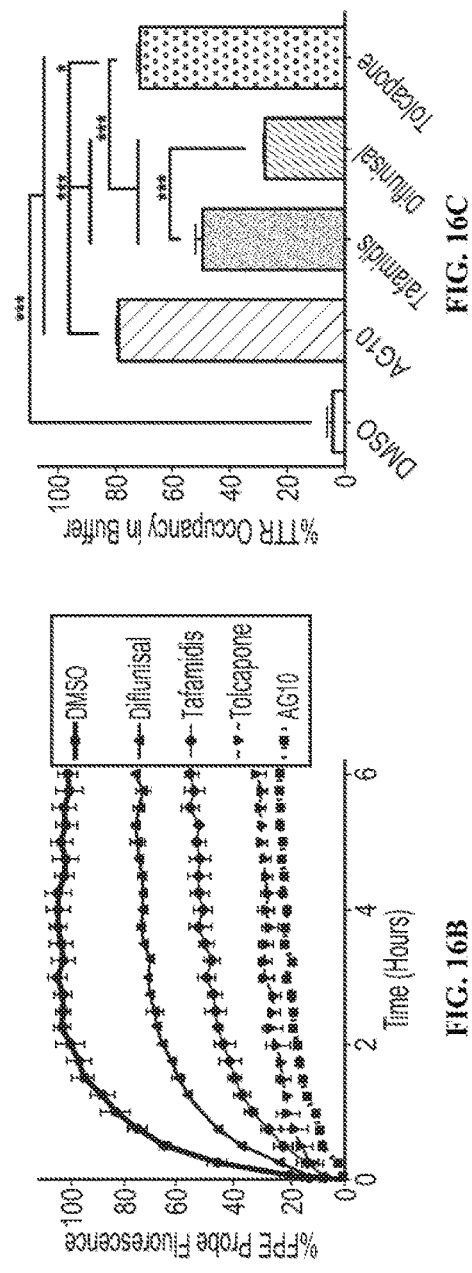
FIG. 16A
FIG. 16B
FIG. 16C

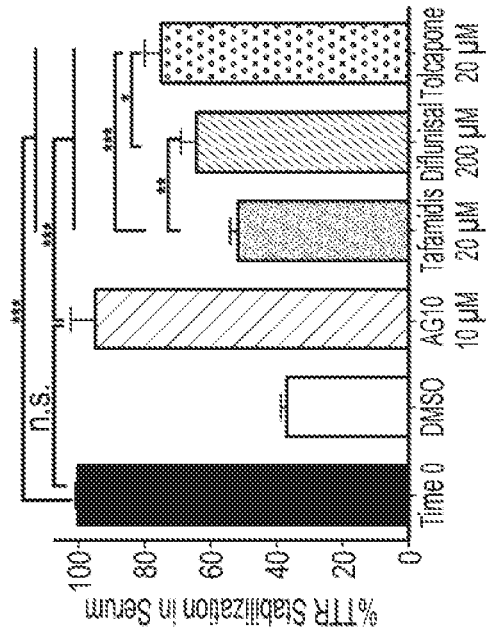
FIG. 17A
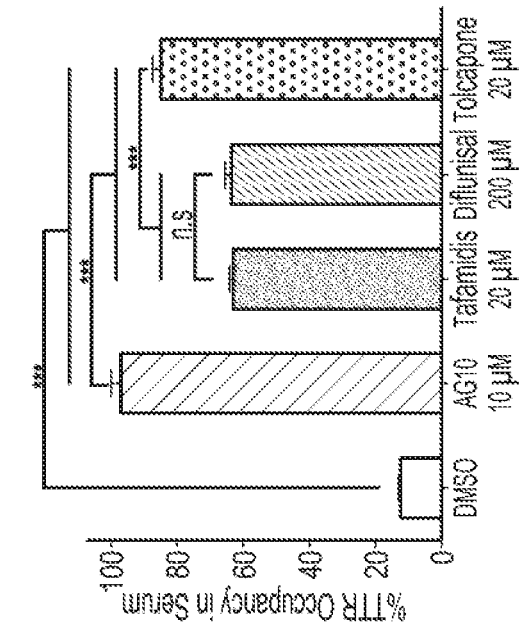
FIG. 17B
FIG. 17C
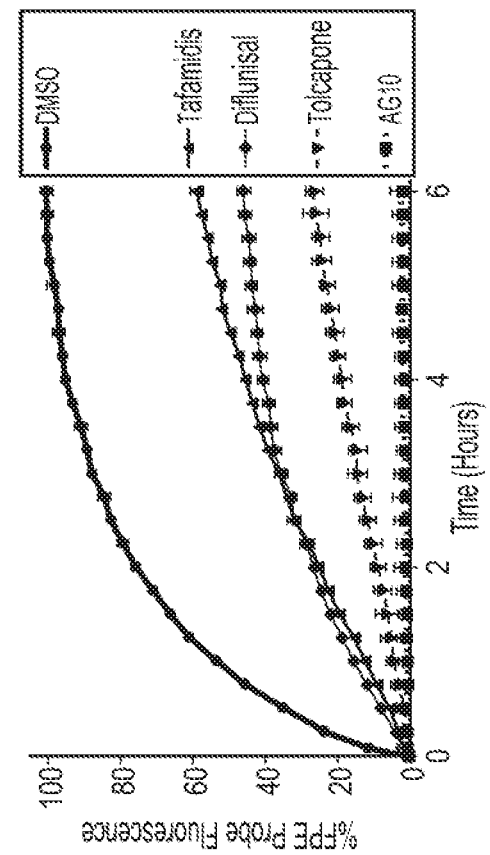
FIG. 17D

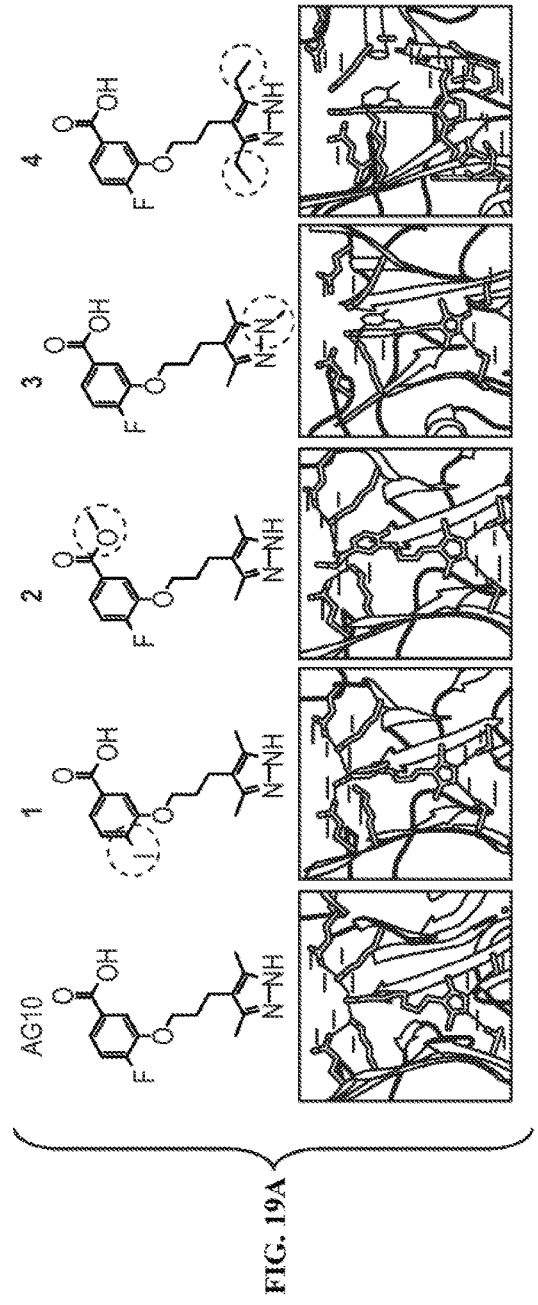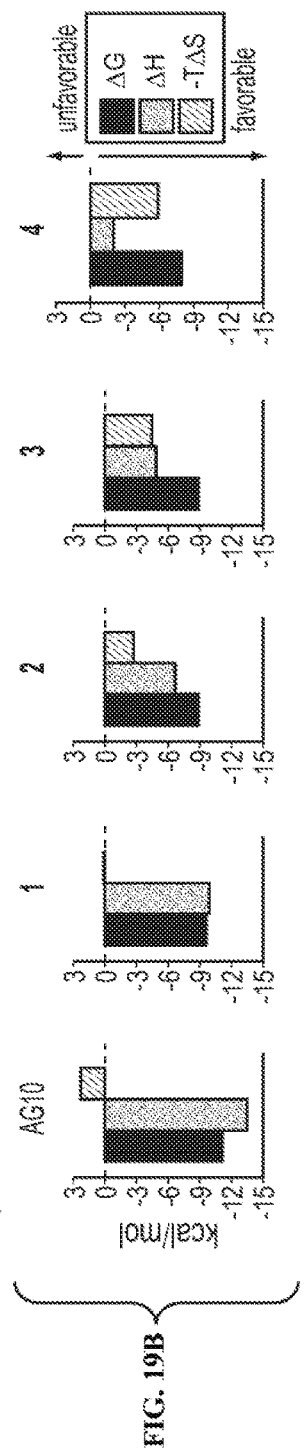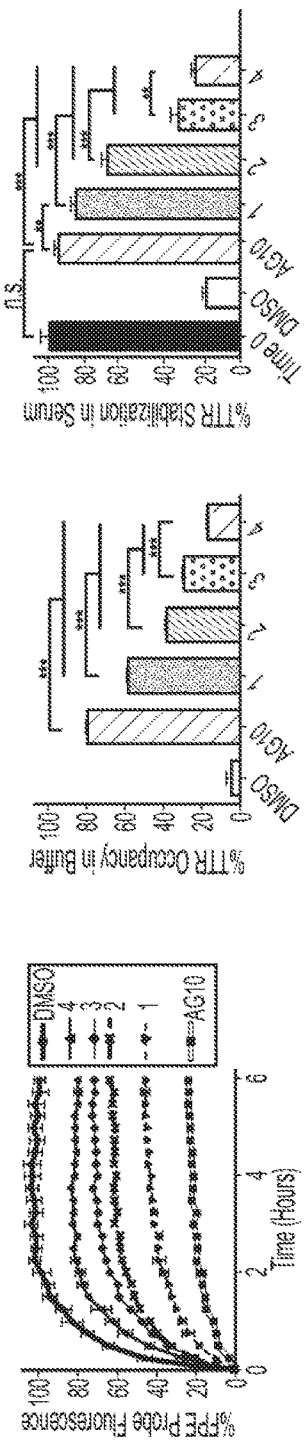
FIG. 19A
FIG. 19B
FIG. 19C
FIG. 19D
FIG. 19E

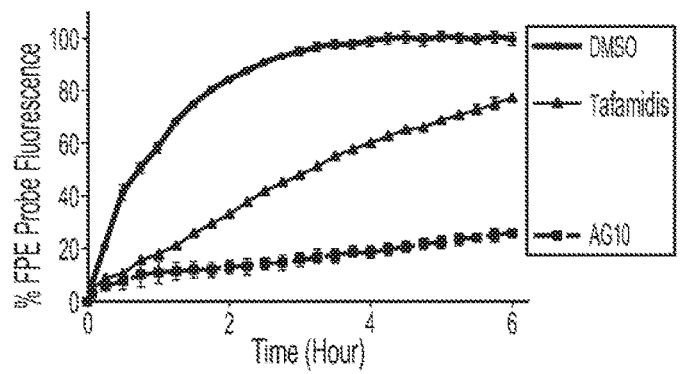 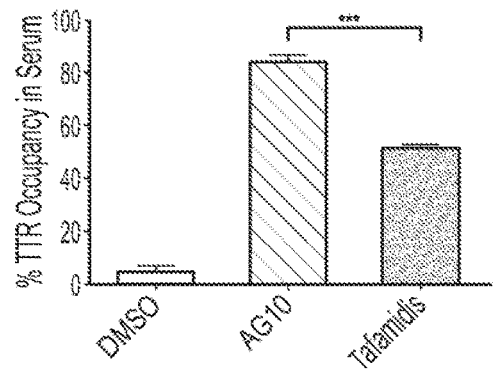
FIG. 21A  FIG. 21B
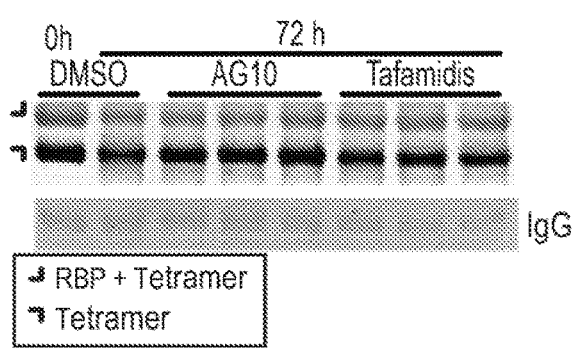 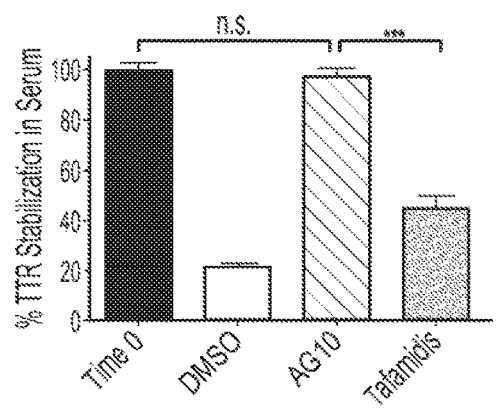
FIG. 21C  FIG. 21D

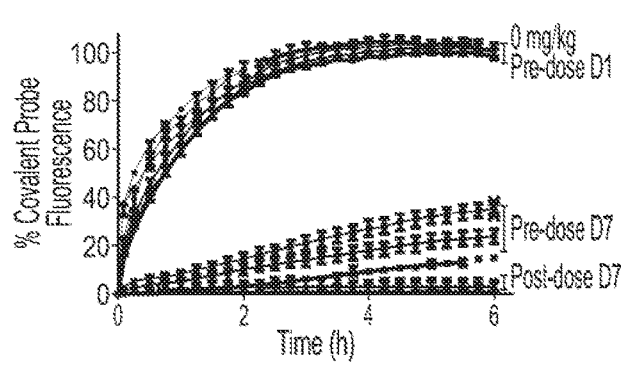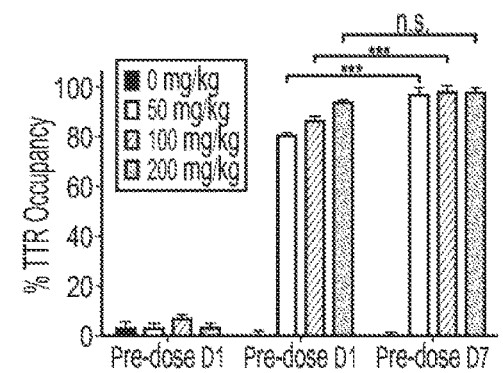
FIG. 22A  FIG. 22B
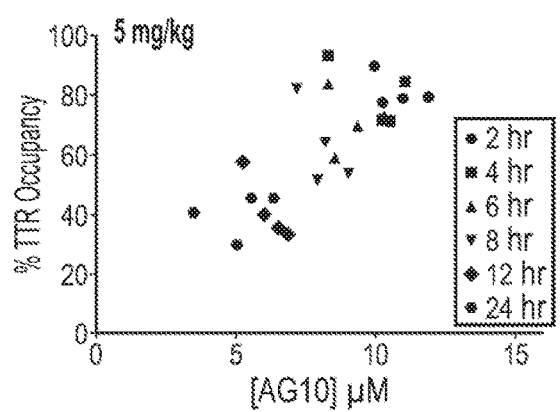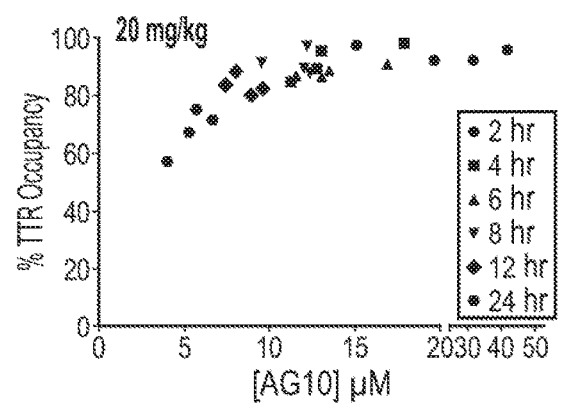
FIG. 22C  FIG. 22D

METHODS OF TREATING TTR AMYLOIDOSIS USING AG10

CROSS-REFERENCES TO RELATED APPLICATIONS

This application is a continuation of U.S. patent application Ser. No. 16/361,587 filed Mar. 22, 2019, which application claims the benefit of priority under 35 U.S.C § 119(e) to U.S. Provisional Application Ser. No. 62/647,411 filed Mar. 23, 2018; 62/765,096 filed Aug. 17, 2018; 62/731,629 filed Sep. 14, 2018; 62/758,235 filed Nov. 9, 2018; and 62/810,651 filed Feb. 26, 2019, the disclosures of each are incorporated herein by reference in their entirety.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

This application hereby incorporates by reference, in its entirety, the sequence listing submitted in computer readable form with this application. The submitted file is entitled: "Sequence Listing—051418-505."

BACKGROUND OF THE INVENTION

Aberrant protein interaction and aggregation, either through protein misfolding or over activation of a signaling pathway is the underlying cause of a large number of human degenerative diseases. As such, targeting protein protein interactions (PPIs) is of therapeutic interest.

One such example of aberrant protein aggregation is the soluble protein transthyretin (TTR or prealbumin). TTR is a 55 kDa homotetrameric protein present in blood and cerebrospinal fluid. When dissociated from its homotetrameric form, TTR dimers can misfold into amyloidogenic monomers. This has been observed with the wild type TTR as well as more than 100 different mutated variants. Research has shown that stabilizing the tetrameric form of TTR inhibits the misfolding of amyloidogenic monomers and subsequent TTR amyloid formation and deposition.

A benzoxazole derivative called tafamidis (2-(3,5-dichlorophenyl)-1,3-benzoxazole-6-carboxylic acid has been described to inhibit abnormal TTR aggregation and fibril formation, and is undergoing clinical trials for the treatment of cardiomyopathy in familial and wild-type TTR patients. Tafamidis is still under evaluation from the FDA, the principal medicine registration office.

Despite continued efforts in managing and improving the treatments of subjects with abnormal TTR aggregation and fibril formation, there remains little improvement. For example, recent retrospective review from the Mayo Clinic, the largest amyloid referral center in the United States, indicated that there has been no appreciable change in the overall mortality in subjects with TTR amyloid cardiomyopathy (ATTR-CM) between 1965 and 2013 (Grogan et al. *J Am Coll Cardiol* 2016; 68(10): 1014-20).

As such, there exists a need in the art to provide methods for treating abnormal TTR aggregation and fibril formation. The present disclosure addresses these needs and provides related advantages as well.

BRIEF SUMMARY OF THE INVENTION

In some aspects, provided herein are methods of treating transthyretin (TTR) amyloidosis in a subject in need thereof, the method comprising administering to a subject in need thereof a therapeutically effective amount of Compound 1, having the formula:

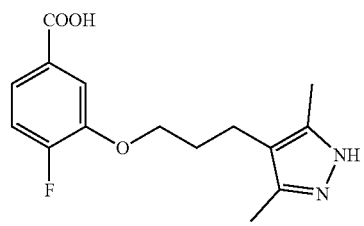 [SMILES: Cc1n[nH]c(C)c1CCCOc1cc(C(=O)O)ccc1F]

or a pharmaceutically acceptable salt thereof, wherein said therapeutically effective amount is a total daily dosage of about 50 mg to 2,000 mg.

In some embodiments, the total daily dosage of Compound 1 is about 800 mg. In some embodiments, the total daily dosage of Compound 1 is about 1,600 mg. In some embodiments, the HCl salt form of Compound 1 is administered.

In some embodiments, Compound 1 is administered once daily. In some embodiments, Compound 1 is administered twice daily.

In some aspects, provided herein are methods of treating transthyretin (TTR) amyloidosis in a subject in need thereof, the method comprising administering to a subject in need thereof a therapeutically effective amount of Compound 1, having the formula:

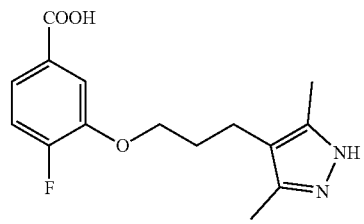 [SMILES: Cc1n[nH]c(C)c1CCCOc1cc(C(=O)O)ccc1F]

or a pharmaceutically acceptable salt thereof, wherein the therapeutically effective amount of Compound 1 maintains a desired trough blood plasma concentration of Compound 1.

In an additional aspect, provided herein is a single unit dosage about 10-1,000 mg of Compound 1, having the formula:

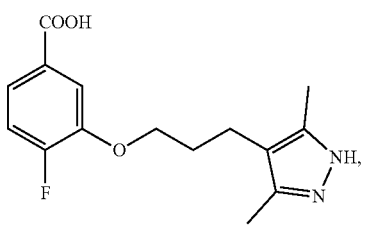 [SMILES: Cc1n[nH]c(C)c1CCCOc1cc(C(=O)O)ccc1F]

or a pharmaceutically acceptable salt thereof.

In some embodiments, the single unit dosage form comprises 200 mg of Compound 1. In some embodiments, the single unit dosage form comprises 400 mg of Compound 1. In some embodiments, the singe unit dosage comprises the HCl salt of Compound 1.

Other objects, features, and advantages of the present invention will be apparent to one of skill in the art from the following detailed description and figures.

BRIEF DESCRIPTION OF THE DRAWINGS

FIG. 16A-C shows the binding affinities and potency of stabilizers for TTR in buffer. (A) Interaction of TTR with stabilizers assessed by ITC. Thermodynamic data (summarized in Table 5); ΔG, ΔH, and −TΔS are as indicated in the legend. (B) Fluorescence change caused by modification of TTR in buffer (2.5 µM) by FPE probe monitored in the presence of probe alone (Control DMSO) or TTR stabilizers (2.5 µM; 1:1 Stabilizers to TTR ratio). (C) Bar graph representation of percent occupancy of TTR in buffer by stabilizers in the presence of FPE probe measured after 3 hr of incubation relative to probe alone. Error bars indicate SD (n=3). The significance of the differences were measured by one-way ANOVA followed by Tukey's multiple comparison test (*p≤0.05; ***p≤0.001).

FIG. 17A-D shows the efficacy of stabilizers in occupying and stabilizing TTR in human serum. (A) Representative western blot image for the stabilization of TTR in human serum subjected to acid-mediated (pH 4.0) denaturation in the presence of AG10 (10 µM) and other stabilizers tested at their estimated mean clinical $C_{max}$ at steady state when administered at the doses indicated: diflunisal (250 mg bid, 200 µM); tafamidis (80 mg qd), 20 µM; tolcapone (100 mg tid), 20 µM. (B) Bar graph representation of stabilization data obtained from Western blot experiments. Error bars indicate SD (n=3). (C) Fluorescence change caused by modification of TTR in human serum by FPE probe monitored in the presence of probe alone (Control DMSO), AG10 (10 µM), or TTR stabilizers (at their estimated mean clinical steady state Cm). (D) Bar graph representation of percent occupancy of TTR in human serum by stabilizers in the presence of FPE probe measured after 3 hr of incubation relative to probe alone. Error bars indicate SD (n=4). The significance of the differences were measured by one-way ANOVA followed by Tukey's multiple comparison test (n.s., not significant; *p≤0.05; p≤0.01; *p≤0.001).

FIG. 19A-E illustrates the hydrogen bonds between the pyrazole ring of AG10 and S117/S117' of TTR are important for effective binding to TTR. (A) Chemical structures and in silico docking study of synthesized AG10 analogues 1, 2, 3, and 4. Co-crystal structure of AG10 bound to TTR used for the docking experiment. 1 is the iodo-analogue of AG10. 2 is the methyl-ester form of AG10 that cannot form salt bridge with K15/15'. 3 is the methyl-pyrazole form of AG10 that can potentially form only one hydrogen bond with either K15 or K15'. 4 is the diethyl-pyrazole analogue of AG10 which affects both hydrogen bonds with S117/S117'. (B) Interaction of TTR with analogues assessed by ITC. Thermodynamic data; ΔG, ΔH, and −TΔS are as indicated in the legend. (C) Fluorescence change caused by modification of TTR in buffer (2.5 μM) by FPE probe monitored in the presence of probe alone (Control DMSO) or TTR stabilizers (2.5 μM; 1:1 Stabilizers to TTR ratio). (D) Bar graph representation of percent occupancy of TTR in buffer by stabilizers in the presence of FPE probe measured after 3 hr of incubation relative to probe alone. Error bars indicate SD (n=3). (E) Bar graph representation of Western blot data for the stabilization of TTR in human serum by analogues (10 μM; 2:1 Stabilizers to TTR ratio). Error bars indicate SD (n=4). The significance of the differences were measured by one-way ANOVA followed by Tukey's multiple comparison test (n.s., not significant; *$p \leq 0.05$; $p \leq 0.01$; *$p \leq 0.001$).

FIG. 21A-D shows activity of AG10 and tafamidis in the FPE and Western blot assays performed with pooled dog serum. (A) Fluorescence change caused by modification of dog TTR in commercially available beagle dog serum by FPE probe monitored in the presence of probe alone (Control DMSO, black circles), AG10 (10 μM) or tafamidis (10 μM). (B) Percent occupancy of dog TTR in dog serum by AG10 and tafamidis in the presence of FPE probe measured after 3 hr of incubation relative to probe alone. Error bars indicate SD (n=4). (C) Western blot image for the stabilization of TTR in pooled dog serum against acid-mediated denaturation in the presence of AG10 (10 μM) and tafamidis (10 μM). Serum samples were incubated with DMSO or test compounds in acetate buffer (pH 4.0) for the desired time period (0 and 72 h) before crosslinking and immunoblotting. (D) Bar graph representation of stabilization data obtained from Western blot experiments. Error bars indicate SD (n=3). The significance of the differences were measured by one-way ANOVA followed by Tukey's multiple comparison test (n.s., not significant; *$p \leq 0.05$; $p \leq 0.01$; *$p \leq 0.001$).

FIG. 22A-D shows that orally administered AG10 is effective in binding and stabilizing TTR in dogs. (A and B) Occupancy of TTR in beagle dogs after oral administration (q.d. for 7 days) of escalating doses of AG10. Circles (•) indicate pre-dose day 1, squares (■) indicate pre-dose day 7 (AG10 concentration at $C_{min}$), and triangles (▲) indicate post-dose day 7 (AG10 concentration at $C_{max}$). Four groups of animals were dosed: (i) 0 mg/kg (n=12, 6 males/6 females); (ii) 50 mg/kg (n=4, 2 males/2 females); (iii) 100 mg/kg (n=4, 2 males/2 females); (iv) 200 mg/kg (n=12, 6 males/6 females) (B) Bar graph representing TTR occupancy at 3 hr. Error bars indicate SD (n=3). (C and D) Pharmacokinetic-Pharmacodynamic (PK-PD) analysis of AG10 in dogs receiving a single oral dose of AG10 HCl at (C) 5 mg/kg and (D) 20 mg/kg. Scatterplot of concentration [AG10] vs. % TTR occupancy of serum samples obtained from dogs at various time points (n=4, 2 males/2 females per dosing group). Error bars indicate SD (n=3). The significance of the differences were measured by one-way ANOVA followed by Tukey's multiple comparison test (n.s., not significant; *$p \leq 0.05$; $p \leq 0.01$; *$p \leq 0.001$).

DETAILED DESCRIPTION OF THE INVENTION

I. General

Figure 1:
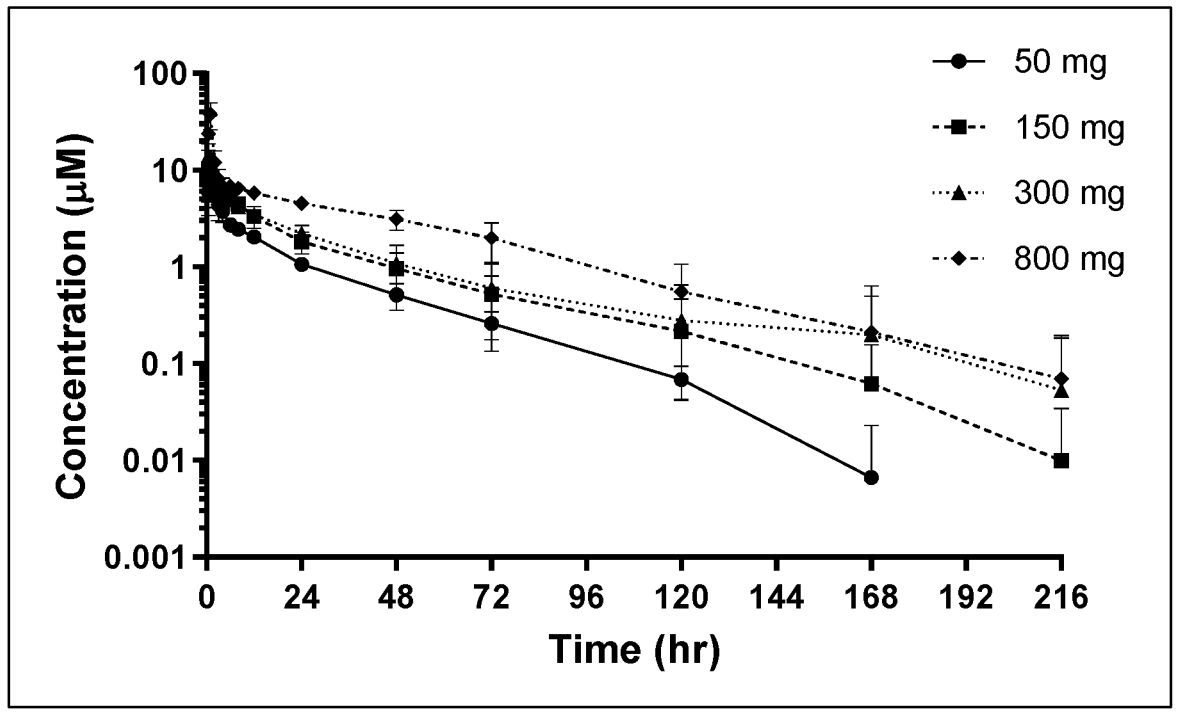
FIG. 1 shows the pharmacokinetic (PK) profiles of single ascending dose cohorts 1-4 at 50 mg, 150 mg, 300 mg, and 800 mg oral doses of AG10 HCl.

Described herein are methods for treating transthyretin (TTR) amyloidosis in a subject. The methods include specific dosing regimens that have great efficacy in treating the subject and that are well tolerated in subjects.

II. Definitions

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY, 2nd ed., J. Wiley & Sons (New York, N.Y. 1994); Sambrook et al., MOLECULAR CLONING, A LABORATORY MANUAL, Cold Springs Harbor Press (Cold Springs Harbor, N Y 1989). Any methods, devices and materials similar or equivalent to those described herein can be used in the practice of this invention. The following definitions are provided to facilitate understanding of certain terms used frequently herein and are not meant to limit the scope of the present disclosure.

"Compound 1" refers to the chemical 3-(3-(3,5-dimethyl-1H-pyrazol-4-yl)propoxy)-4-fluorobenzoic acid (AG10), having the formula:

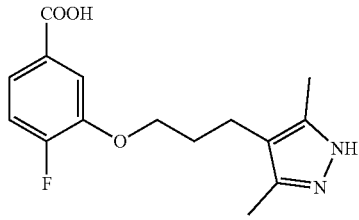

(Compound 1)

or a pharmaceutically acceptable salt thereof. When referring to specific amounts of Compound 1 administered to patients, this application refers to the amount of Compound 1 HCl salt administered. A person of skill in the art would recognize that in order to administer the same amount of Compound 1 in freebase or in a different salt form, small adjustments in overall amount administered is necessary.

The terms "a" or "an," as used in herein means one or more.

The terms "comprise," "include," and "have," and the derivatives thereof, are used herein interchangeably as comprehensive, open-ended terms. For example, use of "comprising," "including," or "having" means that whatever element is comprised, had, or included, is not the only element encompassed by the subject of the clause that contains the verb.

As used herein, the term "about" means a range of values including the specified value, which a person of ordinary skill in the art would consider reasonably similar to the specified value. In some embodiments, the term "about" means within a standard deviation using measurements generally acceptable in the art. In some embodiments, about means a range extending to +/−10% of the specified value. In some embodiments, about means the specified value.

As used herein, "treatment" or "treating," or "palliating" or "ameliorating" are used interchangeably herein. These terms refer to an approach for obtaining beneficial or desired results including but not limited to a therapeutic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the subject may still be afflicted with the underlying disorder. Treatment includes causing the clinical symptoms of the disease to slow in development by administration of a composition; suppressing the disease, that is, causing a reduction in the clinical symptoms of the disease; inhibiting the disease, that is, arresting the development of clinical symptoms by administration of a composition after the initial appearance of symptoms; and/or relieving the disease, that is, causing the regression of clinical symptoms by administration of a composition after their initial appearance. For example certain methods described herein treat transthyretin (TTR) amyloidosis by decreasing or reducing the occurrence, or progression of TTR fibril formation; or treat TTR amyloidosis by decreasing a symptom of TTR amyloidosis.

An "effective amount" or a "pharmaceutically effective amount" is an amount sufficient to accomplish a stated purpose (e.g. achieve the effect for which it is administered, treat a disease, reduce enzyme activity, reduce one or more symptoms of a disease or condition). An example of an "effective amount" is an amount sufficient to contribute to the treatment, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). Efficacy can also be expressed as "-fold" increase or decrease. For example, a therapeutically effective amount can have at least a 1.2-fold, 1.5-fold, 2-fold, 5-fold, or more effect over a control.

"Patient" or "subject" or "subject in need thereof" refers to a living organism suffering from or prone to a disease or condition that can be treated by using the methods provided herein. The term does not necessarily indicate that the subject has been diagnosed with a particular disease, but typically refers to an individual under medical supervision. Non-limiting examples include humans, other mammals, bovines, rats, mice, dogs, monkeys, goat, sheep, cows, deer, and other non-mammalian animals. In some embodiments, a patient, subject, or subject in need thereof is a human.

III. Detailed Description of the Embodiments

Methods

In one aspect, provided herein is a method of treating transthyretin (TTR) amyloidosis. The method includes administering to a subject in need thereof a therapeutically effective amount of Compound 1, having the formula:

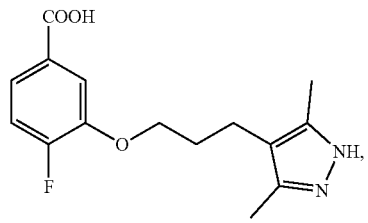 [SMILES: Cc1n[nH]c(C)c1CCCOc1cc(C(=O)O)ccc1F]

or a pharmaceutically acceptable salt thereof, where the therapeutically effective amount is a total daily dosage of about 10 mg to 2,000 mg. In some embodiments, the total daily dosage of Compound 1 is about 10 mg to 50 mg, 50 mg to 300 mg, 50 mg to 150 mg, 150 mg to 800 mg, 800 mg to 1,600 mg or 800 mg to 2,000 mg. In some embodiments, the total daily dosage of Compound 1 is about 10 mg to 50 mg. In some embodiments, the total daily dosage of Compound 1 is about 50 mg to 300 mg. In some embodiments, the total daily dosage of Compound 1 is 50 mg to 150 mg. In some embodiments, the total daily dosage of Compound 1 is 150 mg to 800 mg. In some embodiments, the total daily dosage of Compound 1 is 800 mg to 1,600 mg. In some embodiments, the total daily dosage of Compound 1 is 800 mg to 2,000 mg. It is understood that in the present disclosure the amount of Compound 1 listed is the amount of HCl salt of Compound 1 administered. A person of skill in the art would recognize that in order to administer the same amount of Compound 1 in freebase or in a different salt form, small adjustments in overall amount administered is necessary.

In some embodiments the total daily dosage of Compound 1 is about 10 mg. In some embodiments the total daily dosage of Compound 1 is about 25 mg. In some embodiments the total daily dosage of Compound 1 is about 50 mg. In some embodiments the total daily dosage of Compound 1 is about 1000 mg. In some embodiments the total daily dosage of Compound 1 is about 150 mg. In some embodiments the total daily dosage of Compound 1 is about 200 mg. In some embodiments the total daily dosage of Compound 1 is about 300 mg. In some embodiments the total daily dosage of Compound 1 is about 600 mg. In some embodiments the total daily dosage of Compound 1 is about 800 mg. In some embodiments the total daily dosage of Compound 1 is about 1,6000 mg.

The Compound 1 can be administered once (SID or qd), twice (BID or q12h), three (TID), or four times (QID) a day. In some embodiments, Compound 1 is administered once daily. In some embodiments, Compound 1 is administered twice daily. In some embodiments, Compound 1 is administered three times daily. In some embodiments, Compound 1 is administered four times daily.

In some embodiments, about 50 mg of Compound 1 is administered once daily. In some embodiments, about 150 mg of Compound 1 is administered once daily. In some embodiments, about 300 mg of Compound 1 is administered once daily. In some embodiments, about 800 mg of Compound 1 is administered once daily.

In some embodiments, about 100 mg of Compound 1 is administered twice daily. In some embodiments, about 300 mg of Compound 1 is administered twice daily. In some embodiments, about 400 mg of Compound 1 is administered twice daily. In some embodiments, about 800 mg of Compound 1 is administered twice daily.

In another aspect, provided herein is a method of treating transthyretin (TTR) amyloidosis. The method includes administering to a subject in need thereof a therapeutically effective amount of Compound 1, having the formula:

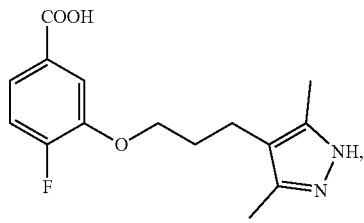 [SMILES: Cc1n[nH]c(C)c1CCCOc1cc(C(=O)O)ccc1F]

or a pharmaceutically acceptable salt thereof, where the therapeutically effective amount of Compound 1 maintains a trough blood plasma concentration of Compound 1 of at least 5 µM. In some embodiments, the therapeutically effective amount of Compound 1 maintains a trough blood plasma concentration of Compound 1 of at least 6 µM. In some embodiments, the therapeutically effective amount of Compound 1 maintains a trough blood plasma concentration of Compound 1 of at least 7.5 µM. In some embodiments, the therapeutically effective amount of Compound 1 maintains a trough blood plasma concentration of Compound 1 of at least 8 µM.

In some embodiments, the therapeutically effective amount of Compound 1 maintains a trough blood plasma concentration of Compound 1 from 5 to 30 µM. In some embodiments, the therapeutically effective amount of Compound 1 maintains a trough blood plasma concentration of Compound 1 from 5 to 25 µM. In some embodiments, the therapeutically effective amount of Compound 1 maintains a trough blood plasma concentration of Compound 1 from 6 to 20 µM. In some embodiments, the therapeutically effective amount of Compound 1 maintains a trough blood plasma concentration of Compound 1 from 7.5 to 15 µM. In some embodiments, the therapeutically effective amount of Compound 1 maintains a trough blood plasma concentration of Compound 1 from 7.5 to 10 µM.

In some embodiments, subjects receiving a therapeutically effective amount of Compound 1 experience an increase in transthyretin (TTR) blood serum concentrations relative to baseline levels. In some embodiments, subjects receiving a therapeutically effective amount of Compound 1 experience at least about a 10, 15, 20, 25, 30% or more increase in transthyretin (TTR) blood serum concentrations relative to baseline levels after 28 days of treatment. In some embodiments, subjects receiving a therapeutically effective amount of Compound 1 experience at least about a 25% increase in transthyretin (TTR) blood serum concentrations relative to baseline levels after 28 days of treatment. In some embodiments, subject prior to treatment have TTR blood serum levels that are beneath a baseline seru TTR concentration (20 mg/dL TTR). In some embodiments, subject receiving an effective amount of Compound 1 for 28 days will experience increased blood serum TTR levels such that the level of blood serum TTR is above the baseline level. In some embodiments, the subject experiencing increase TTR level are subjects diagnosed with transthyretin amyloidosis (ATTR) cardiomyopathy.

There are a variety of diseases or disorders associated with transthyretin (TTR) amyloidosis. These include, but are not limited to familial amyloid polyneuropathy, familial amyloid cardiomyopathy, senile systemic amyloidosis, central amyloidosis, ocular amyloidosis, Leptomeningeal amyloidosis, oculoleptomeningeal amyloidosis, vitreous amyloidosis, gastrointestinal amyloidosis, neuropathic amyloidosis, non-neuropathic amyloidosis, non-hereditary amyloidosis, reactive/secondary amyloidosis, cerebral amyloidosis.

In some embodiments, the disease or disorder associated with transthretin (TTR) amyloidosis is leptomeningeal amyloidosis. In some embodiments, subjects with leptomeningeal amyloidosis have a transthyretin protein with an aspartic acid to glycine mutation at position 18 (D18G). In some embodiments, subjects with leptomeningeal amyloidosis have a transthyretin protein with a glycine to arginine mutation at position 53 (G53R). The wild-type transthyretin (TTR) protein is provided herein as SEQ ID NO: 1.

In some embodiments, subjects with leptomeningeal amyloidosis have a transthyretin protein with a tyrosine to cysteine mutation at position 114 (Y114C). Subjects with the tyrosine to cysteine mutation at position 114 (Y114C) can exhibit ATTRm-PN symptoms, leptomeningeal amyloidosis symptoms, or a combination of both.

In some embodiments, subjects with leptomeningeal amyloidosis have a transthyretin protein with a threonine to proline mutation at position 49 (T49P). Subjects with the threonine to proline mutation at position 49 (T49P) can exhibit ATTRm-CM symptoms, leptomeningeal amyloidosis symptoms, or a combination of both.

In some embodiments, the transthyretin (TTR) amyloidosis disease is transthyretin amyloidosis (ATTR) cardiomyopathy or ATTR polyneuropathy. In some embodiments, the TTR amyloidosis is characterized by a TTR protein that comprises a threonine to alanine mutation at position 60 (T60A). In some embodiments, the TTR amyloidosis is characterized by a TTR protein that comprises a proline to serine mutation at position 24 (P24S). In some embodiments, the TTR amyloidosis is characterized by a TTR protein that comprises an aspartic acid to alanine mutation at position 38 (D38A). In some embodiments, the TTR amyloidosis is characterized by a TTR protein that comprises a leucine to histidine mutation at position 58 (L58H). Patients with these mutations often present a combination of both ATTR cardiomyopathy and ATTR polyneuropathy symptoms. The wild-type transthyretin (TTR) protein is provided herein as SEQ ID NO: 1.

In some embodiments, the transthyretin (TTR) amyloidosis disease is transthyretin amyloidosis (ATTR) cardiomyopathy. In some embodiments, the transthyretin (TTR) amyloidosis disease is transthyretin amyloidosis (ATTR) polyneuropathy.

ATTR cardiomyopathy includes wild-type ATTR cardiomyopathy (ATTRwt-CM) and genetic (familial) ATTR cardiomyopathy (ATTRm-CM). ATTRm-CM is caused by a mutation in the TTR protein, whereas ATTRwt-CM is not caused by a mutation. Instead, ATTRwt-CM is generally an age-related process. In some embodiments, the ATTR cardiomyopathy is ATTRwt-CM. In some embodiments, the ATTR cardiomyopathy is ATTRm-CM. In some embodiments, subjects with ATTRm-CM have a valine to isoleucine mutation at position 122 (V122I) in the TTR protein. In some embodiments, subjects with ATTRm-CM have a transthyretin protein with a threonine to proline mutation at position 49 (T49P). Subjects with the threonine to proline mutation at position 49 (T49P) can exhibit ATTRm-CM symptoms, leptomeningeal amyloidosis symptoms, or a combination of both. The wild-type transthyretin (TTR) protein is provided herein as SEQ ID NO: 1.

ATTR polyneuropathy includes both wild type & genetic (familial) ATTR polyneuropathy. As discussed for cardiomyopathy, ATTRm-PN is caused by a mutation in the TTR protein, whereas ATTRwt-PN does not include a genetic component. In some embodiments ATTR-PN is ATTRwt-PN. In some embodiments, ATTR-PN is ATTRm-PN. In some embodiments, the ATTRm-PN is characterized by a TTR protein that includes a valine to methionine mutation at position 30 (V30M). In some embodiments, the ATTRm-PN is characterized by a TTR protein that includes a phenylalanine to leucine mutation at position 64 (F64L). In some embodiments, the ATTRm-PN is characterized by a TTR protein that includes a tyrosine to cysteine mutation at position 114 (Y114C). Subjects with the tyrosine to cysteine mutation at position 114 (Y114C) can exhibit ATTRm-PN symptoms, leptomeningeal amyloidosis symptoms, or a combination of both. The wild-type transthyretin (TTR) protein is provided herein as SEQ ID NO: 1.

ATTR cardiomyopathy (both wild-type and familial) is a slowly progressive disease that causes heart failure and death in affected subjects. The methods of the present disclosure, provide clinical improvement in subjects with ATTR cardiomyopathy by stopping or slowing the accumulation of TTR fibrils in the myocardium. Through this process, the currently described methods provide clinical improvements in ATTR cardiomyopathy subjects. Clinical improvements include, but are not limited to, improvement in New York Heart Association (NYHA) functional classification, improvements in Kansas City Cardiomyopathy Questionnaire responses, EuroQoL-5 Dimensions (EQ-5D-5L), improvement in 6 minute walk test performance, improvement in markers associated with cardiac health such as Troponin T, Troponin I, B-type natriuretic peptide (BNP), and N-terminal pro-BNP, decreasing the frequency of cardiovascular-related hospitalizations, and/or decreasing mortality.

In some embodiments, the methods provided herein improve, stabilize or delay worsening in New York Heart Association (NYHA) functional classification of subjects. The NYHA functional classification grades the severity of heart failure symptoms as one of four functional classes. The NYHA functional classification is widely used in clinical practice and in research because it provides a standard description of severity that can be used to assess response to treatment and to guide management. The NYHA functional classification is based on severity of symptoms and limitation of physical activity:

Class I: No limitation of physical activity. Ordinary physical activity does not cause undue breathlessness, fatigue, or palpitations.

Class II: Slight limitation of physical activity. Comfortable at rest, but ordinary physical activity results in undue breathlessness, fatigue, or palpitations.

Class III: Marked limitation of physical activity. Comfortable at rest, but less than ordinary physical activity results in undue breathlessness, fatigue, or palpitations.

Class IV: Unable to carry on any physical activity without discomfort. Symptoms at rest can be present. If any physical activity is undertaken, discomfort is increased.

In some embodiments, administration of a therapeutically effective amount of Compound 1 reduces the New York Heart Association (NYHA) functional classification of the subject. In some embodiments, the NYHA functional classification is reduced from class IV to class III, from class IV to class II, or from class IV to class I. In some embodiments, the NYHA functional classification is reduced from class IV to class III. In some embodiments, the NYHA functional classification is reduced from class IV to class II. In some embodiments, the NYHA functional classification is reduced from class III to class II. In some embodiments, the NYHA functional classification is reduced from class III to class I. In some embodiments, the NYHA functional classification is reduced from class II to class I.

In some embodiments, the methods provided herein improve, stabilize or delay worsening in Kansas City Cardiomyopathy Questionnaire (KCCQ) classification of subjects. In some embodiments, the methods described herein provide improved scores in the Kansas City Cardiomyopathy Questionnaire (KCCQ) (Green C P, et al. (2000) Journal of the American College of Cardiology 35: 1245-55), the contents of which are incorporated herein by reference for all purposes. The KCCQ contains specific questions related to cardiac health and provides valid, reliable and sensitive measures of disease-specific health-related quality of life.

The questions of the KCCQ ask subjects to assess how limited (e.g. severely limited, limited quite a bit, moderately limited, slightly limited, or did not limit at all) they are in performing normal aspects of their life. In some embodiments, subjects have an average improvement of at least one level (e.g. severely limited to limited quite a bit, limited quite a bit to moderately limited, moderately limited to slightly limited) on all questions of the questionnaire after treatment with Compound 1.

In some embodiments, the methods provided herein improve, stabilize or delay worsening in EuroQoL-5 Dimensions (EQ-5D-5L) score in subjects. EQ-5D-5L is a brief, self-administered generic health status instrument that takes about 5 minutes to complete. The instrument includes two parts. In the first part, respondents are asked to rate their current health state on 5 dimensions (mobility, self-care, usual activities, pain or discomfort, and anxiety or depression) with each dimension having five levels of function (1-no problem, 2-slight problem, 3-moderate problem, 4-severe problem, and 5-extreme problem). The second part is a respondents self-rating of current health status on a Visual Analog Scale (EQ VAS) with endpoints labeled "best imaginable health state" (score of 100) and "worst imaginable health state" (score of 0). The scores from the 5 dimensions may be used to calculate a single index value, also known as a utility score. The EQ-5D-5L questionnaire is in the public domain and can be obtained from EuroQoL.

In some embodiments, patients receiving the treatment methods described herein have an average improvement of at least one, tow, three four, five, six, seven, either, nine, or ten points in the EuroQoL-5 Dimensions (EQ-5D-5L) utility score. In some embodiments, patients receiving the treatment methods described herein have an average improvement of at least five points in the EuroQoL-5 Dimensions (EQ-5D-5L) utility score.

In some embodiments, the methods described herein improve a subject's six minute walk test performance. The six minute walk test is a self-paced timed walk for six minutes to assess the level of functional capacity of a subject. Subjects are allowed to stop and rest during the test if the levels of exertion exceed their comfort level. Assessment before, after, and during treatment is relatively easy to assess and consists of measuring the distance the subject walks in a six-minute time period. Thus, in some embodiments, subjects increase total distance covered in the six minute walking test after treatment with Compound 1. In some embodiments, subjects walked at least 25 m further than a baseline distance measured prior to treatment with Compound 1. In some embodiments, subjects walked at least 30 m further than a baseline distance measured prior to treatment with Compound 1. In some embodiments, subjects walked at least 50 m further than a baseline distance measured prior to treatment with Compound 1. In some embodiments, subjects walked at least 75 m further than a baseline distance measured prior to treatment with Compound 1. In some embodiments, subjects walked at least 100 m further than a baseline distance measured prior to treatment with Compound 1. In some embodiments, subjects receiving the treatment methods described herein have a slowed reduction in six-minute walking distance. For example, in some embodiments, a subject mantains about the same six minute walking distance as prior to treatment. In some embodiments, a subject covers 10 m less in a a six minute wakling test. In some embodiments, the six minute walk test is used to compare the treatment group to the non-treatment group. In some embodiments, the between group mean change from baseline is at least 10 meters. In some embodiments, the between group mean change from baseline is at least 20 meters. In some embodiments, the between group mean change from baseline is at least 30 meters. In some embodiments, the treatment methods provided herein reduced the decline in the six minute walk test distance as compared to individuals not receiving treatment.

Troponin T, Troponin I, Brain natriuretic peptide (BNP), and N-terminal pro-BNP are polypeptides that are elevated in serum blood of subjects with poor myocardial health. In some embodiments, the level of Troponin T, Troponin I, BNP and/or N-terminal pro-BNP decrease after treatment with Compound 1. In some embodiments, the level of Troponin T, Troponin I, BNP and/or N-terminal pro-BNP decrease about 10% as compared to a baseline level of Troponin T, Troponin I, BNP and/or N-terminal pro-BNP in said subject prior to treatment with Compound 1. In some embodiments, the level of Troponin T, Troponin I, BNP and/or N-terminal pro-BNP decrease about 15% as compared to a baseline level of Troponin T, Troponin I, BNP and/or N-terminal pro-BNP in said subject prior to treatment with Compound 1.

As discussed above, a clinical improvement provided in some embodiments of the disclosed methods, is decreasing the rate of cardiovascular related hospitalizations in subjects receiving treatment as compared to those who do not receive treatment. In some embodiments, piatents on average at least 0.5, 1, 1.5, 2, 3, 4, 5 fewer cardiovascular related hospitalizations per year as compared to those who do not receive treatment.

An additional clinical benefit that is provided in some embodiments of the methods disclosed herein, is a decrease in mortality rate as compared to individuals not receiving treatment. In some embodiments, mortality rate is reduced by about 2, 4, 6, 8, 10, 12, 14, 16, 18, 20, 22, 24, 26, 28, 30 or more percent as compared to subjects who did not receive treatment.

ATTR polyneuropathy is a disease where TTR amyloid (ATTR) deposits impair or otherwise compromise normal nerve function. ATTR polyneuropathy is a progressive disease that causes cachexia and death in affected subjects. The methods of the present disclosure, provide clinical improvement in subjects with ATTR polyneuropathy by stopping or slowing the accumulation of TTR fibrils. Through this process, the currently described methods provide clinical improvements ATTR polyneuropathy subjects. Clinical improvements include, but are not limited to, improvements in Neuropathy Impairment Score (NIS) or modified Neuropathy Impairment Score+7 (mNIS+7), improvements in Norfolk Quality of Life Diabetic Neuropathy questionnaire, improvements in composite autonomic symptom score (COMPASS-31) score, improved nutritional status as measured by modified body mass index (mBMI), and/or improvements in a subject's 10 meter walk test.

In some embodiments, the methods described herein provide improved Neuropathy Impairment Score (NIS). NIS refers to a scoring system that measures weakness, sensation, and reflexes. The NIS score evaluates a standard group of muscles for weakness (1 is 25% weak, 2 is 50% weak, 3 is 75% weak, 3.25 is movement against gravity, 3.5 is movement with gravity eliminated, 3.75 is muscle flicker without movement, and 4 is paralyzed), a standard group of muscle stretch reflexes (0 is normal, 1 is decreased, 2 is absent), and touch-pressure, vibration, joint position and motion, and pinprick (all graded on index finger and big toe: 0 is normal, 1 is decreased, 2 is absent). Evaluations are corrected for age, gender, and physical fitness.

In some embodiments, the methods described herein slow the progression of the disease such that the rate of NIS score increase is reduced as compared to a subject who is not taking Compound 1. In some embodiments, the methods described herein stop the progression of the disease such that there is no change in NIS score after treatment with Compound 1.

In some embodiments, the methods described herein reduce the NIS score after treatment with Compound 1. In some embodiments, the methods described herein reduced the NIS score by at least 5, 10, 15, 20, 25, 30, 35, 40, 45, 50, 55, or 60% as compared to a baseline level measured prior to treatment with Compound 1. In some embodiments, the methods described herein reduced the NIS score by at least 5% as compared to a baseline level measured prior to treatment with Compound 1. In some embodiments, the methods described herein reduced the NIS score by at least 10% as compared to a baseline level measured prior to treatment with Compound 1. In some embodiments, the methods described herein reduced the NIS score by at least 15% as compared to a baseline level measured prior to treatment with Compound 1.

In some embodiments, the methods described herein provide improved modified Neuropathy Impairment Score (mNIS+7). mNIS+7 refers to a clinical exam-based assessment of neurologic impairment (NIS) combined with electrophysiologic measures of small and large nerve fiber function (NCS and QST), and measurement of autonomic function (postural blood pressure). The mNIS+7 score is a modification of the NIS+7 score (which represents NIS plus seven tests). NIS+7 analyzes weakness and muscle stretch reflexes. Five of the seven tests include attributes of nerve conduction. These attributes are the peroneal nerve compound muscle action potential amplitude, motor nerve conduction velocity and motor nerve distal latency (MNDL), tibial MNDL, and sural sensory nerve action potential amplitudes. These values are corrected for variables of age, gender, height, and weight. The remaining two of the seven tests include vibratory detection threshold and heart rate decrease with deep breathing. The mNIS+7 score modifies NIS+7 to take into account the use of Smart Somatotopic Quantitative Sensation Testing, new autonomic assessments, and the use of compound muscle action potential of amplitudes of the ulnar, peroneal, and tibial nerves, and sensory nerve action potentials of the ulnar and sural nerves (Suanprasert, N. et al., Retrospective study of a TTR FAP cohort to modify NIS+7 for therapeutic trials, J. Neurol. Sci., 2014. 344(1-2): pgs. 121-128). Further details of the mNIS+7 exam can be found in US 2017/0307608, the contents of which is incorporated herein by reference, for all purposes.

In some embodiments, the methods described herein slow the progression of the disease such that the rate of mNIS+7 score increase is reduced as compared to a subject who is not taking Compound 1. In some embodiments, the methods described herein stop the progression of the disease such that there is no change in mNIS+7 score after treatment with Compound 1.

In some embodiments, the methods described herein reduce the mNIS+7 score after treatment with Compound 1. In some embodiments, the methods described herein reduced the mNIS+7 score by at least 5, 10, 15, 20, 25, 30, 35, 40, 45, 50, 55, or 60% as compared to a baseline level measured prior to treatment with Compound 1. In some embodiments, the methods described herein reduced the mNIS+7 score by at least 5% as compared to a baseline level measured prior to treatment with Compound 1. In some embodiments, the methods described herein reduced the mNIS+7 score by at least 10% as compared to a baseline level measured prior to treatment with Compound 1. In some embodiments, the methods described herein reduced the mNIS+7 score by at least 15% as compared to a baseline level measured prior to treatment with Compound 1.

In some embodiments, the methods described herein provide improved scores in the Norfolk Quality of Life Diabetic Neuropathy (QOL-DN) questionnaire. This questionnaire is well known to a person of skill in the art, and is a validated questionnaire that captures pain related to large fiber, small fiber, and autonomic neuropathy. The questionnaire includes items related to symptoms experienced by the subject and questions related to the impact of neuropathy on the daily activities of a subject.

In some embodiments, the methods described herein slow the progression of the disease such that the rate of the Norfolk QOL-DN score decline is reduced as compared to a subject who is not taking Compound 1. In some embodiments, the methods described herein stop the progression of the disease such that there is no change in the Norfolk QOL-DN score after treatment with Compound 1.

In some embodiments, the methods described herein slow the progression of the disease such that there is no change in the Norfolk QOL-DN score after treatment with Compound 1.

In some embodiments, the methods described herein improve the Norfolk QOL-DN score after treatment with Compound 1. In some embodiments, the methods described herein improve the Norfolk QOL-DN by at least 5, 10, 15, 20, 25, 30, 35, 40, 45, 50, 55, or 60% as compared to a baseline level measured prior to treatment with Compound 1. In some embodiments, the methods described herein improve the Norfolk QOL-DN score by at least 5% as compared to a baseline level measured prior to treatment with Compound 1. In some embodiments, the methods described herein improve the Norfolk QOL-DN score by at least 10% as compared to a baseline level measured prior to treatment with Compound 1. In some embodiments, the methods described herein improve the Norfolk QOL-DN score by at least 15% as compared to a baseline level measured prior to treatment with Compound 1. In some embodiments, the methods described herein provide a change in a subject's Norfolk QOL-DN of about −1.5, −2.0, −2.5, −3.0, −3.5, −4.0, −4.5, −5.0, −5.5, −6.0, −6.7, −7.0, −7.5, −8.0, −8.5, −9.0, −9.5, or −10.0 as compared to a subject's baseline score.

In some embodiments, the methods disclosed herein provide imporved composite autonomic symptom score (COMPASS-31). The composite autonomic symptom score (COMPASS-31) is a patient questionnaire that assesses symptoms of dysautonomia. In one embodiment, the methods of the invention provide to the subject an improvement versus baseline in a COMPASS-31 score. Such an improvement can take the form of an increase of at least 0.1, for example at least 0.2, at least 0.3, at least 0.4, or at least 0.5, e.g., 0.1, 0.2, 0.3, 0.4, or 0.5, points of the subject's COMPASS-31 score. In some embodiments, the methods slow the progression of the disease such that there is no change in the COMPASS-31 score. In yet other embodiments, the methods of the invention slow the rate at which a COMPASS-31 score decreases, e.g., the rate of decrease of a COMPASS-31 score in a subject treated with AG10 as compared to the rate of decrease of a COMPASS-31 score in a subject that is not treated with AG10.

In some embodiments, the methods disclosed herein provide imporved nutritional status as measured by modified body mass index (mBMI), which is determined by multiplying the BMI of an individuals by their serum albumin levels. The calculation of mBMI accounts for the contribution of edema to total weight. In one embodiment, the methods of the disclosure provide to the subject an improvement versus baseline in mBMI. Such an improvement can take the form of a mBMI score decrease of about 2, 5, 7, 10, 12, 15, 20, or about 25. In other embodiments, the methods arrest an increasing mBMI index score, e.g., the methods result in a 0% increase of the mBMI score. In yet other embodiments, the methods of the invention slow the rate at which mBMI score increases, e.g., the rate of increase of a mBMI score in a subject treated with AG10 as compared to the rate of increase of a mBMI score in a subject that is not treated with AG10.

In some embodiments, the methods disclosed herein provide improvements in the 10-meter walk test. This test measures an individuals walking speed over 10 meters. In one embodiment, the methods of the disclosure provide to the subject an increase from baseline in the 10-meter walk test. In some embodiments, the increase from baseline in the 10-meter walk test is about 0.025, 0.03, 0.04, 0.05, 0.06, 0.07, 0.08, 0.09, 1.0, 1.5, 2.0, 2.5, 3.0, 3.5, 4.0. 4.5, or about 5.0 meters/second.

In some embodiments, the methods disclosed herein provide imporved Dyck/Rankin scores. The Dyck/Rankin score is known in the art, and is assigned by a physician after assessing the patient's symptoms, neuropathic impairments, test results, and reviewing a patient's ability to perform acts of daily living. Only disability related to peripheral neuropathy is graded. In deciding whether the patient has difficulty or inability to perform certain tasks or acts of daily living, more than the patient's report should be used for judgment; the physician should use objective criteria. The stages (0-8) are outlined below:

0. No neuropathy
   No symptoms (NSS<1), signs (NIS<2 points); or tests (e.g. 7 tests<$97.5^{th}$) abnormalities of neuropathy.
1. Minimal neuropathy (only one of A, B. C are abnormal)
   a) Tests, are the only abnormality (e.g. 7 test>$97.5^{th}$); or
   b) Neuropathy signs, are the only abnormality (e.g. NIS>2 points); or
   c) Neuropathy symptoms are the only abnormality (e.g. NSS>1)
2. Minimal neuropathy: 1a+1b.
3. Symptomatic neuropathy: 1a, 1a+1c; 1a+1c or 1b+1c. The patient is able to continue with usual-acts of daily living, work or recreational activity, and can meet usual-family and social responsibilities.
   Symptoms of neuropathy: NSS>1 symptoms of muscle weakness, atrophy or cramps; negative or positive, neuropathic sensory symptoms (N-NNS,P-NSS); or neuropathic autonomic symptoms.
   Usual acts of daily living, work, recreational and social and family activities: Despite neuropathic symptoms, the patient is able to work at his usual activity, maintain his usual home obligations and participate in recreational activities. Generally, the patient can carry-on despite some motor, sensory or autonomic symptoms. The patients may be unable to perform extraordinary activities e.g. competitive sports, feats of endurance, etc.
4. Symptomatic neuropathy (defined in 3) interfering and limiting work, usual acts of daily living, recreational activity or family and social obligations but independent function is possible without the help of others. At this score, there is an unequivocal limitation of usual* work, acts of living or recreational, family or social obligations * because of neuropathy.
   The degree of motor, sensory or autonomic symptoms or impairment is of a sufficient degree to limit the ability to work, to perform usual acts of daily living, recreational activities or to meet family and usual social responsibilities. The use of a can or orthotic device probably places the patient in this (or a higher) category unless the patient is able to perform "usual" acts of daily living, recreational activities and meet social and family responsibilities (then they would fall into lower category).
5. Symptomatic neuropathy (defined in 3) restricting acts of daily living, work and recreational activities. The help of other care-givers* (<2½ hrs/day) is needed. If use of a wheelchair is mandatory for acts of daily loving, recreational activities or social and family responsibilities, the patient would usually fall into this or a higher score (>5).
   A member of the family or visiting nurse is needed to provide acts of daily living (bathing, shaving, tooth brushing, feeding, etc.), daily management of analgesics or opiates or help with management of autonomic dysfunction which the patient is not able to perform adequately or safely on their own.
6 Symptomatic neuropathy (defended in 3) requiring the help of care-givers >2½ hrs to <8 hrs/day as described in 5.
7. Symptomatic neuropathy (defined in 3) requiring the help of care giver >8 hrs/day but not continuously as in stage 8.
8. Symptomatic neuropathy (defined in 3) requiring constant care in an intensive care unit.

The time period for administration will depend on a number of factors including the specific disease being treated. For example, in particular transthyretin (TTR) amyloidosis diseases or condition, there is a genetic component such that chronic (i.e. continuous, long term) administration may be required. However, in some embodiments, administration of Compound 1 to subject with a genetic TTR amyloidosis disease will continue while the subject is demonstrating or experiencing symptoms related to the TTR amyloidosis disease or condition, or for a set period of time after a particular end point is met (e.g. reduction or complete elimination of symptoms). If the symptoms of the TTR amyloidosis disease return or begin to reappear, administration of Compound 1 is re-started.

For subjects with a non-genetic linked TTR amyloidosis disease, a number administration options are available and will depend on the severity of the disease and the clinical symptoms presented. In some embodiments, long term administration of Compound 1 is necessary. In some embodiments, shorter term, or acute, administration of Compound 1 is necessary. In some embodiments, administration of Compound 1 to a subject with a non-genetic linked TTR amyloidosis disease is continued while the subject is demonstrating or experiencing symptoms related to the TTR amyloidosis disease or condition, or for a set period of time after a particular end point is met (e.g. reduction or complete elimination of symptoms). If the symptoms of the TTR amyloidosis disease return or begin to reappear, administration of Compound 1 is re-started.

In some embodiments, Compound 1 is administered for at least 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83 84, 85, 86, 87, 88, 89, 90, 91, 92, 93, 94, 95, 96, 97, 98, 99, 100 days or longer. In some embodiments, Compound 1 is administered for 7, 14, 21, 28, 35, 42, 49, or 56 days. In some embodiments, Compound 1 is administered for 28 days. In some embodiments, Compound 1 is administered for 56 days. In some embodiments, Compound 1 is administered for 84 days.

In some embodiments, Compound 1 is administered for at least 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 38, 39, 40, 41, 42, 43, 44, 45, 46, 47, 48, 49, 50 months or. In some embodiments, Compound 1 is administered for 10, 15, 20, 25, 30, 35, 40, 45, or 50 months. In some embodiments, Compound 1 is administered for 6 months. In some embodiments, Compound 1 is administered for 12 months. In some embodiments, Compound 1 is administered for 18 months. In some embodiments, Compound 1 is administered for 24 months. In some embodiments, Compound 1 is administered for 30 months. In some embodiments, Compound 1 is administered for 36 months. In some embodiments, Compound 1 is administered for 42 months.

Advantageously, agents used in diuretic therapy did not alter the exposure of AG10 during treatment. As such, patients receiving diuretic therapy can be administered AG10 without altered or specialized dosing regimens. Thus, in some embodiments, the subject receiving AG10 is also receiving an additional diuretic therapy agent. Diuretic therapy agents include, but are not limited to, ethacrynic acid, bumetanide, furosemide, and torsemide. In some embodiments, the diuretic is selected from the group consisting of furosemide or torsemide.

Pharmaceutical Compositions

Compound 1 can be prepared in various compositions suitable for delivery to a subject. A composition suitable for administration to a subject typically comprises Compound 1, or a pharmaceutically acceptable salt thereof and a pharmaceutically acceptable excipient.

The pharmaceutical compositions for the administration of Compound 1 can conveniently be presented in unit dosage form and can be prepared by any of the methods known in the art of pharmacy and drug delivery. All methods include the step of bringing the active ingredient into association with a carrier containing one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation.

Suitable formulations for use in the present invention are found in Remington: THE SCIENCE AND PRACTICE OF PHARMACY, 21st Ed., Gennaro, Ed., Lippincott Williams & Wilkins (2003), which is hereby incorporated herein by reference. The pharmaceutical compositions described herein can be manufactured in a manner that is known to those of skill in the art, i.e., by means of conventional mixing, dissolving, granulating, dragee-making, levigating, emulsifying, encapsulating, entrapping or lyophilizing processes. The following methods and excipients are merely exemplary and are in no way limiting.

Compound 1 can be incorporated into a variety of formulations for therapeutic administration. More particularly, Compound 1 can be formulated into pharmaceutical compositions, together or separately, by formulation with appropriate pharmaceutically acceptable carriers or diluents, and can be formulated into preparations in solid, semi-solid, liquid or gaseous forms, such as tablets, capsules, pills, powders, granules, dragees, gels, slurries, ointments, solutions, suppositories, injections, inhalants and aerosols. As such, administration of a compound of the present invention can be achieved in various ways, including oral, buccal, parenteral, intravenous, intradermal (e.g., subcutaneous, intramuscular), transdermal, etc., administration. Moreover, Compound 1 can be administered in a local rather than systemic manner, for example, in a depot or sustained release formulation.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxy-ethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical Dosage Forms

The present disclosure includes pharmaceutical dosage forms of Compound 1, or a pharmaceutically acceptable form thereof. The dosage forms described herein are suitable for oral administration to a subject. The dosage form may be in any form suitable for oral administration, including, but not limited to, a capsule or a tablet.

In some embodiments, the present disclosure provides a single unit dosage capsule or tablet form containing 10-1,000 mg of Compound 1, having the formula:

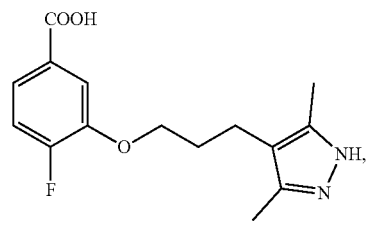

or a pharmaceutically acceptable salt thereof.

In some embodiments, the amount of Compound 1 is from about 100 to 800 mg. In some embodiments, the amount of Compound 1 is from about 150 to 600 mg. In some embodiments, the amount of Compound 1 is from about 200 to 400 mg. In some embodiments, the amount of Compound 1 is about 200 mg. In some embodiments, the amount of Compound 1 is about 400 mg. In some embodiments, the singe dosage capsule or tablet comprises the HCl salt of Compound 1.

In some embodiments, the single unit dosage form of Compound 1 is a tablet.

In some embodiments, the single unit dosage form of Compound 1 is a capsule.

In some embodiments, the single unit dosage form is in a capsule of size #0, #1, #2, #3, #4, or #5. In some embodiments, the single unit dosage form is in a capsule of size #0. In some embodiments, the single unit dosage form is in a capsule of size #1. In some embodiments, the single unit dosage form is in a capsule of size #2. In some embodiments, the single unit dosage form is in a capsule of size #3. In some embodiments, the single unit dosage form is in a capsule of size #4. In some embodiments, the single unit dosage form is in a capsule of size #5.

Kits

The disclosure also encompasses kits comprising pharmaceutical compositions and dosage forms of the invention.

In some aspects, the present invention provides a kit that includes Compound 1 or a phamectucially acceptable salt thereof. Some of the kits described herein include a label describing a method of administering Compound 1. Some of the kits described herein include a label describing a method of treating transthyretin (TTR) amyloidosis. In some embodiments, the kits described herein include a label describing a method of treating Wild-type transthyretin amyloid cardiomyopathy (ATTR-CM, also called senile systemic amyloidosis). In some embodiments, the kits described herein include a label describing a method of treating familial amyloid cardiomyopathy (ATTR-mCM). In some embodiments, the kits described herein include a label describing a method of treating familial amyloid polyneuropathy (ATTR-PN, also called FAP).

The compositions of the present invention, including but not limited to, compositions comprising Compound 1 in a bottle, jar, vial, ampoule, tube, blister pack, or other container-closure system approved by the Food and Drug Administration (FDA) or other regulatory body, which may provide one or more unit dosages containing Compound 1 or a phamectucially acceptable salt thereof. The package or dispenser may also be accompanied by a notice associated with the container in a form prescribed by a governmental agency regulating the manufacture, use, or sale of pharmaceuticals, the notice indicating approval by the agency. In certain aspects, the kit may include a formulation or composition as described herein, a container closure system including the formulation or one or more dosage units form including the formulation, and a notice or instructions describing a method of use as described herein.

Packaging systems such as blister packs include a thermoformable rigid film or PVC suitable for pharmaceutical packaging and a push through type lid. The lid can include a foil, made up of a primer/aluminum/heat-seal-coating, or may be paper based. A person of skill in the art will readily prepare blister packs comprising Compound 1. Bottle systems described herein can be made in various sizes (e.g., 75 cc, 100 cc, 200 cc, etc), and generally include child resistant closures that can be made from polypropylene. In some embodiments, a pharmaceutical dosage form of Compound 1 is packaged in 75 cc bottles, with a child resistant closure. A person of skill in the art can readily prepare bottle systems described herein.

In some embodiments, the present disclosure provides kits for twice daily dosing. These kits provide one or more unit doses comprising Compound 1 for each administration.

In some embodiments, the total daily dose of Compound 1 is 800 mg, meaning 400 mg are administered at a first dosing, and 400 mg are administered at a second dosing. In some embodiments, two unit doses containing 200 mg of Compound 1 are administered at the first dosing and two unit doses containing 200 mg of Compound 1 are administered at the second dosing. In some embodiments, one unit dose containing 400 mg of Compound 1 is administered at the first dosing and one unit dose containing 400 mg of Compound 1 is administered the second dosing. In some embodiments, the HCl salt form of Compound 1 is administered.

In some embodiments, the total daily dose of Compound 1 is 1,600 mg, meaning 800 mg are administered at a first dosing, and 800 mg are administered at a second dosing. In some embodiments, four unit doses containing 200 mg of Compound 1 are administered at the first dosing and four unit doses containing 200 mg of Compound 1 are administered at the second dosing. In some embodiments, two unit doses containing 400 mg of Compound 1 is administered at the first dosing and two unit doses containing 400 mg of Compound 1 is administered the second dosing. In some embodiments, the HCl salt form of Compound 1 is administered.

IV. Examples

The following examples are offered to illustrate, but not to limit, the claimed invention.

Materials and Methods

The following general materials and methods were used, where indicated, or may be used in the Examples below:

Determination of AG10 Blood Plasma Concentration

Human plasma containing AG10 and the internal standard, AG10-$D_6$, was extracted using protein precipitation and analyzed by a Sciex API4000 LC-MS-MS equipped with an HPLC column. The peak area of the AG10 product ion was measured against the peak area of the AG10-$D_6$ internal standard product ion. Quantitation was performed using a weighted $1/x^2$ linear least squares regression analysis generated from calibration standards prepared on the day of extraction.

Fluorescent Probe Exclusion Assay (FPE)

Occupancy of AG10 in the thyroxine binding pocket of tetrameric TTR is determined by the ability of a fluorescent probe (Probe) to covalently bind to free tetrameric TTR binding sites in serum over a 6 hr reaction time.

Aliquots of each serum sample are plated in 96 well plates. The fluorescence changes ($\lambda_{ex}$=328 nm and $\lambda_{em}$=384 nm) after addition of probe are monitored every 15 min using a fluorescent capable microplate for 6 hr at RT.

Western Blot for Evaluating Stabilization of Tetrameric TTR

Stabilization of the tetramer of TTR by AG10 is determined by comparing the amount of tetrameric TTR protein remaining after acid denaturation for 72 hr to the initial amount of tetrameric TTR protein as determined by densitometric measurement of western blot gels.

Blood plasma samples from the subject are diluted with acidification buffer (sodium acetate, KCl, EDTA, DTT, pH about 4.0) for both the 0 and 72 hour time point. Time 0 hr samples are directly cross-linked with glutaraldehyde, and then quenched. 72 hr samples are incubated at room temperature for 72 hr and then cross-linked and quenched by the same protocol. All samples are then denatured by adding SDS gel loading buffer and boiled prior to gel loading. Each sample is separated in SDS-PAGE gels and analyzed by immunoblotting using anti-TTR antiserum (Polyclonal Rabbit Anti-Human Prealbumin. DAKO Cat #A0002). The density of all TTR bands are quantified using infrared LICOR imaging system or Fluorescence Imaging system and reported. Normalization by IgG band using LICOR 925-32232 or Invitrogen 84546.

In the Experiments, Tables, and Figures discussed in further detail below, nominal times of blood draw are used for all pharmacokinetic and pharmacodynamic data.

Example 1: Preparation of AG10.HCl

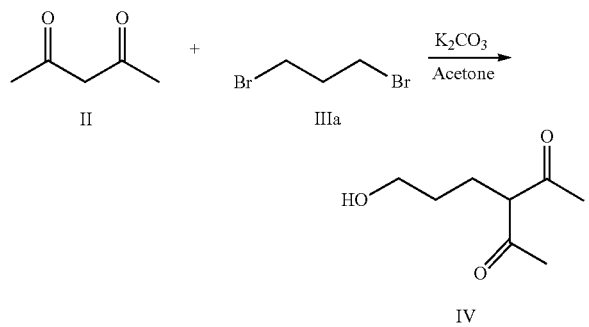

A compound of Formula IIIa (100 g, 495 mmol 1.0 equiv.) was dissolved in acetone (1 L). A compound of Formula II (49.59 g, 495 mmol, 1.0 equiv.) was added to above solution, followed by addition of $K_2CO_3$ (82.14 g, 594.38 mmol, 1.2 equiv.) and KI (41.11 g, 247 mmol, 0.5 equiv.) at room temperature with stirring. The reaction mixture was heated to 60±5° C. and stirred for 40 h at this temperature. The reaction mixture was filtered and then concentrated under reduced pressure to afford a compound of Formula IV (102 g) as viscous orange liquid.

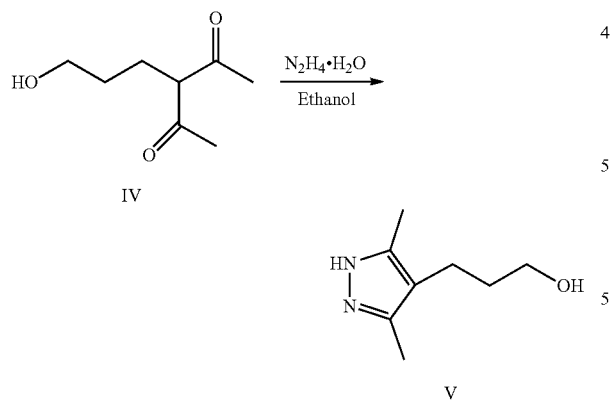

A compound of Formula IV (100 g, 632 mmol, 1.0 equiv.) was dissolved in ethanol (1 L). Hydrazine hydrate (87 g, 1738 mmol, 2.75 equiv.) and conc. HCl (4.6 mL, 0.2 equiv.) were added to above solution. The reaction mixture was heated to 75±5° C. and stirred for 3 h at this temperature. After completion of reaction by TLC (70% ethyl acetate: n-hexane, visible in iodine) and obser-vation of product peak in mass spectrum, the reaction mixture was concentrated under reduce pressure to afford a compound of Formula V (70 g) as a colorless liquid syrup which was used as such for next step.

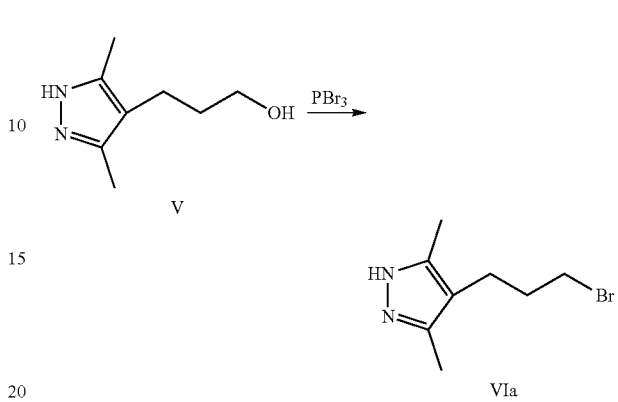

A compound of Formula V (35 g, 227 mmol, 1.0 equiv.) was dissolved in 1, 2-dichloroethane (525 mL). $PBr_3$ (64.67 mL, 681 mmol, 3 equiv.) was added in small portions at room temperature over 30 minutes. The reaction mixture was heated up to 75±5° C. and stirred for 3 h at this temperature. After completion of reaction by TLC (50% ethyl acetate: n-hexane, visible in iodine) and observation of product peak in Mass spectrum, the reaction mixture was diluted with dichloromethane (350 mL) and quenched with saturated solution of $NaHCO_3$ till pH=7 to 8. Both organic and aqueous layers were separated and collected. The organic layer was dried over $MgSO_4$ and filtered. Filtrate was concentrated under reduce pressure to afford a compound of Formula VIa (38 g) as a viscous orange liquid.

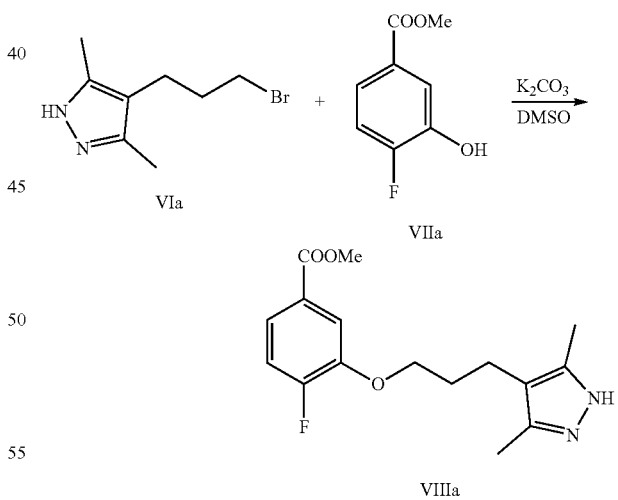

4-(3-Bromopropyl)-3,5-dimethyl-1H-pyrazole hydrobromide (VIa) and DMSO were charged into vessel and agitated at 20±10° C. for 10 minutes. The mixture was then heated to 55±5° C. with stirring. To this mixture was transferred a stirred solution containing 4-fluoro-3-hydroxy-benzoic acid methyl ester (VIIa), potassium carbonate and anhydrous DMSO. The DMSO solution of the alkyl bromide were slowly transferred in order to maintaining an internal temperature of 55.0±5° C. Addition was complete after 6 hours and the mixture was agitated at 55.0±5° C. for an additional hour at 55.0±5° C. The mixture was cooled to 25±5° C. over the course of 30 minutes and water added while maintaining a temperature below 25° C. The mixture was extracted with ethyl acetate and the aqueous layer back extracted with ethyl acetate. The pooled ethyl acetate solutions were washed brine. The combined ethyl acetate washes were concentrated under vacuum to a minimal volume and heptane was added, which precipitates VIIIa. The mixture was heated to 75±5° C. and aged with stirring for 1 hour. The mixture was cooled to 25±5° C. over the course of two hours and the resulting solids collected by filtration. The filter cake was washed with ethyl acetate in heptane (30%). Isolated solids were dried with a nitrogen flow. Solids are charged to vessel and combined with ethyl acetate and heptane. The resulting mixture is heated to 75±5° C. to dissolve solids. The solution was cooled to 25±5° C. over the course of two hours and the resulting solids collected by filtration. The solids were washed with a 30% ethyl acetate/heptane solvent mixture and dried in vacuum oven at 55° C. to give VIIIa in >99.5% purity.

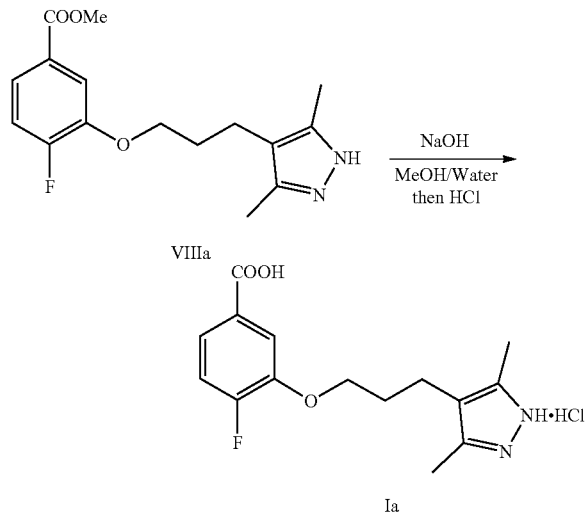

A jacketed glass vessel is charged with compound of formula VIIIa (1.0 equiv.) and methanol. The mixture is cooled with stirring to 10±5° C. and over the course of 20 minutes an aqueous solution of sodium hydroxide (3 equiv.) is charged. The mixture is aged with stirring at 20±5° C. for NLT 2 hours at which point the reaction is complete. Stirring is stopped and water is added. Methanol is then removed by vacuum distillation at an internal temperature of NMT 35° C. The resulting concentrated, clear aqueous solution is cooled to 10° C. and concentrated HCl is added until the pH was lowered to between 1.4-1.6 (pH meter) to precipitate the HCl salt. The solids are collected by filtration, washed with 0.2 N HCl and dried under vacuum at 50° C. to give a compound of Formula Ia in NLT 99.5% purity.

Example 2: Phase 1 Clinical Study

Study AG10-001 was a two-part, randomized, double-blind, placebo-controlled, single- and multiple-ascending dose, first-in-human trial conducted in healthy adult volunteers to evaluate safety, tolerability, PK and PD of AG10 after single and multiple doses. This study was also designed to evaluate the effect of food on the PK of AG10.

Part A was a single ascending dose (SAD) design, where 4 cohorts of 8 healthy men and/or women were randomized to AG10 or matching placebo in a 3:1 overall ratio.

Part B was a multiple ascending dose (MAD) design, where 3 cohorts of 8 healthy men and/or women were randomized to AG10 or its placebo in a 3:1 ratio for 12 days of dosing. In total, 4 cohorts including 8 healthy subjects each (total of 32 subjects, 24 dosed with AG10 HCl and 8 with placebo to match) dosed with ascending doses of 50 mg, 150 mg, 300 mg and 800 mg of blinded study medication completed the SAD portion of the study. One of the SAD cohorts received two 300 mg doses, one under fasted conditions and the other following a high fat test meal after an appropriate washout period. Three cohorts including 8 healthy subjects each (total of 24 subjects, 18 dosed with AG10 HCl and 6 with placebo to match) dosed with 100 mg, 300 mg or 800 mg of blinded study medication every 12 hrs for 12 days completed the MAD portion of the study.

Single Ascending Dose

The PK profiles observed for healthy subjects dosed with 50 mg AG10 HCl (SAD cohort 1), 150 mg AG10 HCl (SAD cohort 2), 300 mg AG10 HCl (SAD cohort 3) and 800 mg AG10 HCl (SAD cohort 4) reveal that AG10 has rapid oral absorption with a mean $T_{max}$ of under one hr and an elimination half-life of around 22-27 hrs. Table 1 lists the geometric means of the PK parameters for SAD Cohorts 1-4. Moreover, as shown in FIG. 1, there is moderate inter-subject variability in PK in SAD Cohorts 1-4, with % CV for $C_{max}$ ranging from 10.0%-41.9% and % CV for $AUC_{inf}$ ranging from 12.5%-40.4%.

TABLE 1

| Geometric Means of PK Parameters for SAD Cohorts 1-4 | | | | | | | |
|---|---|---|---|---|---|---|---|
| Dose (mg) | $T_{1/2}$ (hr) | $T_{max}$ (hr) | $C_{max}$ (µM) | $C_{24}$ (µM) | $AUC_{0-24}$ (hr*µM) | $AUC_{last}$ (hr*µM) | $AUC_{inf}$ (hr*µM) |
| 50 | 25.0 ± 2.91 | 0.891 ± 0.736 | 7.20 ± 0.720 | 1.05 ± 0.130 | 58.9 ± 4.09 | 95.0 ± 11.8 | 97.1 ± 12.1 |
| 150 | 25.1 ± 3.58 | 0.849 ± 0.970 | 11.3 ± 4.76 | 1.78 ± 0.465 | 93.0 ± 16.8 | 166 ± 46.0 | 168 ± 46.8 |
| 300 | 22.0 ± 5.94 | 0.707 ± 0.274 | 15.1 ± 3.60 | 2.19 ± 0.435 | 100 ± 9.76 | 186 ± 73.8 | 191 ± 77.0 |
| 800 | 26.8 ± 8.48 | 0.794 ± 0.258 | 37.8 ± 11.3 | 4.51 ± 0.565 | 176 ± 27.7 | 410 ± 81.7 | 414 ± 87.5 |

Values = Geometric Mean ± SD

Figure 2:
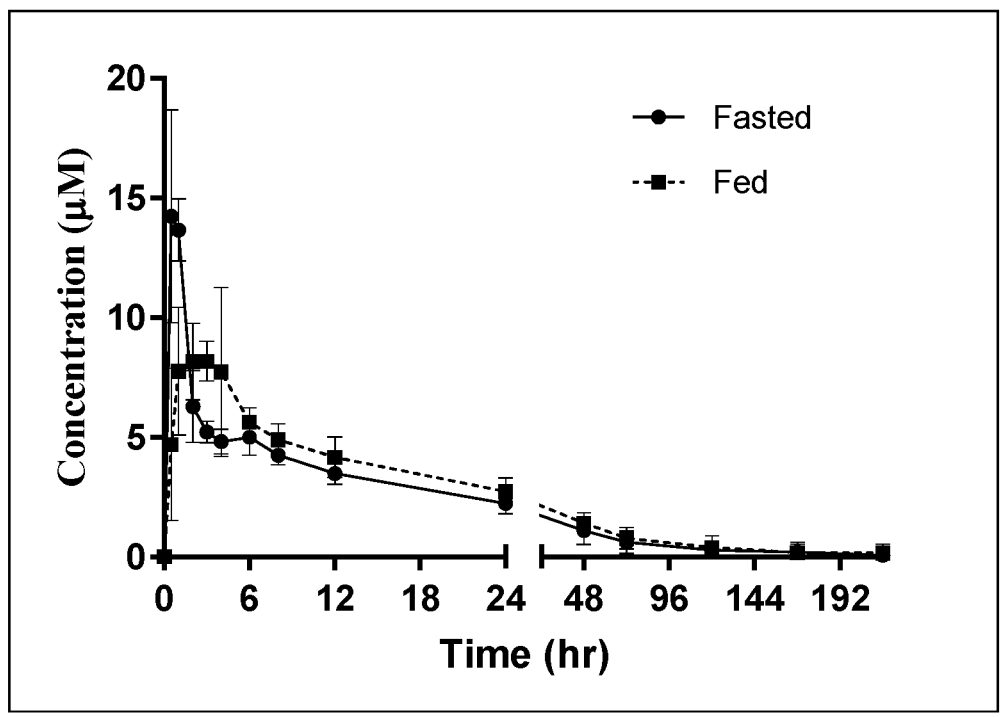
FIG. 2 shows PK profiles of fed vs fasted subjects in single ascending dose Cohort 3 (300 mg oral dose of AG10 HCl).

In addition, as shown in FIG. 2 (cohort 3 shown) the food effect portion of the SAD study revealed minimal food effect on the pharmacokinetics of AG10 with a slight reduction of $C_{max}$ and a slightly longer $T_{max}$ in the fed versus fasted state, but overall no significant change in exposure as defined by $AUC_{0-24}$. PK data for Cohort 3 is shown below in Table 2.

TABLE 2

SAD Cohort 3 Fed versus Fasted PK Parameters

| Condition | $T_{max}$ (hr) | $C_{max}$ (μM) | $C_{24}$ (μPM) | $AUC_{0-24}$ (μM*hr) |
|---|---|---|---|---|
| Fasted | | | | |
| Geom. Mean | 0.707 | 15.1 | 2.19 | 99.6 |
| SD | 0.274 | 3.60 | 0.43 | 9.76 |
| % CV | 38.7 | 23.8 | 19.8 | 9.80 |
| Fed | | | | |
| Geom. Mean | 1.59 | 10.2 | 2.69 | 111 |
| SD | 1.17 | 2.31 | 0.57 | 13.7 |
| % CV | 73.6 | 22.6 | 21.3 | 12.3 |

All data presented as geometric means.

Multiple Ascending Dose

Figure 3:
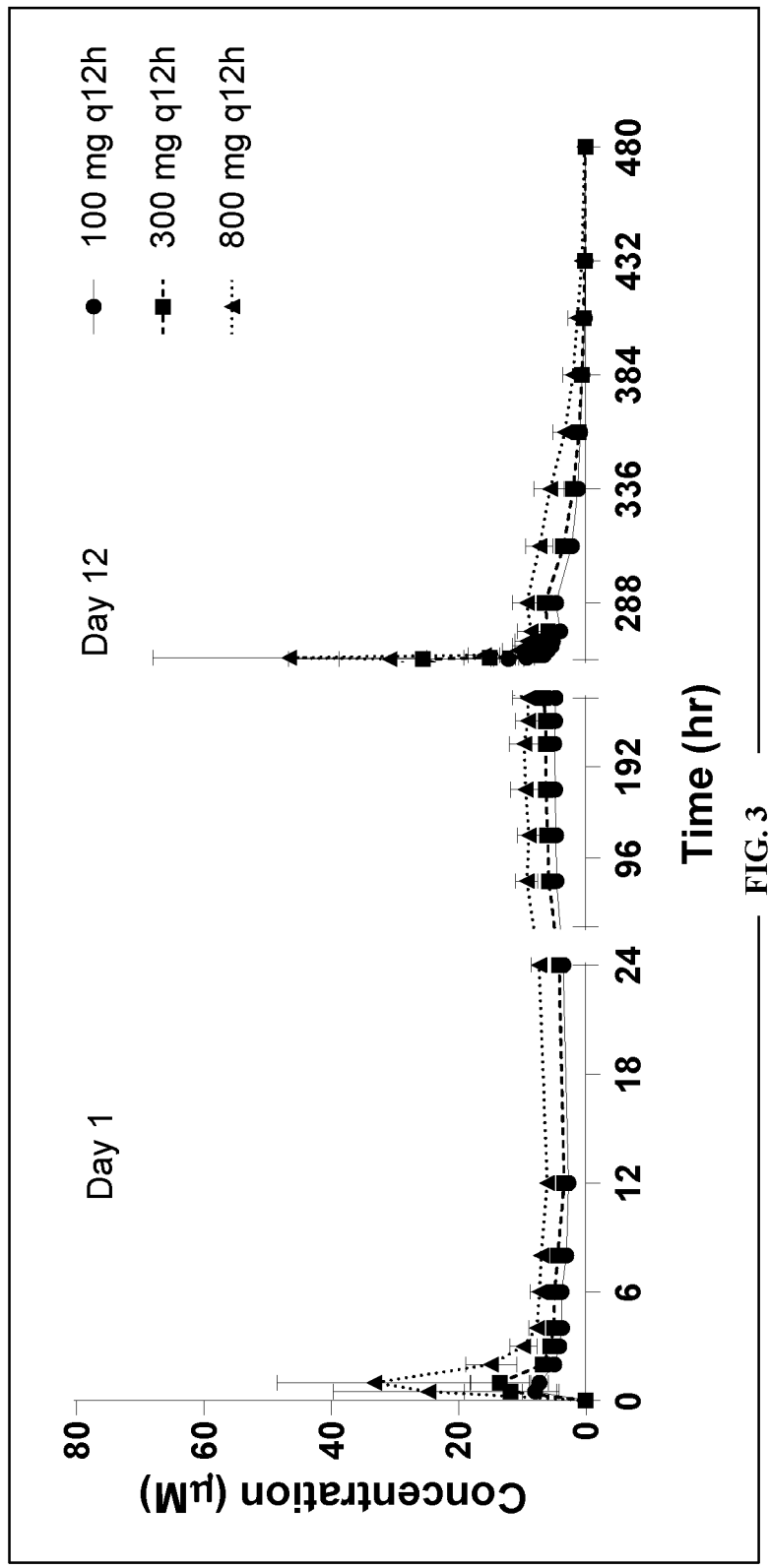
FIG. 3 shows the PK profiles of multiple ascending dose cohorts 1-3 at 100 mg, 300 mg, 800 mg oral doses of AG10 HCl every 12 hours for 12 days.

Pharmacokinetic plots for MAD cohort 1 (healthy subjects dosed with 100 mg AG10 HCl every 12 hr for 12 days), cohort 2 (healthy subjects dosed with 300 mg AG10 HCl every 12 hr for 12 days), and cohort 3 (healthy subjects dosed with 800 mg AG10 HCl every 12 hr for 12 days) are shown in FIG. 3 and PK parameters are listed in Table 3. Even though some inter-subject variability was observed in the $C_{max}$ values in each dose group, $AUC_{0-12}$ values were remarkably similar with % CV values ranging from 8.8%-22.2%. No significant accumulation was observed over 12 days of dosing.

TABLE 3

MAD Cohorts 1-3 PK Parameters

| | | Day 1 | | | Day 12 | | | |
|---|---|---|---|---|---|---|---|---|
| Dose | Statistics | $T_{max}$ (hr) | Cmax (μM) | $AUC_{0-12}$ (μM*hr) | $T_{max}$ (hr) | $C_{max}$ (μM) | $AUC_{0-12}$ (μM*hr) | Accumulation Ratio |
| 100 mg q12 h | Geom. Mean | 0.794 | 8.67 | 46.3 | 0.561 | 12.12 | 70.3 | 1.52 |
| | SD | 0.585 | 2.97 | 5.96 | 0.204 | 2.18 | 6.19 | |
| | % CV | 73.6 | 34.3 | 12.9 | 36.4 | 18.0 | 8.80 | |
| 300 mg q12 h | Geom. Mean | 0.707 | 14.3 | 65.2 | 0.561 | 23.5 | 97.7 | 1.50 |
| | SD | 0.274 | 6.20 | 11.7 | 0.204 | 12.81 | 9.05 | |
| | % CV | 38.7 | 43.4 | 18.0 | 36.4 | 54.6 | 9.26 | |
| 800 mg q12 h | Geom Mean | 0.794 | 31.8 | 120 | 0.891 | 42.5 | 159 | 1.32 |
| | SD | 0.258 | 16.3 | 20.4 | 0.204 | 20.8 | 35.3 | |
| | % CV | 32.5 | 51.4 | 17.0 | 22.9 | 49.0 | 22.2 | |

AG10 Pharmacodynamics

Pharmacodynamic (PD) properties of AG10 have been assessed by use of the Fluorescent Probe Exclusion (FPE) and Western blot assays (as described above), both of which are established assays of TTR target engagement and TTR stabilization.

Figure 4:
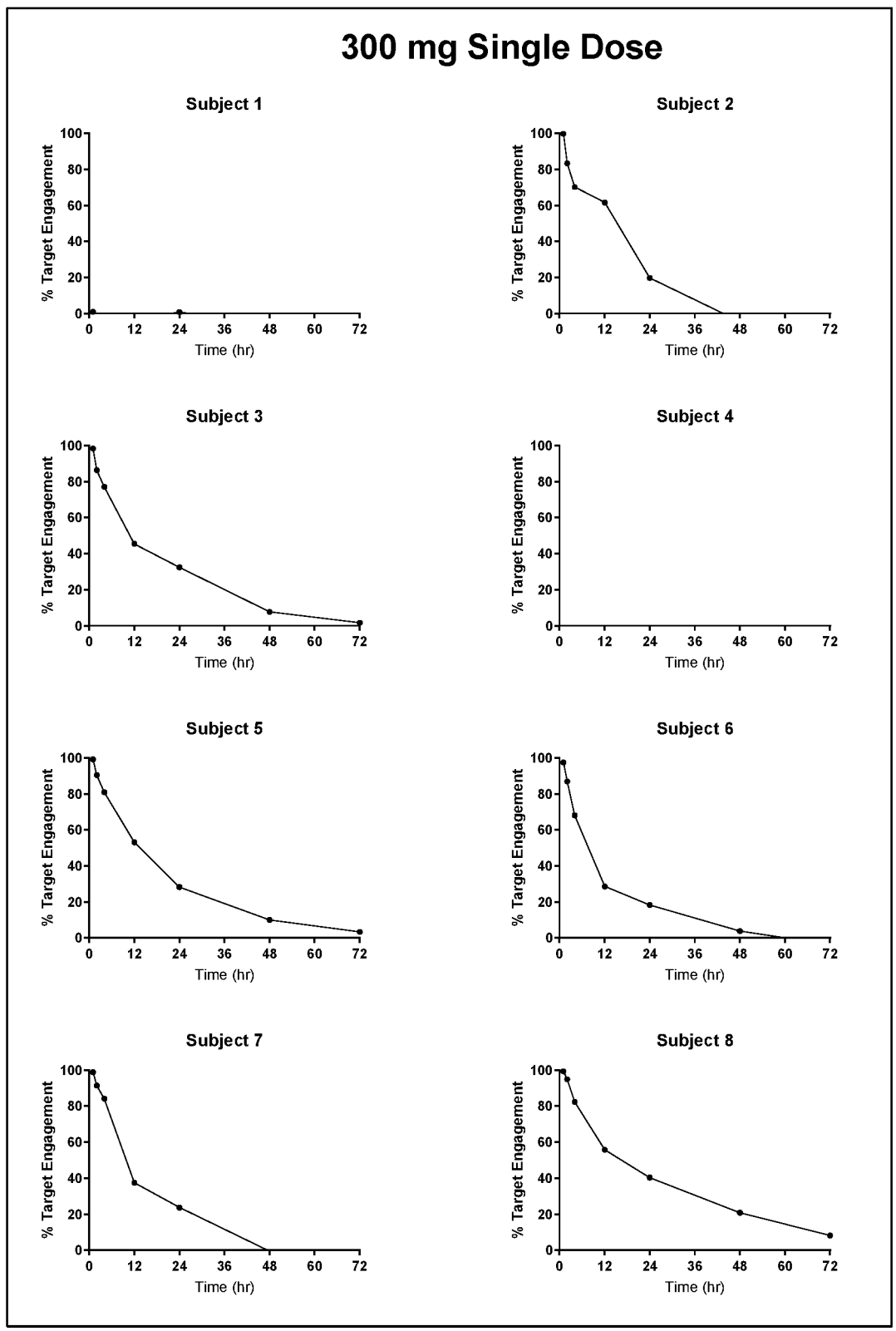
FIG. 4 shows Fluorescent Probe Exclusion (FPE) assay time courses of single ascending dose cohort 3 (300 mg oral AG10 HCl) demonstrating percent target engagement as a function of time. In this cohort, 6 subjects are administered Compound 1, while 2 subjects are administered a placebo. The placebo group are subjects 1 and 4.
Figure 5:
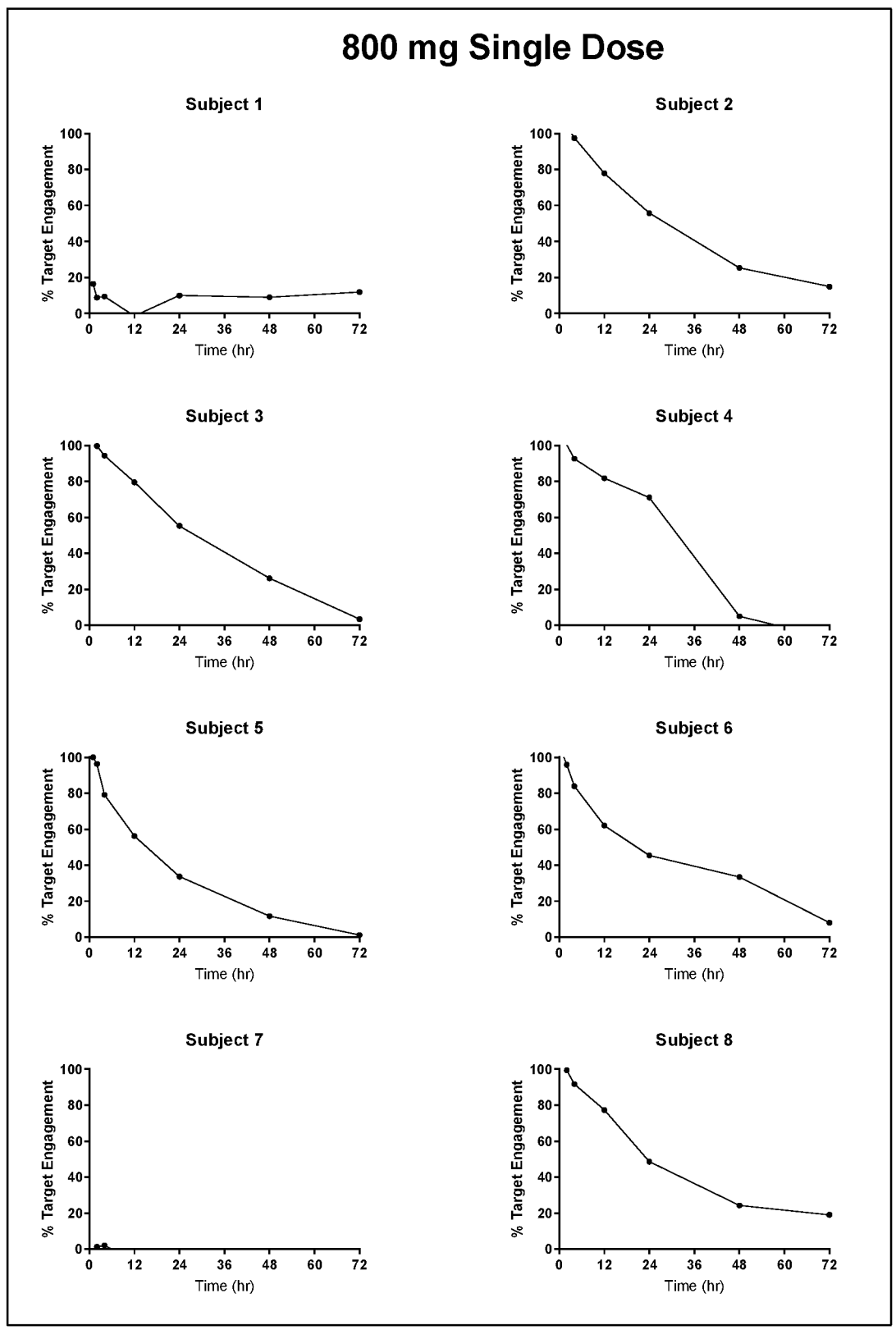
FIG. 5 shows FPE assay time courses of single ascending dose cohort 4 (800 mg oral AG10 HCl) demonstrating percent target engagement as a function of time. In this cohort, 6 subjects are administered Compound 1, while 2 subjects are administered a placebo. The placebo group are subjects 1 and 7.
Figure 6:
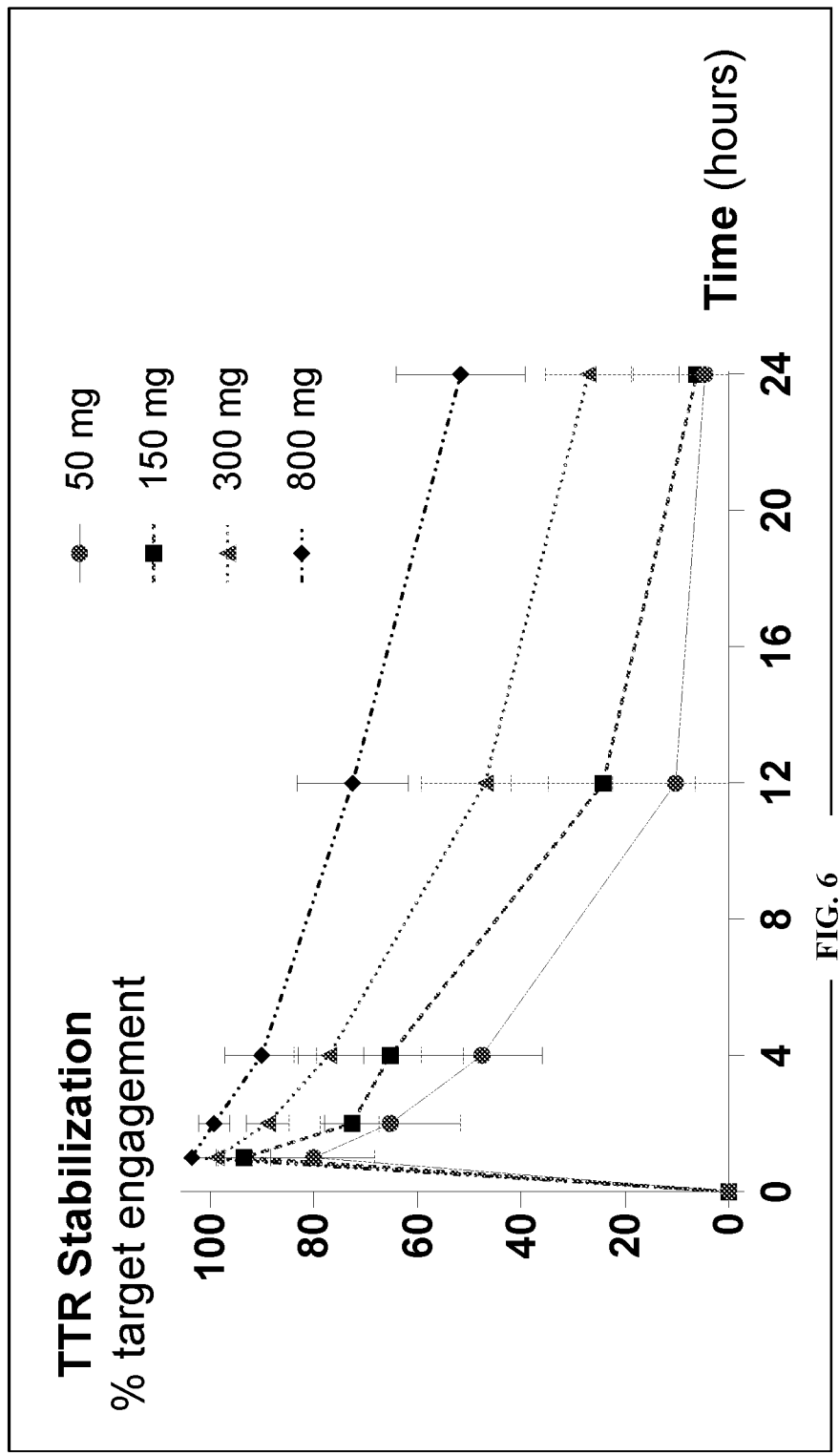
FIG. 6 shows the average percent target engagement for each single ascending dose cohort as a function of time.
Figure 7A:
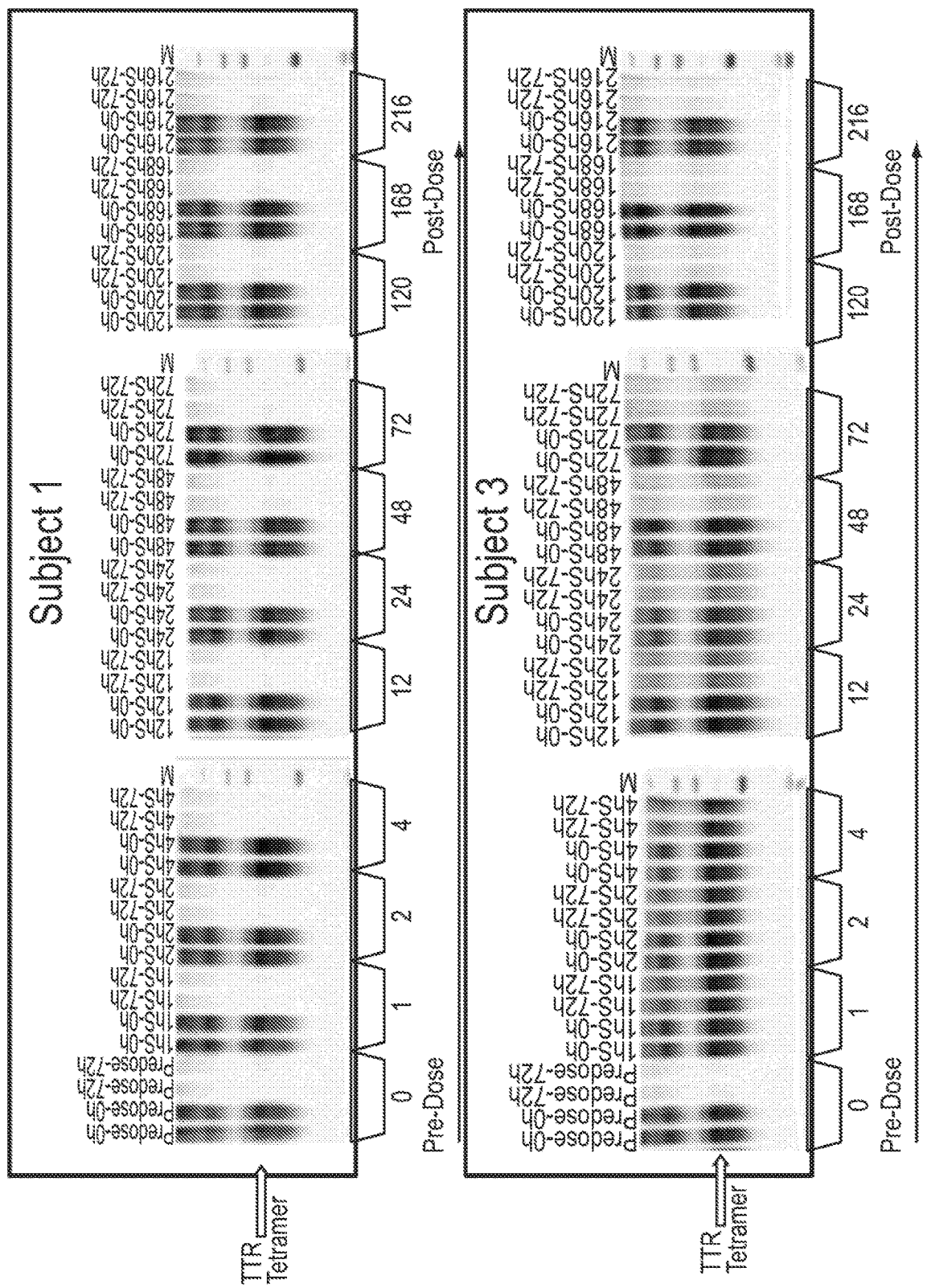
FIGS. 7A-7D show western blot data for single ascending dose cohort 3 (300 mg AG10 HCl). The arrow on the side of the gel indicates the position of the TTR tetramer based on Molecular Weight and recognition by a TTR specific antibody.
Figure 7B:
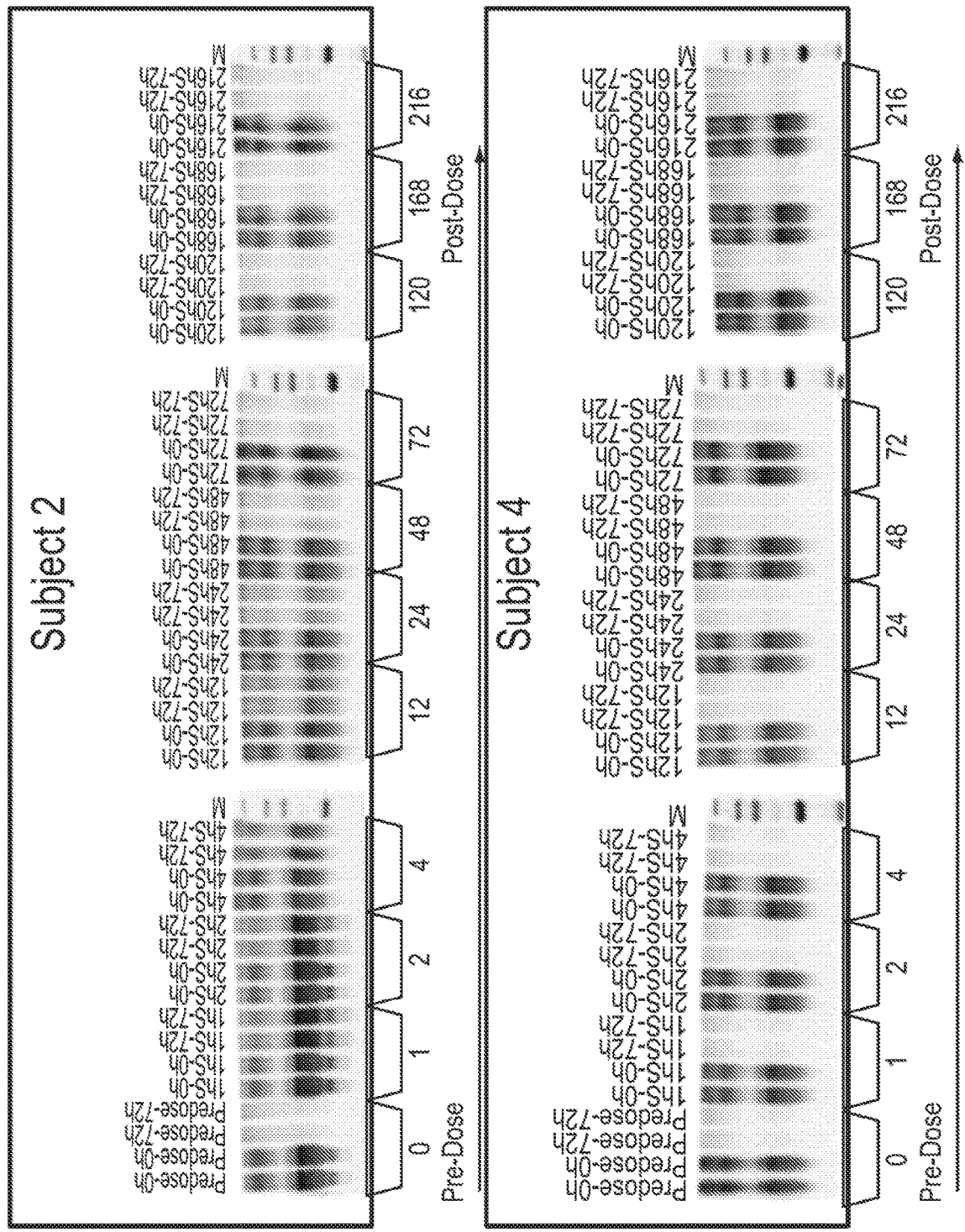
Figure 7C:
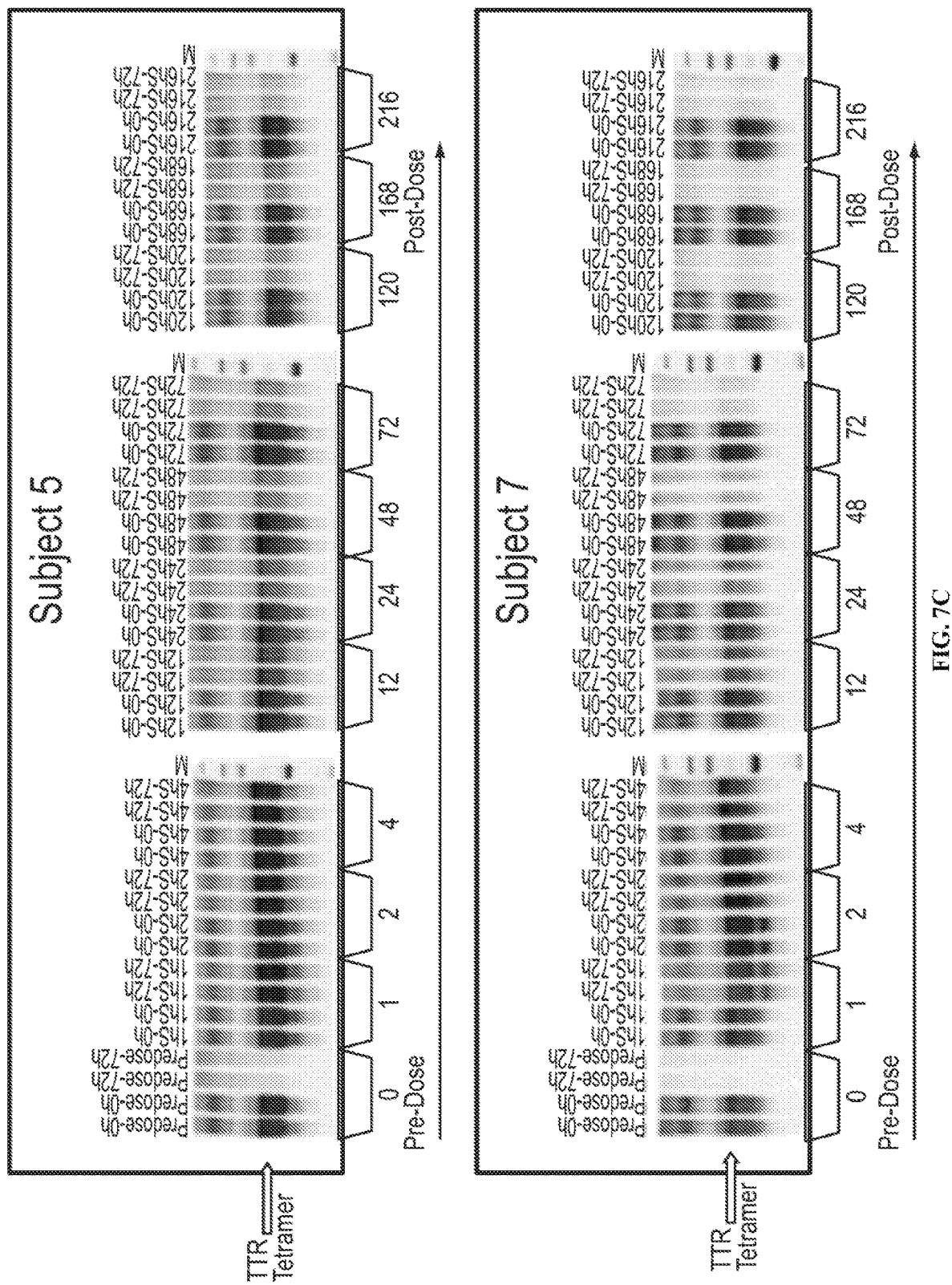
Figure 7D:
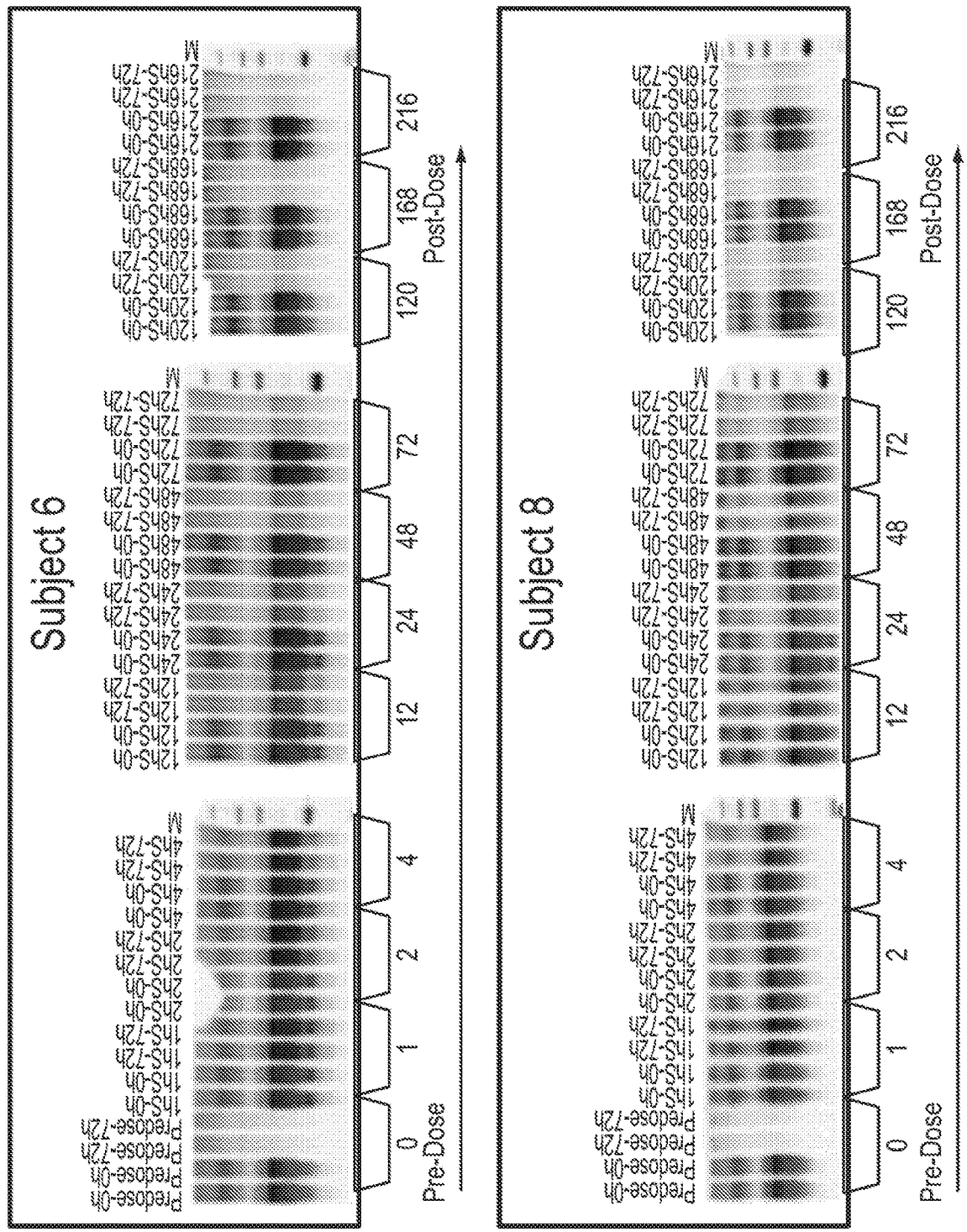
Figure 8:
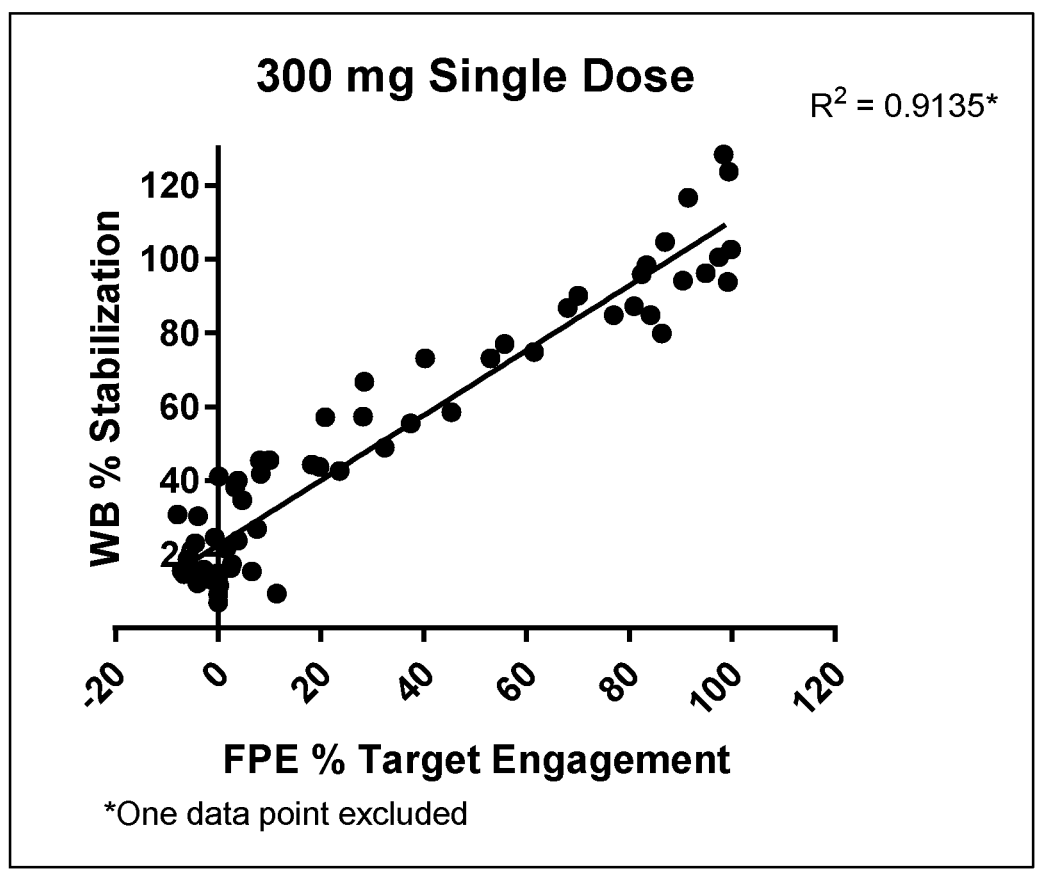
FIG. 8 shows the correlation between western blot data and FPE data for single ascending dose cohort 3 (300 mg oral AG10 HCl).

As shown in FIG. 4 and FIG. 5 data from the FPE assay confirms target engagement at a single dose of 300 mg and 800 mg, with complete stabilization of TTR at peak concentrations and sustained stabilization up to 12 hrs, ranging from 29% to 62% at 300 mg and from 56% to 82% at 800 mg. FIG. 6 shows the average percent target engagement for each single ascending dose cohort as a function of time; this data demonstrates that escalating doses increased stabilization. Similarly, the Western blot assay (FIGS. 7A and 7B) confirms complete stabilization of TTR at peak concentrations and sustained stabilization up to 12 hr at a single dose of 300 mg of AG10 HCl. The results of the FPE and Western blot assays for SAD cohort 3 correlate well with an $R^2$ coefficient of >0.9 (FIG. 8). Both measures of pharmacologic activity are well correlated with each other.

Figure 9:
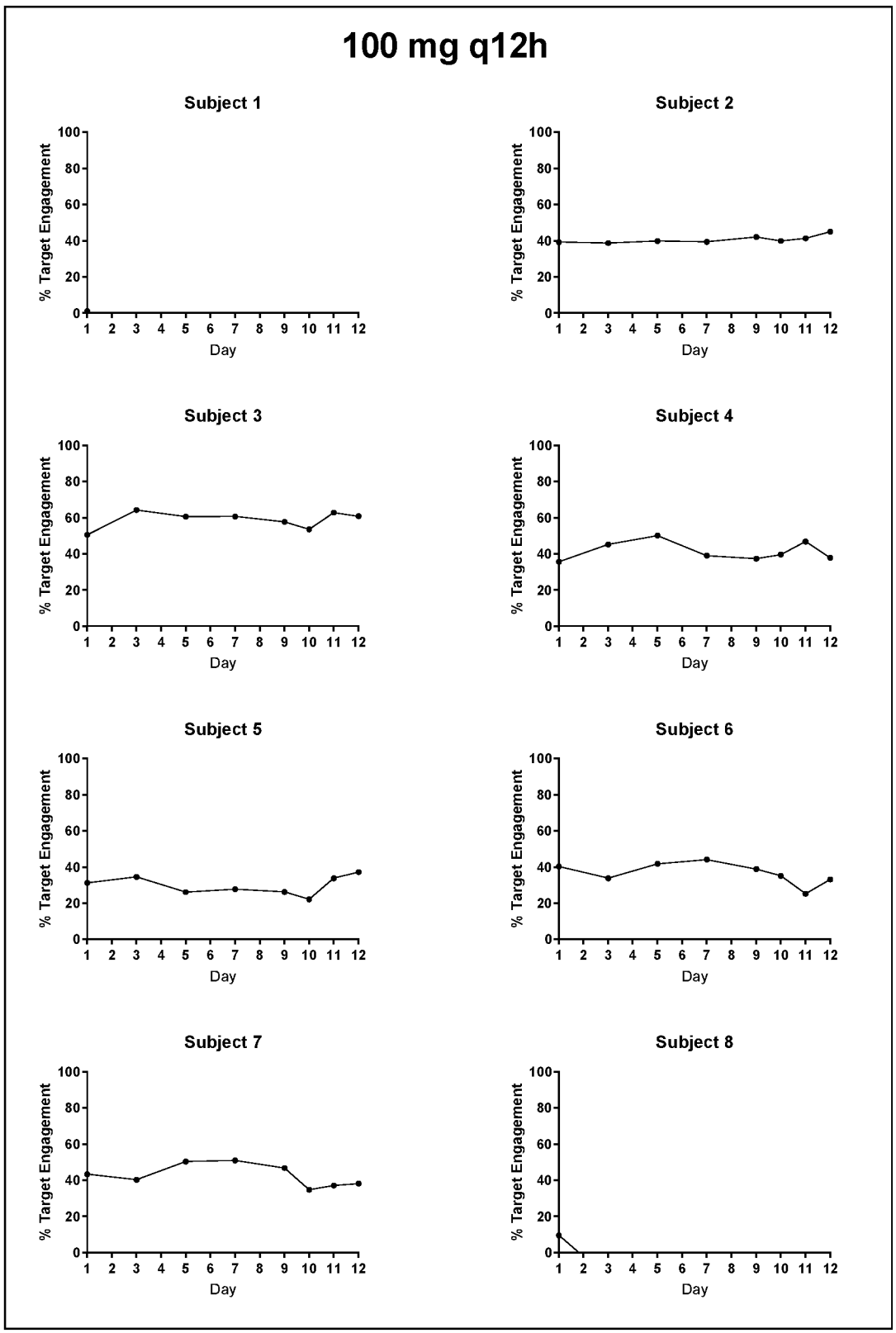
FIG. 9 shows FPE assay time courses for multiple ascending dose cohort 1 (100 mg oral AG10 HCl q12h) through 12 days. In this cohort, 6 subjects are administered Compound 1, while 2 subjects are administered a placebo. The placebo group are subjects 1 and 8.
Figure 10:
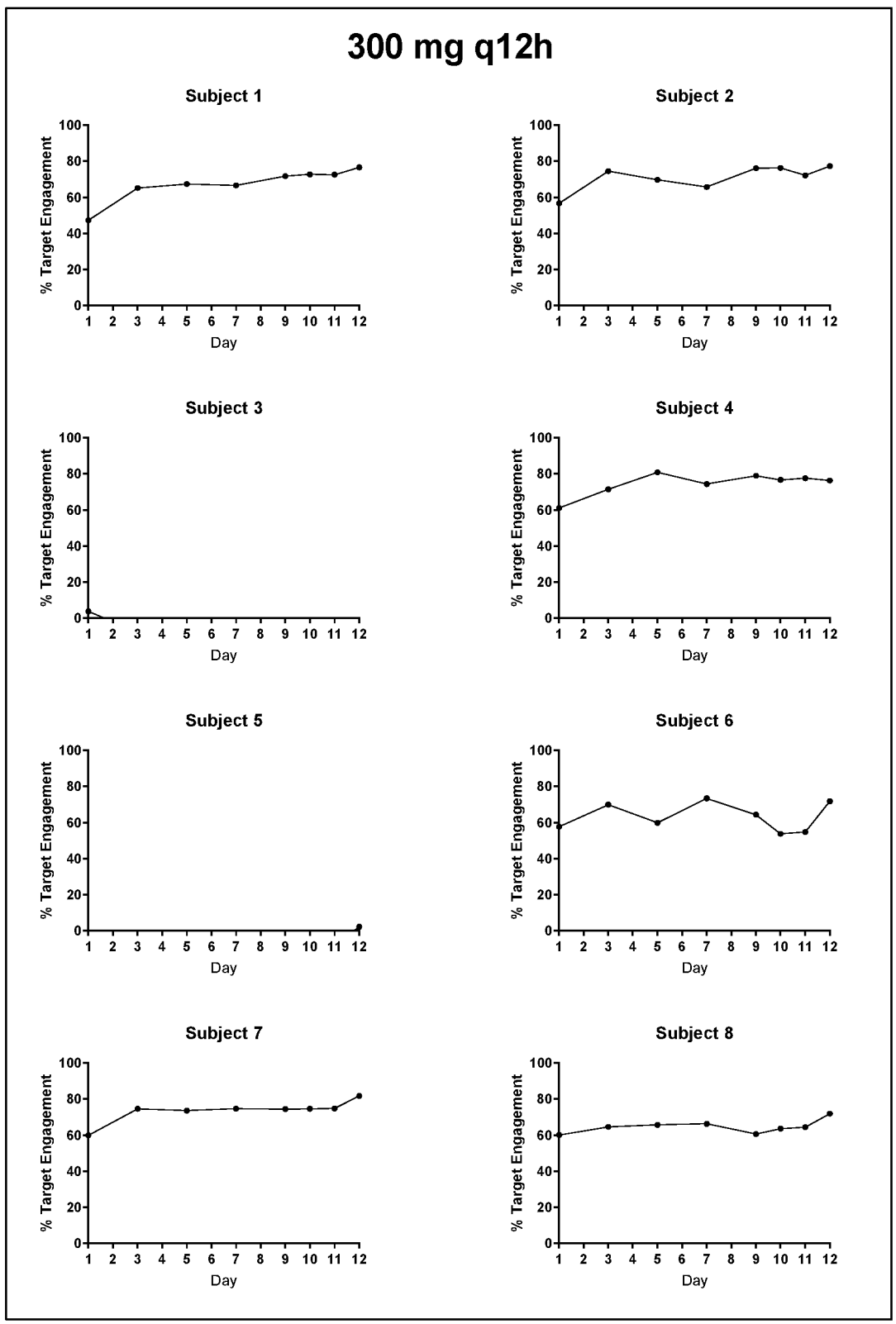
FIG. 10 shows FPE assay time courses for multiple ascending dose cohort 2 (300 mg oral AG10 HCl q12h) through 12 days. In this cohort, 6 subjects are administered Compound 1, while 2 subjects are administered a placebo. The placebo group are subjects 3 and 5.
Figure 11:
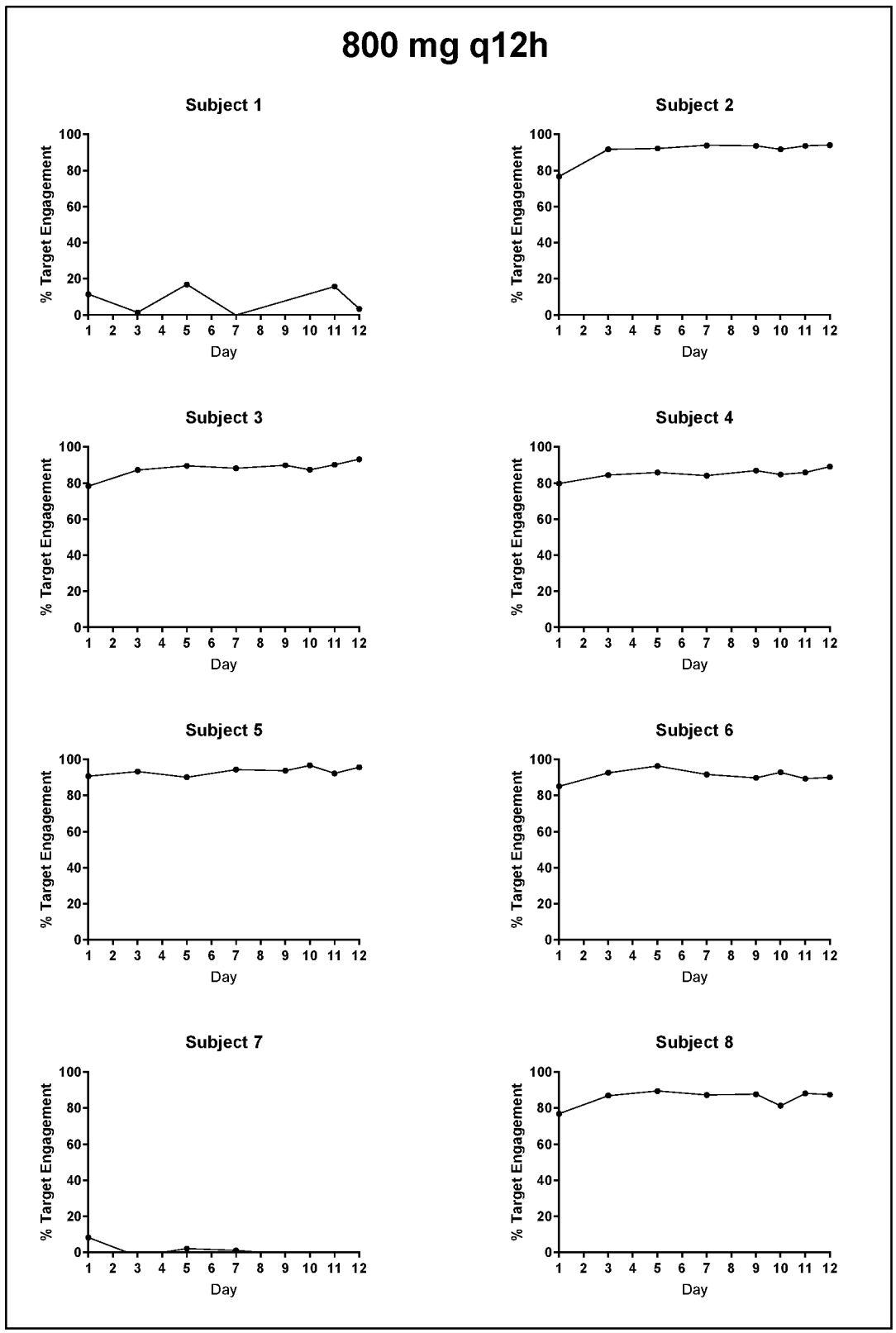
FIG. 11 shows FPE assay time courses for multiple ascending dose cohort 3 (800 mg oral AG10 HCl q12h) through 12 days. In this cohort, 6 subjects are administered Compound 1, while 2 subjects are administered a placebo. The placebo group are subjects 1 and 7.
Figure 12:
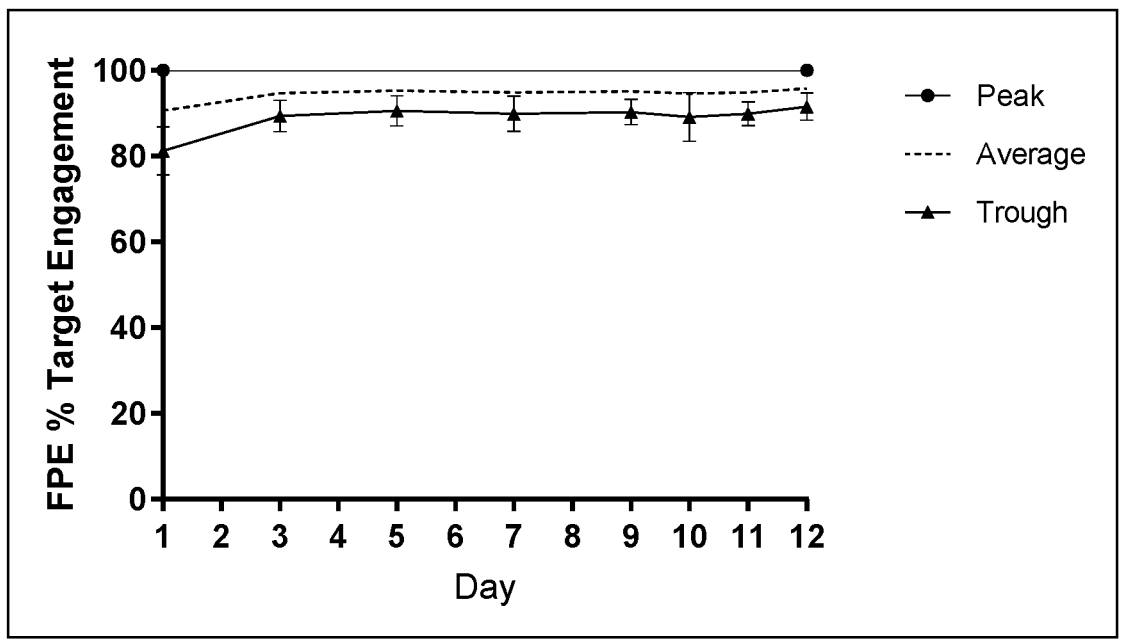
FIG. 12 shows the peak, average, and trough percent target engagement for cohort 3 (800 mg oral AG10 HCl q12h) through 12 days using the FPE assay.

In addition, as shown in FIG. 9, FIG. 10 and FIG. 11 after 12 consecutive days of dosing of AG10 HCl, 100 mg q12h and, 300 mg q12h, and 800 mg q12h, data from the FPE assay confirm sustained target engagement at steady state with mean stabilization of TTR at the 12 hr post-dose timepoint on the last day of dosing ranging from 33% at the 100 mg q12h dose to 89% at the 800 mg q12h dose. FIG. 12 shows the peak, average, and trough percent % TTR target engagement over 12 days of cohort 800 mg q12h dosing with AG10 HCl.

Figure 13:
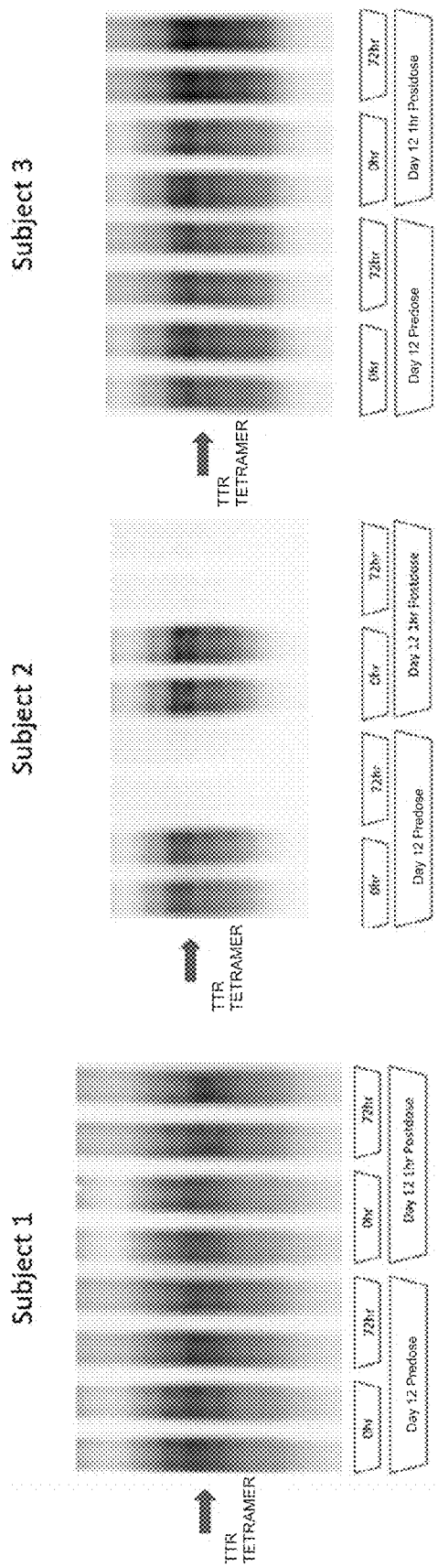
FIG. 13 shows western blot data for multiple ascending dose cohort 3 (800 mg oral AG10 HCl q12h). The arrow on the side of the gel indicates the position of the TTR tetramer based on Molecular Weight and recognition by a TTR specific antibody. Subjects 1 and 3 received AG10, while subject 2 received placebo.

FIG. 13 shows TTR western blot from three subjects in Cohort 3 treated with 800 mg AG10 HCl q12h. Subjects 1 and 3 were dosed with AG10, Subject 2 was dosed with placebo. Lanes labeled 0 hr at day 12 predose contain samples at trough levels of AG10 collected from subjects following 11 days of dosing (22 doses total). Lanes labeled day 12 post dose show samples collected at peak levels following the $23^{rd}$ dose of AG10. Acidification over a 72h period, followed by crosslinking, SDS-PAGE and immunoblotting, as described supra, is used to detect stabilization of tetrameric TTR protein. Subject 2 shows no remaining TTR tetramer as detected by this experimental protocol. In contrast, Subjects 1 and 3 show full stabilization of tetrameric TTR at both trough and peak levels of AG10.

Figure 14:
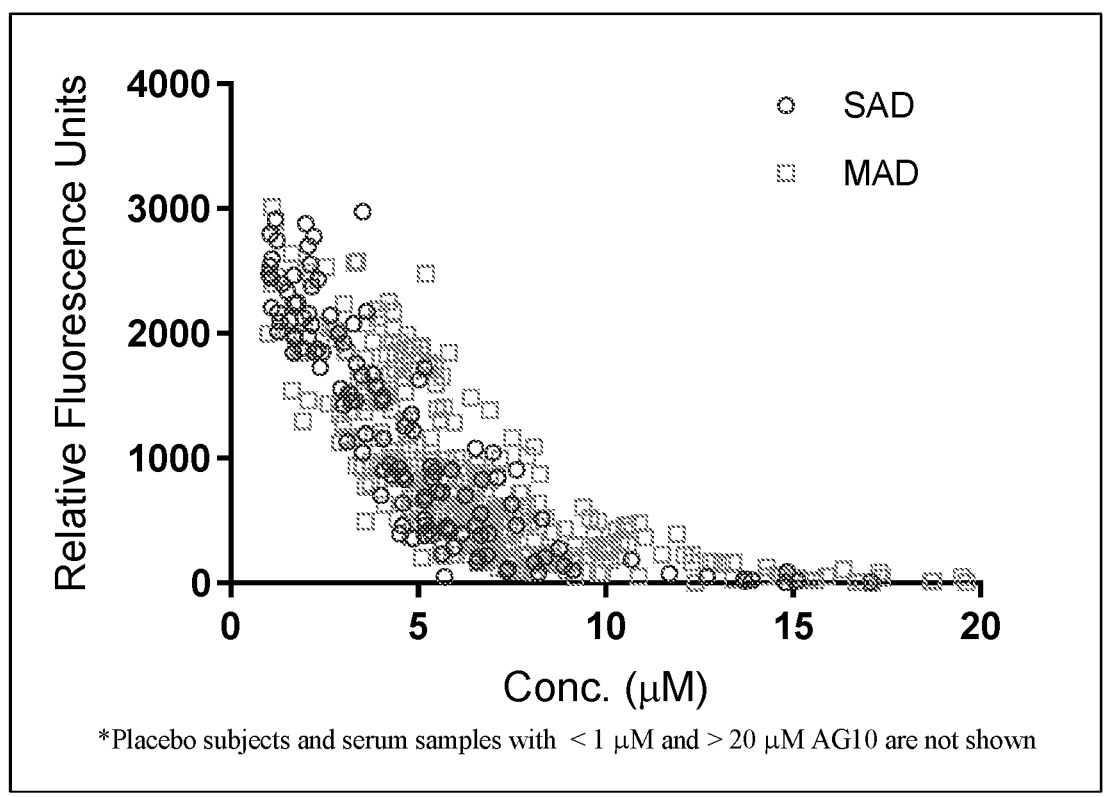
FIG. 14 shows aggregated pharmacokinetic and pharmacodynamic data from the single ascending dose and multiple ascending dose cohorts, there is a predictable dose-responsive PD effect.

The aggregate PK-PD data from the SAD and MAD cohorts shown in FIG. 14 demonstrate predictable and dose-responsive PD effect of AG10 as measured by the FPE assay in human subjects dosed with AG10.

SUMMARY

The data provided herein for AG10 confirm target engagement with complete stabilization of TTR at peak concentrations after both single and multiple doses with sustained stabilization up to 12 hrs.

Example 3: Planned Phase 2 Clinical Study

The Phase 2 study, is planned as a randomized, multicenter, double-blind, parallel group, placebo-controlled, dose-ranging study to evaluate the safety, tolerability, PK and PD of AG10 in patients with ATTR-CM who are on a background of stable heart failure therapy. Screening and randomization will be followed by a 28-day blinded, placebo-controlled treatment period. Approximately 45 subjects are planned to enroll in the Phase 2 study. The synopsis for the Phase 2 study is provided in Table 4.

TABLE 4

Synopsis for Phase 2 Study
CLINICAL STUDY SYNOPSIS: Study AG10

| | |
|---|---|
| Methodology | This prospective, randomized, multicenter, double-blind, parallel group, placebo-controlled, dose-ranging study will evaluate the safety, tolerability, PK and PD of AG10 compared to placebo administered on a background of stable heart failure therapy. Screening and randomization will be followed by a 28-day blinded, placebo-controlled treatment period. |
| Number of Patients | Approximately 45 |
| Test Product, Dosage, and Mode of Administration | AG10 HCl, 400 and 800 mg twice daily, oral administration |
| Duration of Study and Treatment | Study duration: Total of 58 days (Day 1 through the last treatment taken on Day 28), followed by a 30-day follow-up visit. In addition, there will be a 28-day Screening period. Treatment duration: 28 days of dosing |
| Reference Therapy, Dosage, and Mode of Administration | Placebo tablets matching AG10 HCl twice daily, oral administration |
| Pharmacokinetic/ Pharmacodynamic Sampling Measures | PK blood samples will be collected on Days 1, 14, 28. PD blood samples will be collected on Days 1, 14 and 28. |

Example 4: Enthalpy-Driven Stabilization of Transthyretin by AG10 Mimics a Naturally Occurring Generic Variation that Protects from Transthyretin Amyloidosis The following example describes the correlation between enthalpic binding of AG10 and enhanced potency in stabilizing multi-protein complexes.

Materials & Methods

Isothermal Titration Calorimetry (ITC). Binding experiments were performed using MicroCal PEAQ-ITC at 25° C. A solution of ligand (25 µM in PBS pH 7.4, 100 mM KCl, 1 mM EDTA, 2.5% DMSO) was prepared and titrated into an ITC cell containing 2 µM of TTR in an identical buffer. 19 injections of ligand (2.0 µL each) were injected into the ITC cell (at 25° C.) to the point that TTR was fully saturated with ligand. Calorimetric data were plotted and fitted using the standard single-site binding model. For control, we tested the enthalpy change caused by titrating bank DMSO in buffer into TTR and the resulting binding enthalpies was <0.4 kcal/mol. We also used ITC to titrate tafamidis and AG10 against human serum albumin (HSA). The $K_d$ value for tafamidis (2.3 µM) was similar to what has been reported earlier ($K_d$=2.5 µM; EMA Assesment Report EMA/729083/2011). The binding affinity of AG10 was calculated around 8 µM, which also fits with our data in FIG. 20 (where AG10 has lower binding to albumin compared to tafamidis).

FPE assay for binding TTR in buffer and human or dog serum. The binding affinity and selectivity of AG10 and other stabilizers to TTR in buffer and serum was determined by their ability to compete with the binding of a fluorescent probe exclusion (FPE probe) binding to TTRin buffer and human serum. The FPE probe is a thioester TTR ligand that is not fluorescent by itself, however upon binding to the T4 binding site of TTR it covalently modifies lysine 15 (K15), creating a fluorescent conjugate. Ligands that bind to the T4 site of TTR will decrease FPE probe binding as observed by lower fluorescence. The FPE assay was also adapted for use with dog serum. FPE with TTR in buffer: An aliquot of 98 µL of TTR in PBS (pH 7.4, final concentration: 2.5 µM) was mixed with 1 µL of test compounds (2.5 µM) and 1 µL of FPE probe (0.18 mM stock solution in DMSO: final concentration: 1.8 µM). The change in fluorescence ($\lambda_{ex}$=328 nm and $\lambda_{em}$=384 nm) were monitored using a microplate spectrophotometer reader (SpectraMax M5) for 6 hr at rt. FPE with TTR in human and dog serumr: An aliquot of 98 µL of pooled human serum (prepared from human male AB plasma, Sigma; catalog no. H4522; TTR concentration 5 µM) or dog serum (Innovative Research, catalog no.: IBG-SER; TTR concentration 4.6 µM) was mixed with 1 µL of test compounds [All compounds were prepared as 10 mM stock solutions in DMSO and diluted accordingly with DMSO (final concentrations in serum were: AG10 10 µM; diflunisal 200 µM; tafamidis 20 µM; tolcapone 20 µM)] and 1 µL of FPE probe (0.36 mM stock solution in DMSO: final concentration: 3.6 µM). In the case of dog serum (after oral treatment with AG10), 1 µL of FPE probe and 1 µL of DMSO were added to each well and mixed with 98 µL of the appropriate dog serum sample. The change in fluorescence ($\lambda_{ex}$=328 nm and $\lambda_{em}$=384 nm) were monitored using a microplate spectrophotometer reader (SpectraMax M5) for 6 hr at rt.

Stability studies of TTR in serum by immunoblotting. Western blotting was performed as reported earlier. All compounds were prepared as 10 mM stock solutions in DMSO and diluted accordingly with DMSO (final concentrations in serum were: AG10 10 µM; diflunisal 200 µM; tafamidis 20 µM; tolcapone 20 µM). 2 µL of each compound was added to 98 µL of human serum (TTR concentration 5 µM). The samples were incubated at 37° C. for 2 hr, and then 10 µL of the samples were diluted 1:10 with acidification buffer (pH 4.0, 100 mM sodium acetate, 100 mM KCl, 1 mM EDTA, 1 mM DTT). The Western blot assay was also performed in Urea buffer (pH 7.4) as reported earlier. The samples were incubated at room temperature for 72 hr, cross-linked with glutaraldehyde (final concentration of 2.5%) for 5 min, and then quenched with 10 µL of 7% sodium borohydride solution in 0.1 M NaOH. All samples were denatured by adding 100 µL SDS gel loading buffer and boiled for 5 min. 10 µL of each sample was separated in 12% SDS-PAGE gel and analyzed by immunoblotting using anti-TTR antiserum (DAKO A0002, 1:10,000 dilution for human serum and 1:2,000 for dog serum). The combined intensity of TTR bands (TTR tetramer and tetramer bound to RBP) was quantified by using an Odyssey IR imaging system (LI-COR Bioscience) and reported as percentage of TTR tetramer relative to TTR tetramer density of DMSO control at 0 hr (considered 100% stabilization) and 72 hr (ranges between 10% and 35% TTR remaining). The percentage tetramer stabilization is calculated as 100×[(tetramer and tetramer+RBP density, 72 hr)/(tetramer and tetramer+RBP density of DMSO, 0 hr)].

In silico structural and modeling studies. The analyses of the crystal structures of TTR were carried out on four TTR crystal structures obtained from the RCSB PDB site. Biological assemblies of TTR tetramers were constructed using the X-ray crystallographic unit cellinformation given in the pdb files. When multiple models are suggested, the first choice model was used. The initial geometries of the AG10 and its four derivatives (1, 2, 3, and 4) built with Molden[38] were used and geometry optimizations were carried out at the hybrid density functional B3LYP level with 6-311+G(d) basis set using Gaussian'09 program package (Wallingford, Conn., USA: Gaussian, Inc., 2009). The Frequency calculations on the optimized geometries were carried out to ensure they have no imaginary frequencies. Dock 6 program was used for the docking experiments. The crystal structure of the V122I mutant TTR complex with AG10 (pdb id: 4HIQ) was used as the receptor. Tetrameric TTR was built using the crystallographic data, solvent and other heteroatoms were removed and one large docking grid was selected including the T4 binding sites. For all the docking experiments, the same receptor and the grid were used. The flexible ligand docking was carried out to allow the rotation around the torsion angles. UCSF Chimera package was used in visualization and analyses of the 3D structures.

Binding of AG10 and tafamidis to human serum albumin. Test compounds (AG10 or tafamidis; both at 30 μM) were incubated with human serum albumin (HSA; 600 μM; albumin from human serum; Sigma Aldrich, catalog no.: A3782) in assay buffer (10 mM sodium phosphate, 100 mM KCl, and 1 mM EDTA, pH 7.6) for 1 hr at 37° C. 500 μL of a solution of HAS and AG10 or tafamidis mixture in assay buffer was subjected to gel filtration on PD Minitrap G25 columns (GE Life Sciences, catalog no. 45-001-529) by gravity and the fractions containing HSA were identified by NanoDrop™. The concentration of HSA (i.e. concentration at time zero) was also determined using NanoDrop™ (based on calibration curves of known HAS concentrations). HSA concentration was 351 μM for the tafamidis sample and 345 μM for AG10 sample. The concentration of test compounds in these fractions (i.e. conc. at time zero) was evaluated using HPLC (based on calibration curves of known concentration of test compounds). 500 μL of each HSA/test compound samples was then added to a Slide-A-Lyzer Dialysis Cassette G2 (3.5K MWCO, Thermo Scientific, catalog no. PI87722). The dialysis Cassettes were placed in 100 ml of assay buffer and stirred at room temperature. After 24 hr, the samples were removed from dialysis cassette and the volume was measured. The concentration of HAS and test compounds were determined using NanoDrop™ and HPLC as described above.

Dialysis of AG10:TTR complex. AG10 (10 μM) was incubated with human wild-type TTR (5 μM; purified from human plasma; Sigma Aldrich, catalog no. P1742) in assay buffer (10 mM sodium phosphate, 100 mM KCl, and 1 mM EDTA, pH 7.6) for 1 hr at 37° C. 500 μL of each AG10/TTR solution was then added to a Slide-A-Lyzer Dialysis cassette G2. The dialysis cassettes were placed in 100 mL of assay buffer and stirred at room temperature. Samples from the dialysis buffer were taken at different time points (0, 0.5, 1, 2, 6, and 24 hr). After 24 hr, the samples were removed from dialysis cassette and the volume was measured and results normalized. The concentration of TTR and AG10 obtained from the assay buffer were determined using NanoDrop™ and LCMS, respectively.

Selectivity of AG10 and tafamidis to TTR compared to other serum proteins. The FPE assay was modified and performed with purified human TTRwt (5 μM). Other serum proteins were added either individually or in combination [fibrinogen (5 μM), albumin (600 μM), IgG (70 μM), transferrin (25 μM)] to the TTR and FPE mixture and the fluorescence was monitored for 6 hr as described above. The percentage of FPE probe binding to TTR in the presence of serum proteins measured after 3 hr of incubation was used to calculate % TTR occupancy.

7-day repeat oral dosing of AG10 to dogs. 16 Male (M) and 16 female (F) beagle dogs, separated into four treatment groups and orally dosed by gavage with vehicle (6M/6F at 0 mg/kg) or AG10 in 0.5% methylcellulose formulation (2M/2F at 50 mg/kg, 2M/2F at 100 mg/kg, and 6M/6F at 200 mg/kg) for a total of 32 dogs. Blood (approximately 1.5 mL) was collected from a jugular vein into serum separator tubes on study day 1 (predose D1), pre-dose study day 7 (predose D7), and at 1 hr post-dose study day 7 (postdose D7). These serum samples were analyzed for their TTR occupancy using the FPE assay described above.

Single oral doses of AG10 to dogs to determine an exposure-effect (PK-PD) relationship with respect to binding to and stabilization of TTR. 4 Male and 4 female beagle dogs, separated into two treatment groups (n=2/sex/group) for a total of 8 dogs were evaluated to acquire simultaneous pharmacokinetic (PK) and pharmacodynamic (PD) data for AG10 binding to and stabilization of TTR. Each animal received a single oral gavage (PO) of AG10 at a single dose of either 5 or 20 mg/kg in 0.5% methylcellulose. Blood was collected and analyzed pre-dose and at 2, 4, 6, 8, 12 and 24 hr post-dose. The concentration of AG10 in these serum samples was analyzed by LCMS and the TTR occupancy by the FPE assay.

Statistical Analysis. All results are expressed as mean±SD. All statistical analysis was performed with GraphPad PRISM software. The significance of the differences were measured by one-way ANOVA followed by Tukey's multiple comparison test (n.s., not significant; *$p \leq 0.05$; $p \leq 0.01$; *$p \leq 0.001$).

Chemistry. General. All reactions were carried out under argon atmosphere using dry solvents under anhydrous conditions, unless otherwise noted. The solvents used were ACS grade from Fisher. Reagents were purchased from Aldrich and Fisher, and used without further purification. Reactions were monitored by thin-layer chromatography (TLC) carried out on 0.20 mm POLYGRAM® SIL silica gel plates (Art.-Nr. 805 023) with fluorescent indicator UV254 using UV light as a visualizing agent. Normal phase flash column chromatography was carried out using Davisil® silica gel (100-200 mesh, Fisher). $^1$H NMR and $^{13}$C NMR spectra were recorded on a Jeol JNM-ECA600 spectrometer and calibrated using residual undeuterated solvent as an internal reference. Coupling constants (J) were expressed in Hertz. The following abbreviations were used to explain the multiplicities: s=singlet, d=doublet, t=triplet, q=quartet, m=multiplet. High-resolution mass spectra (HRMS) were recorded by JEOL DART AccuTOF (Direct Analysis in Real Time). HPLC analysis was performed on Agilent 1100 series HPLC system connected to a diode array detector operating between the UV ranges of 200-400 nm and quantified using Agilent Chemstation software. The HPLC analysis was performed on both Waters™ XBridge C18 column with L1 packing (4.6×250 mm, 5 μm) and Symmetric™ C4 (2.1×150 mm, 5 μm) at ambient temperature upon injection of a 50 μl of each Blank buffer, standard and/or sample to obtain the chromatogram. The mobile phase was composed of solvent A consisting methanol-water (5:95, v/v) containing 0.1% formic acid and solvent B consisting methanol-water (95:5, v/v) containing 0.1% formic acid. The HPLC program was a gradient separation method increasing linearly from 0% to 100% solvent B from 0 to 20 min and then maintained 100% solvent B up to 30 min.

Key Compounds Purity: HPLC analysis was performed on both C18 and C4 reversed-phase columns. The purity for all key compounds was >95%. Description of the purity analysis has been included in the experimental section. Detailed HPLC information of key compounds (traces, retention times, and % Purity) are included in the supplementary information of the revised manuscript.

Synthetic Procedures. AG10 and tafamidis were synthesized as reported earlier. Tolcapone and Diflunisal were purchased from Fisher. All AG10 analogues were prepared as described below.

3-(3-(3,5-dimethyl-1H-pyrazol-4-yl)propoxy)-4-iodobenzoic acid (1a); A solution of methyl 3-(3-bromopropoxy)-4-Iodobenzoate (5a) (834 mg, 2.1 mmol, 1 equiv) in benzene (3 ml) was added dropwise to a solution of acetyl acetone (0.43 ml, 4.2 mmol, 2 equiv) and DBU (0.627 ml, 4.2 mmol, 2 equiv) in benzene (7 ml). The reaction mixture was stirred at room temperature for 3 days. The mixture was filtered and concentrated. To a solution of this intermediate in ethanol (5 ml) was added hydrazine hydrate (0.28 ml, 5.25 mmol, 2.5 equiv) and the reaction was heated under reflux for 4 hr. The reaction was concentrated and purified by flash column chromatography (silica gel, 1-20% MeOH/CH2Cl2) to afford the methyl ester of compound 1a; Sodium hydroxide (79 mg, 1.98 mmol, 2 equiv) in water (2.5 ml) was added to a solution of ester intermediate (412 mg, 0.99 mmol) in methanol (10 ml) and the reaction was heated under reflux for 4 hr (50° C.). The reaction was concentrated and purified by flash column chromatography (silica gel, 1-5% MeOH/EtOAc) to afford compound 1a (183 mg, 22% yield for three steps); (98.3% purity by HPLC): tR (column) (C18)=25.72 min; tR (C4) =16.06 min. $^1$H NMR (CD3OD, 600 MHz) δ 7.86 (d, 1H, J=8.4 Hz), 7.41 (d, 1H, J=1.2 Hz), 7.34 (dd, 1H, J=1.2 Hz and 8.4 Hz), 4.0 (t, 2H, J=6.0 Hz), 2.67 (t, 2H, J=7.2 Hz), 2.13 (s, 6H), 1.97-1.93 (m, 2H). $^{13}$C NMR (CD3OD, 600 MHz) δ 168.5, 157.6, 142, 139.2, 133.2, 123.1, 114, 117.8, 91.7, 67.5, 29.6, 18.7, 9.3; (HRMS (DART) m/z: calcd for C15H17IN2O3+H+401.0362; found 401.0347 (M+H+).

Methyl 3-(3-(3,5-dimethyl-1H-pyrazol-4-yl)propoxy)-4-fluorobenzoate (2); A solution of methyl 3-(3-bromopropoxy)-4-fluorobenzoate (5b) (780 mg, 2.69 mmol, 1 equiv) in benzene (3 ml) was added dropwise to a solution of acetyl acetone (0.552 ml, 5.38 mmol, 2 equiv) and DBU (0.804 ml, 5.38 mmol, 2 equiv) in benzene (7 ml). The reaction mixture was stirred at room temperature for 3 days. The mixture was filtered and concentrated. The residue was purified by flash column chromatography (silica gel, 1-10% EtOAc/hexanes) to afford the alkylated intermediate which was used in the next step directly. To a solution of this intermediate in ethanol (5 ml) was added hydrazine hydrate (0.36 ml, 6.73 mmol, 2.5 equiv) and the reaction was heated under reflux for 4 hr. The reaction was concentrated and purified by flash column chromatography (silica gel, 1-20% MeOH/CH$_2$Cl$_2$) to afford compound 2 (288 mg, 35% yield); (96.3% purity by HPLC): tR (column) (C18)=25.11 min; tR (C4)=14.03 min. $^1$H NMR (CD$_3$OD, 600 MHz) δ 7.63-7.58 (m, 2H), 7.19-7.15 (m, 1H), 4.00 (t, 2H, J=6.0 Hz), 3.86 (s, 3H), 2.58 (t, 2H, J=7.2 Hz), 2.12 (s, 6H), 1.97-1.92 (m, 2H). $^{13}$C NMR (CD$_3$OD, 600 MHz) δ 168.1, 158.4, 156.7, 148.9, 128.5, 124.6, 117.6, 117.0, 115.6, 69.4, 53.3, 31.1, 20.2, 10.9; HRMS (DART) m/z: calcd for C$_{16}$H$_{19}$FN$_2$O$_3$+H$_+$ 307.1458; found 307.1463 (M+H$_+$).

4-fluoro-3-(3-(1,3,5-trimethyl-1H-pyrazol-4-yl)propoxy) benzoic acid (3): A solution of 2 (21 mg, 0.07 mmol, 1 equiv) in DMF (3 ml) was added sodium hydride (5 mg, 0.21 mmol, 3 equiv) and methyl iodide (17 μl, 0.28 mmol, 4 equiv). The reaction mixture was stirred at room temperature for 2 hr. The mixture was extracted with brine, filtered and concentrated. The residue was purified by flash column chromatography (silica gel, 0.5-2% MeOH/EtOAc) to afford the alkylated intermediate which was used in the next step directly. Sodium hydroxide (5.6 mg, 0.14 mmol, 2 equiv) in water (0.5 ml) was added to a solution of alkylated intermediate in methanol (2 ml) and the reaction was heated under reflux for 4 hr (50° C.). The reaction was concentrated and purified by flash column chromatography (silica gel, 1-5% MeOH/EtOAc) to afford compound 3 (11 mg, 52% yield for two steps); (97.8% purity by HPLC): tR (column) (C18)=25.25 min; tR (C4)=15.71 min. $^1$H NMR (CD$_3$OD, 600 MHz) δ 7.58-7.51 (m, 2H), 7.10-7.06 (m, 1H), 3.92 (t, 2H, J=6.0 Hz), 3.56 (s, 3H), 2.49 (t, 2H, J=7.2 Hz), 2.05 (s, 3H), 2.01 (s, 3H), 1.83-1.88 (m, 2H). $^{13}$C NMR (CD$_3$OD, 600 MHz) δ 168.1, 154.6, 146.8, 145.3, 137.2, 128.1, 122.8, 115.5, 115.4, 114.8, 67.4, 34.3, 29.4, 18.8, 10.1, 7.9; HRMS (DART) m/z: calcd for C$_{16}$H$_{19}$FN$_2$O$_3$+H$_+$ 307.1458; found 307.1449 (M+H$_+$).

3-(3-(3,5-diethyl-1H-pyrazol-4-yl)propoxy)-4-fluorobenzoic acid (4): Sodium hydroxide (3.2 mg, 0.08 mmol, 2 equiv) in water (0.5 ml) was added to a solution of 6 (13 mg, 0.04 mmol, 1 equiv) in methanol (2 ml) and the reaction was heated under reflux for 4 hr (50° C.). The reaction was concentrated and purified by flash column chromatography (silica gel, 1-5% MeOH/EtOAc) to afford compound 4 (10 mg, 80% yield); (96.0% purity by HPLC): tR (column) (C18)=25.16 min; tR (C4)=15.56 min. $^1$H NMR (CD$_3$OD, 600 MHz) δ 7.57-7.49 (m, 2H), 7.08-7.04 (m, 1H), 3.94 (t, 2H, J=6.0 Hz), 2.51-2.43 (m, 6H), 1.87-1.82 (m, 2H), 1.06 (t, 6H, J=7.8 Hz). $^{13}$C NMR (CD$_3$OD, 600 MHz) δ 169.8, 157.9, 156.3, 149.3, 148.5, 124.6, 117.2, 117.1, 114.1, 69.4, 31.8, 20.1, 19.9, 14.7; HRMS (DART) m/z: calcd for C$_7$H$_{21}$FN$_2$O$_3$+H$_+$ 321.1614; found 321.1601 (M+H$_+$).

Methyl 3-(3-bromopropoxy)-4-fluorobenzoate (5): compound 5 was synthesized as reported earlier. To a solution of methyl 4-fluoro-3hydroxybenzoate (1.0 g, 5.87 mmol, 1 equiv) and 1,3-dibromopropane (3.0 ml, 29.4 mmol, 5 equiv) in DMF (15 ml) was added K$_2$CO3 (0.98 g, 7.1 mmol, 1.2 equiv). The reaction mixture was stirred at room temperature for 16 hours. The mixture was diluted with EtOAc (500 ml), washed with brine (3×200 ml) and dried with Na$_2$SO$_4$. The solution was filtered and concentrated. The residue was purified by flash column chromatography (silica gel, 1-10% EtOAc/hexanes) to afford compound 5 (1.3 g, 76% yield); $^1$H NMR (CD$_3$OD, 600 MHz) δ 7.67-7.61 (m, 2H), 7.14-7.07 (m, 1H), 4.21 (t, 2H, J=5.89 Hz), 3.89 (s, 3H), 3.62 (t, 2H, J=6.38 Hz), 2.38-2.31 (m, 2H); (ESI+) m/z: calcd for C$_{11}$H$_{12}$BrFO$_3$+H$_+$ 290.00; found 290.01 (M+H$_+$).

Methyl 3-(3-(3,5-diethyl-1H-pyrazol-4-yl)propoxy)-4-fluorobenzoate (6): A solution of 5b (100 mg, 0.35 mmol, 1 equiv) in benzene (2 ml) was added dropwise to a solution of 3,5-heptanedione (0.095 ml, 0.7 mmol, 2 equiv) and DBU (0.104 ml, 0.7 mmol, 2 equiv) in benzene (5 ml). The reaction mixture was stirred at room temperature for 3 days. The mixture was filtered and concentrated. The residue was purified by flash column chromatography (silica gel, 1-10% EtOAc/hexanes) to afford the alkylated intermediate which was used in the next step directly. Hydrazine hydrate (0.047 ml, 0.875 mmol, 2.5 equiv) was added to the alkylated intermediate in ethanol (4 ml) and the reaction was heated under reflux for 4 hr. The reaction was concentrated and purified by flash column chromatography (silica gel, 1-5% MeOH/EtOAc) to afford compound 6 (75 mg, 65% yield for two steps); $^1$H NMR (CD$_3$OD, 600 MHz) δ 7.59-7.54 (m, 2H), 7.15-7.11 (m, 1H), 3.98 (t, 2H, J=6.0 Hz), 3.81 (s, 3H), 2.56-2.47 (m, 6H), 1.91-1.86 (m, 2H), 1.13 (t, 6H, J=7.8 Hz). C NMR (CD$_3$OD, 600 MHz) δ 167.9, 156.6, 156.2, 148.8, 148.7, 124.4, 117.5, 117.3, 116.9, 113.9, 69.5, 53.1, 31.8, 20.1, 14.7; HRMS (DART) m/z: calcd for C$_{18}$H$_{23}$FN$_2$O$_3$+H$_+$ 335.1771; found 335.1773 (M+H$_+$).

Results

Determination of Binding Affinities and Thermodynamics of Interactions Between Stabilizers and TTR. We used isothermal titration calorimetry (ITC) to determine the binding affinities ($K_d$) and the mechanisms underlying molecular interactions of all TTR stabilizers in clinical development (i.e. AG10, tafamidis, diflunisal and tolcapone) and AG10 analogues 1, 2, 3, and 4. Most of the reported TTR ligands bind to the two identical T4 binding sites of TTR with strong negative cooperativity and therefore the binding of the first ligand will dominate the total binding energy as well as the stabilizing effect. While some differences in cooperativity can be observed in the ITC thermograms, these differences will have minor influences on the binding energy as well as the stabilizing effect. Therefore, the $K_d$ values reported in Table 5 were based on data fitted to independent single-site binding model. The binding affinities of AG10 and tafamidis to TTR in buffer ($K_d$=4.8±1.9 and 4.4±1.3 nM, respectively) were 4-fold higher than tolcapone ($K_d$=20.6±3.7 nM) and ~100-fold higher than diflunisal ($K_d$=407±35 nM). The $K_d$ values for compounds 1-4 ranged from 90 to 1250 nM, and the results are summarized in Table 5. The $K_d$ for binding of a stabilizer to TTR is represented by the change in Gibbs free energy of binding ($\Delta G$), where $\Delta G=\Delta H-T\Delta S$. By analyzing the thermodynamic signature of each molecule, we can assess the relative contributions of enthalpic ($\Delta H$; representing the formation or breaking of chemical bonds) and entropic forces ($\Delta S$; associated with the amount of disorder in a system and frequently dominated and favored by release of bound water molecule due to hydrophobic interactions). Despite the similar binding affinities of AG10 and tafamidis to TTR in buffer (i.e., similar $\Delta G$ values), their binding energetics to TTR are notably different. Whereas the binding of AG10 ($\Delta H$=-13.60 kcal/mol and $T\Delta S$=-2.26 kcal/mol) is enthalpically driven, tafamidis binding is approximately 50% entropic and 50% enthalpic ($\Delta H$=-5.00 kcal/mol and $T\Delta S$=6.39 kcal/mol) (FIG. 16A and Table 5). The binding of tolcapone ($\Delta H$=-10.1 kcal/mol and $T\Delta S$=0.4 kcal/mol) and diflunisal ($\Delta H$=-8.38 kcal/mol and $T\Delta S$=0.34 kcal/mol) is entropically favorable but mainly driven by enthalpic interactions. The unfavorable entropic binding energy of AG10 for TTR ($T\Delta S$=-2.26 kcal/mol) could be due to its higher polarity and/or conformational flexibility compared to other TTR stabilizers. The themodynamics for the binding interactions between compounds 1-4 and TTR is discussed below.

negative) $\Delta H$ had a proportionally higher TTR selectivity compared to ligands with a lower influence of $\Delta H$. While this study described the correlation between enthalpic forces and selectivity of TTR stabilizers, no correlation between binding enthalpy of ligands and potency for stabilizing TTR or, to our knowledge, any other multimeric proteins has been reported yet. To evaluate the potency of stabilizers in occupying and stabilizing TTR in buffer we used the fluorescence probe exclusion (FPE) assay. The FPE assay uses a fluorogenic probe (FPE probe) that is not fluorescent by itself, however upon binding to the T4 binding site of TTR it covalently modifies lysine 15 (K15), creating a fluorescent conjugate. Ligands that bind to the T4 site of TTR will decrease FPE probe binding as observed by lower fluorescence. A linear correlation has been reported between the extent of fluorescence in the FPE assay and stabilization of TTR. Therefore, we first used the FPE assay to measure the potency of stabilizers for binding and stabilizing TTR in buffer (tested at 1:1 ratio of stabilizer to TTR tetramer; FIG. 16B,C and Table 5). The order of potency of the stabilizers for TTR in buffer was AG10>tolcapone>tafamidis>diflunisal.

We then employed the FPE and Western blot assays to evaluate the efficacy (representing both potency and selectivity) of stabilizers (10 μM) in occupying and stabilizing TTR in human serum (TTR concentration 5 μM) (Table 5). The Western blot assay measures the amount of intact TTR tetramer after 72 h of acid treatment in the presence and absence of stabilizers. The order of efficacy of the stabilizers in human serum was similar to what we observed for the potency with TTR in buffer (AG10>tolcapone>tafamidis>diflunisal; Table 5). The potency and efficacy of diflunisal was the lowest which is predicted based on its significantly lower binding affinity to TTR ($K_d$=407±35 nM) compared to all other stabilizers (20 to 80-fold lower affinity than other stabilizers). Surprisingly, there was no correlation between the $K_d$ values of the three other stabilizers and their potency and efficacy in occupying and stabilizing TTR in both buffer and human serum. For example, the potency and efficacy of tolcapone was higher than that of tafamidis despite the fact that the binding affinity of tolcapone to TTR ($K_d$=20.6±3.7 nM) is slightly lower than the binding affinity of tafamidis to TTR ($K_d$=4.4±1.3 nM). Interestingly, both potency and efficacy of these stabilizers for TTR in buffer and serum correlated very well ($R_2$=0.98) with their binding enthalpy ($\Delta H$=-13.6, -10.1, and -5.0 kcal/mol; for AG10, tolcapone

TABLE 5

Comparison of TTR stabilizers

| Stabilizer | $K_d$ (nM) | ITC Parameters (kcal/mol) | | | % TTR Occupancy in Buffer (1:1 ratio)[a] | % TTR Occupancy in Serum (2:1 ratio)[a] | % TTR Stabilization in Serum (2:1 ratio)[a] |
| --- | --- | --- | --- | --- | --- | --- | --- |
| | | $\Delta G$ | $\Delta H$ | $T\Delta S$ | | | |
| AG10 | 4.8 ± 1.9 | -11.34 | -13.6 | -2.26 | 79.1 ± 1.2 | 98.8 ± 2.9 | 95.4 ± 2.9 |
| Tafamidis | 4.4 ± 1.3 | -11.39 | -5.0 | 6.39 | 49.9 ± 3.3 | 49 ± 3.3 | 41.5 ± 4.6 |
| Diflunisal | 407 ± 35 | -8.72 | -8.38 | 0.34 | 28.7 ± 0.6 | 16.2 ± 3.2 | 24.2 ± 2.3 |
| Tolcapone | 20.6 ± 3.7 | -10.5 | -10.1 | 0.4 | 71.7 ± 2.5 | 71.1 ± 2.9 | 68.4 ± 5.1 |
| 1 | 90 ± 14 | -9.61 | -9.82 | -0.21 | 58.3 ± 0.9 | 75.9 ± 3.1 | 86.7 ± 2.3 |
| 2 | 258 ± 17 | -8.99 | -6.49 | 2.5 | 38.5 ± 0.8 | 63.2 ± 2.5 | 70.4 ± 2.2 |
| 3 | 251 ± 12 | -9.0 | -4.73 | 4.27 | 29.7 ± 0.7 | 43 ± 0.6 | 32.1 ± 4.9 |
| 4 | 1253 ± 79 | -8.1 | -2.1 | 6.0 | 17.2 ± 0.9 | 20.8 ± 3.3 | 23.2 ± 1.1 |

Enthalpic Force Predicts Potency of TTR Stabilizers in Buffer and Efficacy in Human Serum. A recent study with diflunisal and other nonsteroidal anti-inflammatory drugs (NSAIDs) found that ligands with favorable (i.e. larger and tafamidis, respectively). This data indicate that the enthalpically-driven binding of AG10 and tolcapone to TTR (discussed in details below) is the primary driver of their efficient stabilization of TTR compared to other stabilizers.

We then used the Western blot assay to compare the efficacy of AG10 (10 μM) to other stabilizers at their reported mean maximum plasma concentrations in human ($C_{max}$ of 20 μM for 80 mg tafamidis qd; 200 μM for diflunisal 250 mg bid; and 20 μM for tolcapone 100 mg dose tid). AG10 at 10 μM completely stabilized TTR in human serum (% TTR stabilization: 95.4±4.8%); the other compounds stabilized ~50-75% of tetrameric TTR at their reported clinical $C_{max}$ (FIG. 17A,B). The pKa values for AG10 (pKa=4.13) and tafamidis (pKa=3.73) are higher than that for diflunisal (pKa=2.94). Therefore, the percentage ionization of the carboxylic acid groups of stabilizers might vary at pH 4. This could affect the strength of the electrostatic interaction between the carboxylic acid groups and the ε-amino groups of lysine 15 (K15) and K15' at the top of the T4 binding sites which could affect the potency of the stabilizer. To address this concern, we performed the Western blot assay using Urea buffer (pH 7.4). The TTR stabilization data of in Urea buffer is similar to the data obtained from Western blot in acidic pH and from the FPE assay at physiological pH. Consistent with the Western blot TTR stabilization assay data, T4 binding site occupancy by 10 μM AG10 in the FPE assay was essentially complete (% TTR occupancy 96.6±2.1%) and higher than all stabilizers at their reported clinical $C_{max}$. The target occupancy for tolcapone at 20 μM (% TTR occupancy 86±3.2%) was higher than those of tafamidis and diflunisal (% TTR occupancy ~65% at 20 μM and 200 μM, respectively) (FIG. 17C,D).

Figures 18A, 18B, 18C, 18D, 18E:
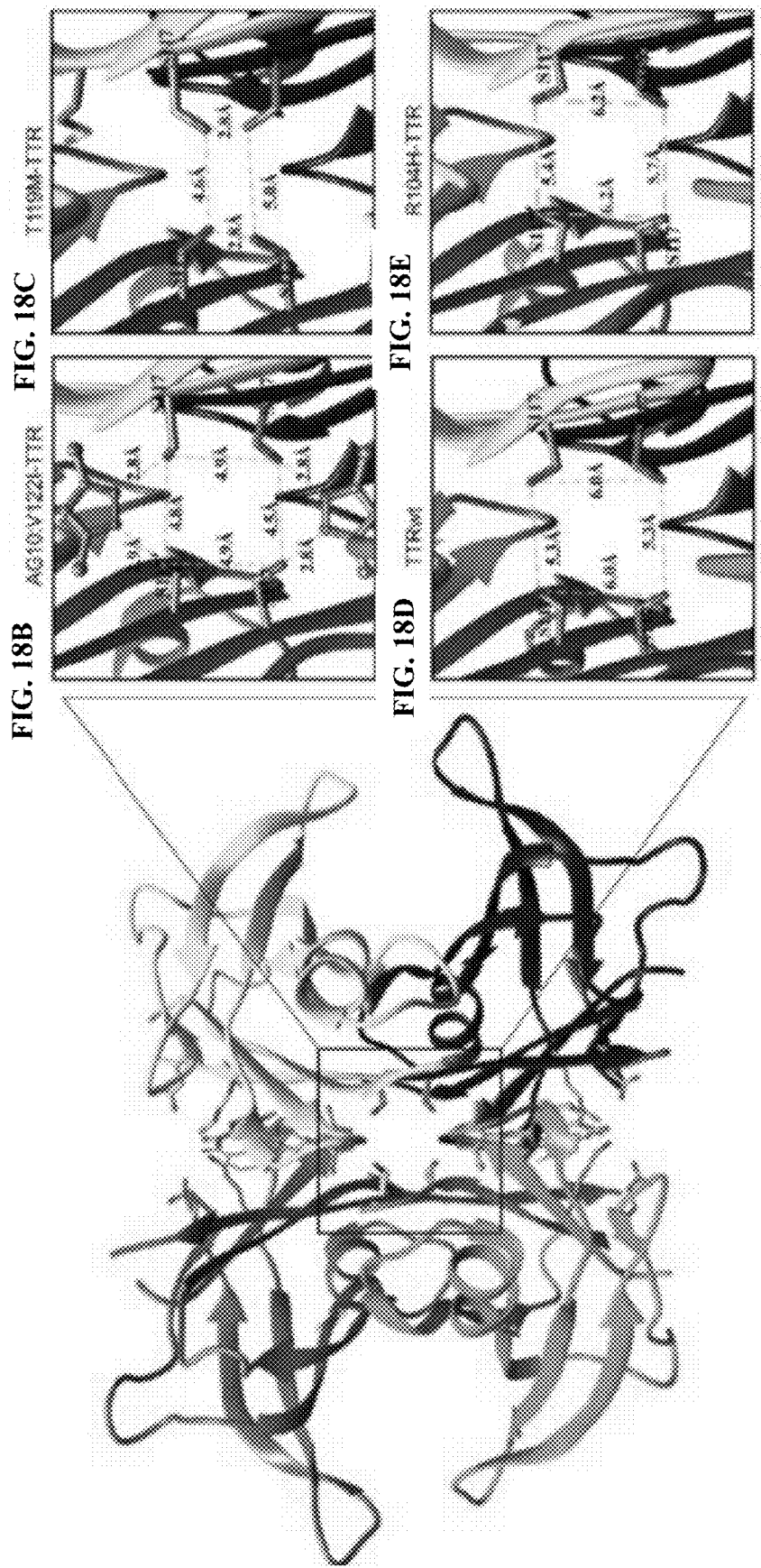
FIG. 18A-E shows crystal structures highlighting similar interactions caused by the T119M mutation and binding of AG10 to TTR. (A) shows a high-level view of a TTR tetramer. (B) Quaternary structure of AG10 bound to V122I-TTR (PDB: 4HIQ) shown as a ribbon representation with monomers colored individually. Close-up views of one of the two identical T4 binding sites with different colored ribbons for the two monomers of the tetramer composing the binding site. Key hydrogen bonds between the pyrazole ring of AG10 and S117/117' are highlighted by dashed lines. (C) Crystal structure of the stabilizing T119M-TTR variant (PDB: 1FHN) with dashed lines highlighting key interactions between the hydroxyl groups of S117 and S117'. (D) Crystal structure of TTRwt (PDB: 3CFM). (E) Crystal structure of thermodynamically stabilized R104H-TTR (PDB: 1X7T).

Binding Interactions Between AG10 and S117/S117' of TTR Mimic Molecular Interactions within the Disease-Protective T119M Mutation. We investigated the correlation between binding enthalpy and TTR stabilization by comparing reported co-crystal structures of stabilizers with TTR against the crystal structures of stabilizing TTR variants (T119M and R104H). We hypothesized that this could allow us to identify functional groups of amino acids within the T4 binding sites of TTR which are important for binding and stabilization of TTR. The carboxylic acid moieties of AG10, tafamidis, diflunisal, and the hydroxyl group on tolcapone all participate in electrostatic interactions with the ε-amino groups of lysine 15 (K15) and K15' at the top of the T4 binding sites. The enthalpically driven binding of AG10 and tolcapone to TTR is driven by additional hydrogen bonds that both molecules form within the T4 binding site. The carbonyl group of tolcapone forms one hydrogen bond with hydroxyl side chain of T119 of TTRwt (distance ~2.6 Å; ideal distance for a hydrogen bond is <3 Å). The longer distance between the carbonyl group of tolcapone and hydroxyl side chain of T119' on the adjacent monomer (distance ~7.6 Å) preclude the formation of a second hydrogen bond. Interestingly, this interaction is weaker between tolcapone and V122I-TTR (distance between the carbonyl group of tolcapone and hydroxyl side chains of T119 and T119' of V122I-TTR are ~5.5 Å and ~9.6 Å, respectively), which could explain the lower binding affinity ($K_d$=56 nM) and potency of tolcapone toward V122I-TTR compared to TTRwt. In the case of tafamidis, there is no hydrogen bonding at the base of the T4 pocket; instead, the chlorine atoms of the 3,5-dichloro ring are also placed into halogen binding pocket (HBP) 3 and 3', where they interact with TTR through predominantly hydrophobic interactions. In addition to electrostatic interactions between the carboxylic acid moiety of AG10 and K15/K15', AG10 also forms two hydrogen bonds with the hydroxyl side chain serine 117 (S117) and S117' (distance ~2.8 Å) of adjacent monomers in the low dielectric macromolecular interior of the T4 binding site (FIG. 18B). These additional hydrogen bonds are likely to be responsible for the driving force for the dominant enthalpic binding of AG10 to TTR. Remarkably, similar hydrogen bonds have been reported within the inner cavity of the kinetically stabilizing trans-suppressor T119M-TTR variant (FIG. 18B).

The two S117 side chain hydroxyl groups of monomers A and B in T119M variant TTR form direct hydrogen bonds with a distance of 2.8 Å, which are not observed in TTRwt (distance between the two S117 residues ~6.0 Å) (FIG. 18D). These unique hydrogen bonds lead to closer contacts between the two dimers (~4.8 Å) within the TTR tetramer and highlight the potential importance of these hydrogen bonds in the anti-amyloidosis and disease-protective effects of the T119M variant on the TTR tetramers. The role of S117 in stabilizing TTR has been also suggested by the binding of flavonoids that are capable of forming a single hydrogen bond with one S117. Interestingly, the distance between the Si 17 and Si 17' residues in the thermodynamically stabilized R104H variant, which does not involve kinetic stabilization of the tetrameric TTR, is similar to that of TTRwt (average dimer-dimer distance is ~5.6 Å, FIG. 18D,E). The lack of hydrogen bonding between the hydroxyl groups of S117 and S117' in the R104H variant (which is a less potent trans-suppressor mutant than T119M) highlights the importance of these hydrogen bonds in the anti-amyloidogenic and disease suppressing effects of kinetically stabilizing the TTR tetramer in the T119M variant. By forming two direct hydrogen bonds with S117 and S117' in the TTR tetramer, AG10 creates a similar electrostatic bridge as is found in the protective T119M variant. This data is supported by the analysis of 40 reported crystal structures which highlighted the closer dimer-dimer contacts in the crystal structures of both T119M-TTR (distance ~4.8 Å) and ΔG10-V122I-TTR (distance ~4.66 Å) compared to TTRwt or TTRm (distance ~5.5 Å) (Supplementary Table 1). It is important to note that other known TTR stabilizers do not interact with S117/S117' of TTR.

Figure 15:
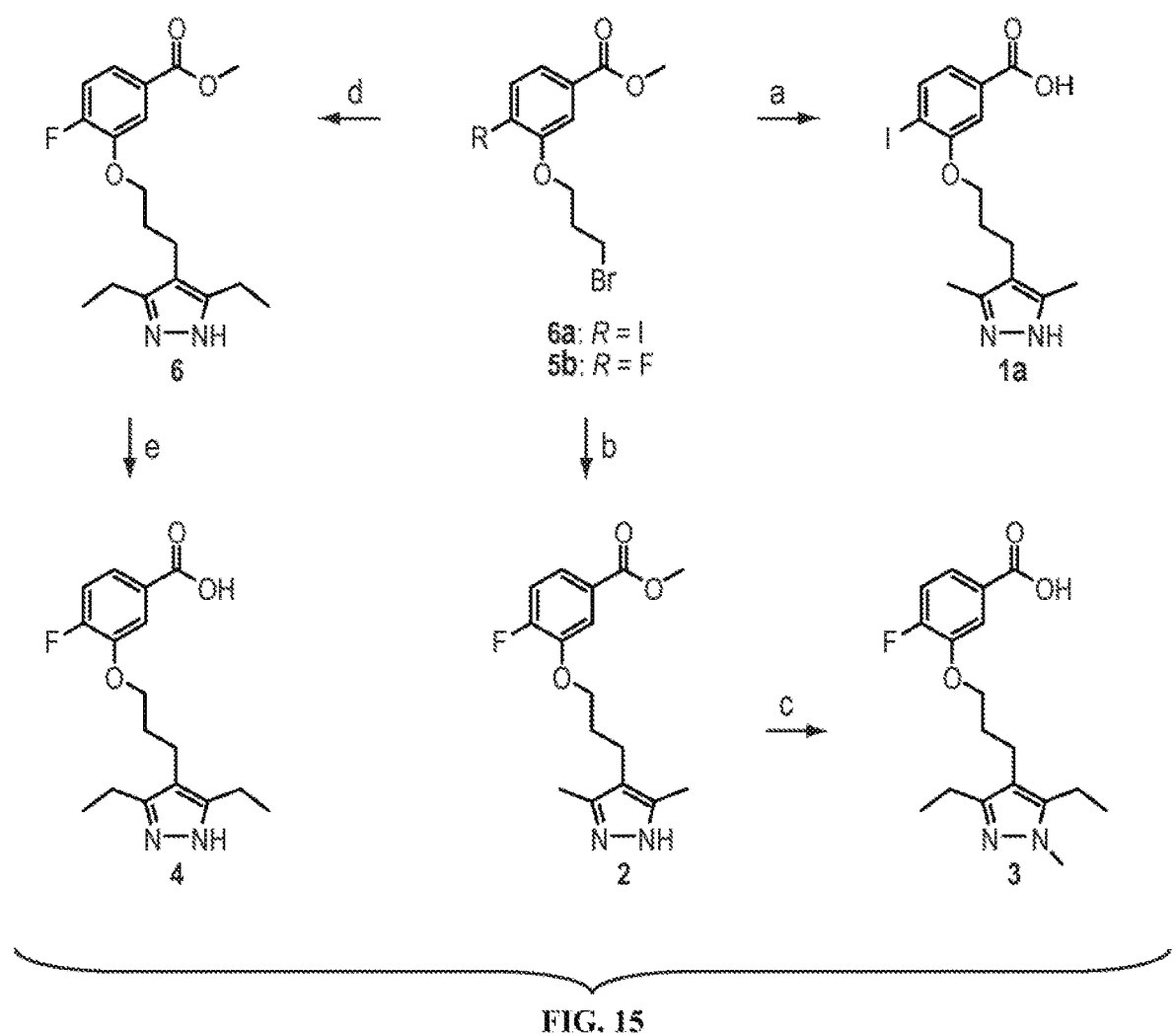
FIG. 15 shows the synthesis of AG10 analogues 1, 2, 3, and 4. Step a) 6a, i. acetylacetone, DBU, benzene, rt, 3 days; ii. hydrazine hydrate, ethanol, 90° C., 4 h; iii. NaOH, MeOH/water, 50° C., 14 h; Step b) 5b, i. acetylacetone, DBU, benzene, rt, 3 days; ii. hydrazine hydrate, ethanol, 90° C., 4 h; Step c) 1. NaH, MeI, DMF, rt, 12 hr; ii. NaOH, MeOH/water, 50° C., 14 h; Step d) 5b, i. 3,5-Heptanedione, DBU, benzene, rt, 3 days; ii. hydrazine hydrate, ethanol, 90° C., 4 h; Step e) NaOH, MeOH/water, 50° C., 14 h.

Characterization of key functional groups of AG10 important for TTR Stabilization. In order to investigate the enthalpic contribution of each of the functional groups of AG10 on TTR binding and stabilization, we synthesized and tested four AG10 analogues (compounds 1, 2, 3, and 4; FIG. 15) and evaluated their ability to bind and stabilize TTR (FIG. 19). AG10 binds TTR with unfavorable entropy (TΔS=−2.26 kcal/mol). The fluorine atom of AG10 is placed into HBP1 of TTR and therefore we hypothesized that the entropic binding of AG10 to TTR could be optimized by replacing the fluorine atom of AG10 with an iodine (compound 1a). Modeling studies suggest the iodine of 1 fits in HBP1 of TTR (where the iodine of T4 binds) which could improve the entropic binding by displacing more water molecules from HBP1 (FIG. 19A). Compound 1a displayed significantly lower binding affinity ($K_d$=90±14 nM) to TTR in buffer compared to AG10 ($K_d$=4.8±1.9 nM). ITC analysis showed that while the entropic interaction of 1 with TTR was more favorable compared to AG10 (TΔS=−0.21 kcal/mol and −2.26 kcal/mol, respectively), there was a significant drop in the enthalpic contribution to the binding (ΔH=−9.82 kcal/mol and −13.6 kcal/mol, respectively) (FIG. 19B). As suggested by modeling, the decrease in binding enthalpy could be explained by the decrease in strength of the salt bridge between the carboxylic acid moiety of 1 and K15/K15' (distance ~4.7 Å compared to ~2.8 Å for AG10). Compound 1a also displayed reduced potency for TTR in buffer (58.3±0.98%) and human serum (75.9±3.1%) compared to AG10 (FIG. 19C-E and Table 5).

The carboxylic acid moiety of AG10 forms two salt bridges directly with the ε-amino groups of K15 and K15' at the periphery of the T4-binding site which serve to close the T4 pocket around AG10 and partially shield it from the solvent. We synthesized a methyl-ester analogue of AG10 (compound 2, FIG. 19A) to test the effect of modifying the two salt bridges that AG10 forms at the periphery of the T4-binding site. Compound 2 displayed significantly lower affinity ($K_d$=258±17 nM) to TTR in buffer compared to AG10 ($K_d$=4.8±1.9 nM), which could be explained by the lower strength of potential hydrogen bonds between the ester group of 2 and K15/K15' ($\Delta H$=−6.49 kcal/mol) compared to the salt bridge in AG10 (FIG. 19B). Compound 2 also displayed reduced potency for TTR in buffer and human serum compared to AG10 and compound 1a (FIG. 19C-E and Table 5).

The 3,5-dimethyl-1H-pyrazole ring of AG10 sits deep within the inner cavity of the T4-binding site, and forms two hydrogen bonds with the S117 and S117' of adjacent subunits. By blocking these interactions, we can effectively observe their enthalpic contribution using ITC and the FPE assay, respectively. Therefore, we synthesized compound 3 which has an N-methyl pyrazole. The N-methyl group would restrict the pyrazole ring of 3 to form only one hydrogen bond with one of the adjacent TTR subunits (FIG. 19A). We also synthesized compound 4 where the dimethyl pyrazole of AG10 was replaced with diethyl pyrazole. Modeling studies suggested that the bulk of the diethyl groups would prevent the molecules for reaching deep in the T4-binding site, thereby decreasing its ability to potentially form any hydrogen bonds with S117/S117' (FIG. 19A). As predicted by modeling, both 3 ($K_d$=251±12 nM) and 4 ($K_d$=1253±79 nM) showed greatly reduced binding affinity to TTR in buffer. This reduced affinity was translated into a significant decrease in potency for TTR in buffer and human serum, especially for compound 4. The order of potency for stabilizing TTR was similar in both buffer and serum (1>2>3>4; FIG. 19C-E and Table 5). As we observed with the clinical ATTR stabilizers, the potency of AG10 and compounds 1, 2, 3, and 4 in occupying and stabilizing TTR correlated very well ($R_2$=0.98) with the binding enthalpy of these molecules ($\Delta H$=−13.6, −9.82, −6.49, −4.73, and −2.1 kcal/mol, respectively). Interestingly, despite the similar binding affinities of 2 and 3, their potency was significantly different (Table 5). The higher potency of 2 compared to 3 could be explained by its favorable enthalpic binding ($\Delta H$=−6.49 kcal/mol and −4.73 kcal/mol, respectively) (FIG. 19B). This observation is similar to the data obtained for AG10 and tafamidis (i.e. similar $K_d$ values but significantly different potency) (Table 5). These results highlight the crucial role played by the pyrazole ring and the importance of the hydrogen bonds it forms with the two TTR dimers, mimicking the interactions in the protective T119M-TTR mutation, and enhancing the kinetic stability of the TTR tetramer.

Examining the effect of enthalpy on the selectivity of AG10 to TTR. To examine the role of enthalpy on the selectivity of AG10 for TTR over other abundant serum proteins, we tested the concentration-effect relationship of AG10 and tafamidis in the FPE assay in whole human serum. We tested AG10 and tafamidis since their binding affinities for TTR in buffer is very similar ($K_d$=4.8±1.9 nM and 4.4±1.3 nM, respectively) but their thermodynamics for binding TTR, especially the enthalpy component, is significantly different. Therefore, the data obtained in serum would largely reflect selectivity. AG10 displayed a progressive concentration-dependent occupancy, with complete occupancy achieved at AG10 concentrations ≥10 μM. Even at sub-stoichiometric concentrations, AG10 was able to occupy and stabilize the majority of TTR (at 5 μM, TTR occupancy of 69.2% by FPE, 74.5% stabilization by Western blot). In contrast, there was a more modest increment in either occupancy or stabilizing activity of tafamidis at concentrations above 20 μM. A good correlation ($R_2$=1.0) between TTR occupancy (by FPE) and TTR stabilization (by Western blot) was observed when the activity of AG10 was evaluated. For tafamidis, there was a good correlation ($R_2$=0.87) for concentrations up to 10 μM, however, at higher concentrations there was a plateau in the FPE assay.

Figure 20A:
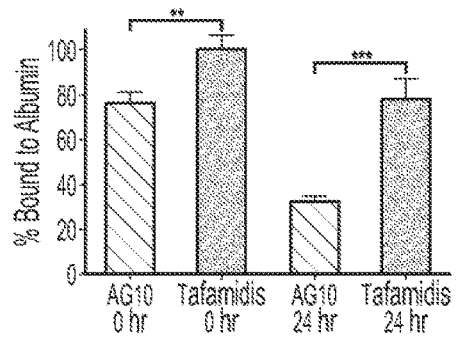
FIG. 20A-F illustrates that AG10 has high selectivity for binding TTR over albumin or other abundant human serum proteins. (A) Gel filtration and dialysis assay comparing AG10 and tafamidis (each at 30 μM) incubated with purified human serum albumin (600 μM). The concentration of tafamidis bound to albumin after gel-filtration (i.e. dialysis time 0 hr) was normalized to 100%. Error bars indicate SD (n=3). (B) 24 hr time-course for dialysis of AG10 (10 μM) incubated with purified human TTR (5 μM). Error bars indicate SD (n=3). (C) Fluorescence change due to modification of purified human TTR (5 μM) by FPE probe monitored for 6 hr in the presence of probe alone (black circles), probe plus albumin (600 μM) (black triangles), probe plus all [fibrinogen (5 μM), albumin (600 μM), IgG (70 μM), transferrin (25 μM)] (grey triangles); probe and AG10 (10 μM) (red squares) or probe and AG10 plus albumin (green diamonds), probe and AG10 plus all [fibrinogen (5 μM), albumin (600 μM) IgG (70 μM), transferrin (25 μM)] (blue circles). (D) % TTR occupancy in buffer by AG10 in the presence of FPE probe and other serum proteins measured after 3 hr of incubation relative to probe alone. (E, F) Same experiment described for AG10 was performed for tafamidis. Error bars indicate SD (n=3). The significance of the differences were measured by one-way ANOVA followed by Tukey's multiple comparison test (n.s., not significant; *$p \leq 0.05$; $p \leq 0.01$; *$p \leq 0.001$).
Figure 20B:
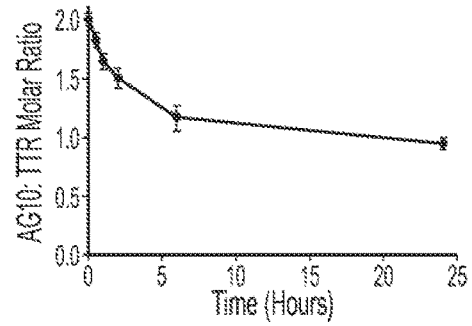
Figure 20C:
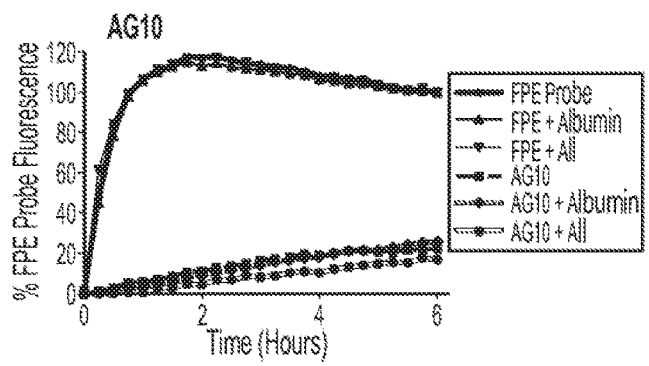
Figure 20D:
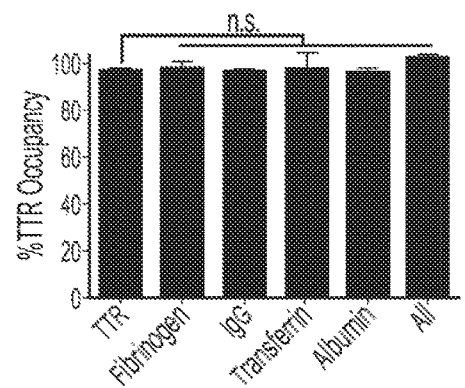

The selectivity of AG10 and tafamidis for TTR was further investigated by repeating these assays in buffer in the presence or absence of purified serum proteins. AG10 or tafamidis (30 μM) were pre-incubated with purified human serum albumin (at its physiological concentration of 600 μM) and then subjected to gel filtration followed by dialysis. At time 0 (immediately after gel filtration), less AG10 was bound to albumin compared to tafamidis (18.3±0.98 μM vs. 24.1±1.1 μM; FIG. 20A). Following dialysis vs buffer for 24 hr, the concentration of AG10 bound to HSA was lower than that for tafamidis (7.8±0.1 μM vs. 18.8±2.1 μM). These data indicate that AG10 has a lower binding affinity for albumin compared to tafamidis. In parallel the binding of AG10 to TTR was also investigated in this gel filtration/dialysis assay. AG10 (10 μM) was pre-incubated with an equimolar ratio TTR (5 μM of tetrameric TTR, representing 10 μM of TTR T4 binding sites). The dissociation of AG10 from TTR was slow for the first six hours (AG10-TTR molar ratio of ~1.2:1), and maintained a 1:1 molar ratio over a 24 hr incubation (FIG. 20B).

Figure 20E:
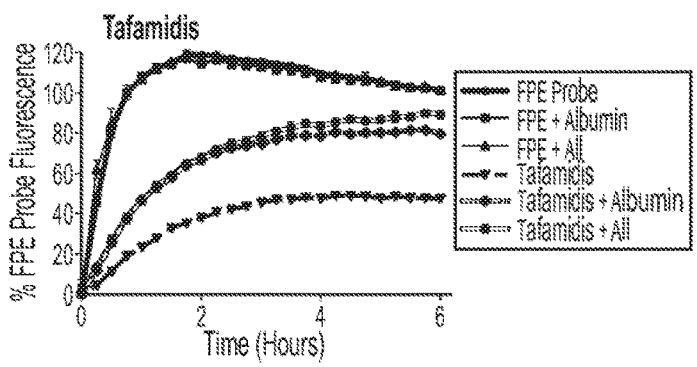
Figure 20F:
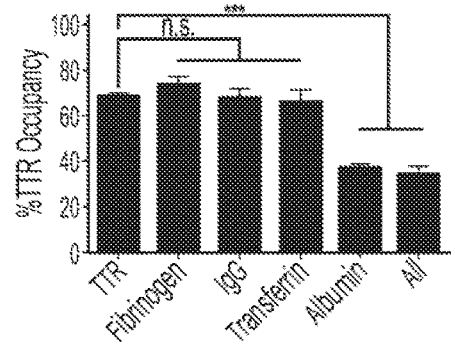

Finally, the selectivity of AG10 and tafamidis for binding to TTR in human serum was evaluated using a modified FPE assay where human serum was replaced with purified human TTR in buffer (PBS buffer, pH 7.4). In addition to purified TTR (5 μM), four separate representative and abundant plasma proteins were added to the FPE assay in buffer. Addition of albumin, transferrin, fibrinogen or immunoglobulin (IgG) did not influence TTR occupancy by AG10 (>97% TTR occupancy in the absence or presence of any of these proteins, FIG. 20C,D). Albumin, but not the other serum proteins tested, interfered with TTR occupancy by tafamidis (41.5±0.9% vs. 68.2±0.1% in the absence of albumin; FIG. 20E,F). Adding all of the tested plasma proteins simultaneously yielded identical results for AG10. The higher selectivity of AG10 for TTR could be attributed to a number of properties, including the enthalpic binding and greater hydrophilicity of AG10 (C log P=2.78) compared to the more lipophilic tafamidis (C log P=4.2).

Healthy Beagle Dog is a Suitable Experimental Model for Evaluating the Efficacy of TTR Stabilizers. We then investigated if the high potency and selectivity of AG10 for TTR can be maintained in vivo. Transgenic animal models that faithfully reproduce the pathology of human ATTR-CM are not yet available. Therefore, we took an approach similar to that currently used in the clinic to examine the efficacy of AG10 vs other TTR kinetic stabilizers. The activity of TTR stabilizers in occupying and stabilizing TTR is commonly assessed ex vivo in blood samples obtained from patients before and after dosing of the stabilizer. To explore the in vivo activity of AG10, this same approach was used in the healthy beagle dog. The healthy beagle dog was chosen as an experimental model for several reasons. All amino acids in the T4 binding sites of TTR, where AG10 and other stabilizers bind, are conserved between dog and human. We also tested the concentration of TTR in dog serum (~4.6 μM) and found it similar to that of healthy humans. To confirm the suitability of assays used with human-based reagents for dog studies, the activity of AG10 and tafamidis was evaluated in pooled dog serum using the same FPE and Western blot assays used for the experiments described above. The in vitro TTR binding and stabilization concentration-effect relationships of AG10 and tafamidis in both assays repeated using dog serum was similar to those observed in human serum (FIG. 21). These features made the healthy canine a suitable system for subsequent investigations.

AG10 Potently and Selectively Binds to Canine TTR Following Oral Administration. To explore the pharmacokinetic-pharmacodynamic (PK-PD) relationship in vivo, AG10 was administered to healthy beagle dogs daily by oral gavage for 7 days. A total of 16 male (M) and 16 female (F) beagle dogs made up four treatment groups: (i) 6M/6F at 0 mg/kg/d (vehicle control); (ii) 2M/2F at 50 mg/kg/d; (iii) 2M/2F at 100 mg/kg/d; and (iv) 6M/6F at 200 mg/kg/d. Timed serum samples were collected pre-dose on study day 1 (baseline), pre-dose on study day 7 (representing trough concentrations, or $C_{min}$, at steady state), and at 1 hr post-dose on study day 7 (representing peak concentrations, or $C_{max}$, at steady state). Binding occupancy of TTR by AG10 was assessed by FPE assay (FIG. 22A,B). All samples from dogs treated with vehicle alone, and those collected from the active treatment arms prior to exposure to AG10, showed zero TTR occupancy. Serum from AG10-treated dogs displayed a dose-proportional response in binding occupancy at the steady state trough (day 7 pre-dose; ~81-94% TTR occupancy), and all AG10 treated groups showed complete (>97%) TTR occupancy at steady state $C_{max}$ (day 7 post-dose). Lower doses of AG10 were subsequently tested to further explore the PK-PD (exposure-effect) relationship in order to identify a minimally effective dose of AG10 that might still effectively bind to and stabilize TTR. Eight dogs divided into two active treatment groups received either 5 or 20 mg/kg AG10 HCl as a single oral dose. These results showed enhanced TTR occupancy in the 20 mg/kg vs. 5 mg/kg dose groups (FIG. 22C,D). The % TTR occupancy at $C_{max}$ was significantly higher ($p \leq 0.001$) than at $C_{min}$ for both doses. There was significantly higher ($p \leq 0.001$) TTR occupancy for the 20 mg/kg dose compared to the 5 mg/kg dose at $C_{min}$. The data also showed that circulating plasma concentration of AG10 correlates well with % TTR occupancy.

In summary, Beagle dogs demonstrated that AG10 is orally available at particular dosage levels, and achieves dose-dependent plasma concentrations that potently and selectively bind and stabilize tetrameric TTR.

Figure 23:
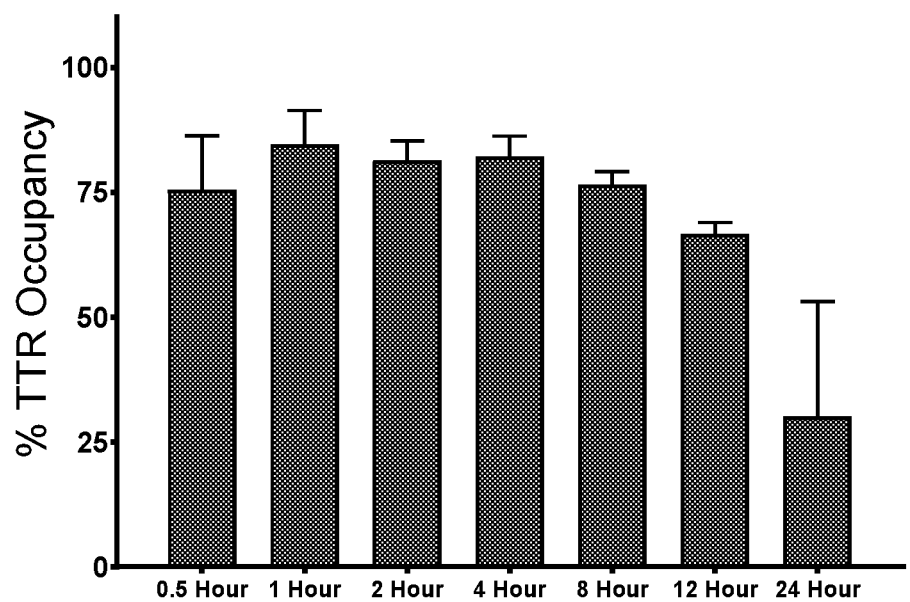
FIG. 23 illustrates the % TTR occupancy at 3 hr in serum from 3 male cynomolgus monkeys after oral dosing of AG10 HCl at 5 mg/kg. Data is mean±SD of 3 replicates.

Example 5: A Single Dose Study in Monkeys Administered AG10 HCl by Intravenous Administration or Oral Gavage AG10 HCl was administered at dose levels of 1 mg/kg intravenous or 5 mg/kg per oral to 3 male cynomolgus monkeys. There was a washout period of two weeks between the two phases. Blood samples were collected at pre-dose and at approximately 0.083 (IV only), 0.25, 0.5, 1, 2, 4, 8, 12, 24, 48, 72 and 96 hours post-dose. Plasma samples were assayed for AG10 and AG10 acylglucuronide and serum was tested in FPE assay. As shown in FIG. 23 results from FPE assay demonstrate that orally administered AG10 effectively binds to TTR in monkey serum.

Figure 24:
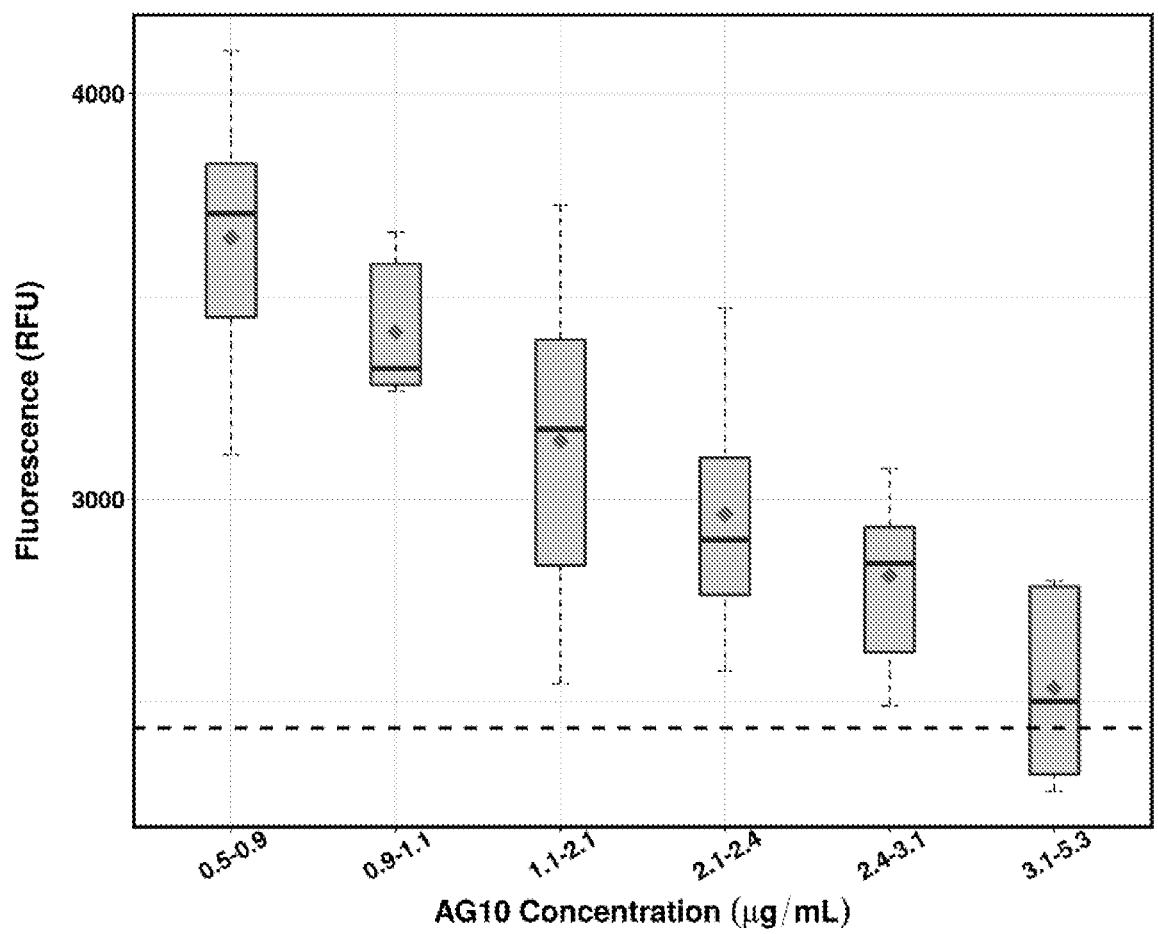
FIG. 24 illustrates the dose dependent relationship between orally administered AG10 and TTR stabilization in monkeys.

The FPE assay also demonstrated that orally administered AG10 stabilized TTR in a dose dependent manner (FIG. 24).

Example 6: TTR Blood Serum Concentrations Increase in Healthy Individuals Dosed with AG10

To measure blood serum TTR concentrations, a Prealbumin ELISA kit (human) from Aviva Systems Biology, catalog #OKIA00081-96W, lot #KC0699 was used.

The study was performed according to the protocol supplied by the ELISA kit manufacturer. The method was modified by addition of three standard concentrations to the manufacturer recommended calibration curve. The supplied TTR calibrator was dissolved in 1 mL of distilled water resulting in a concentration of 8.85 µg/mL. The first additional standard was 1000 ng/mL which was prepared by adding 178.4 µL of calibrator to 1400 µL of 1× diluent. The second additional standard was 200 ng/mL which was prepared by adding 32.4 µL of calibrator to 1400 µL of 1× diluent. The third additional standard was 0.78125 ng/mL which was prepared by adding 600 µL of the 1.5625 ng/mL standard to 600 µL of 1× diluent. The ELISA kit utilizes goat polyclonal anti-TTR antibodies for capture and detection. The antibodies were raised against native human TTR protein. Pooled human serum was purchased from Innovative Research Inc. (Catalog #IPLA-SER, Lot #24453).

Pooled human serum and MAD serum samples were thawed at 37° C. in a water bath for 10 minutes. All samples were diluted 1:10000 in two steps. First 5 µL of serum was mixed with 995 µL of 1× diluent provided in ELISA kit. Second, 5 µL of the mixture was added to 245 µL of 1× diluent in a non-binding microplate. 100 µL of each final diluted sample was added to each well of the ELISA plate. All standards and samples were tested in duplicate. The TTR study follows the manufacturer's protocol from this point forward without any further modifications. Briefly, standards and serum samples were incubated in the ELISA plate for one hour at room temperature. The ELISA plate is washed four times with 1× wash buffer, then incubated with 1× horseradish peroxidase conjugate for 30 minutes at room temperature and protected from light. The ELISA plate is then washed four times. TMB substrate is added and allowed to develop for 10 minutes before adding stop solution. Finally, the absorbance at 450 nm is measured for each well.

The absorbance measurements were reference corrected by taking the average absorbance at 450 nm of the duplicate 0 ng/mL wells and subtracting it from the total 450 nm absorbance of each well.

Figure 25:
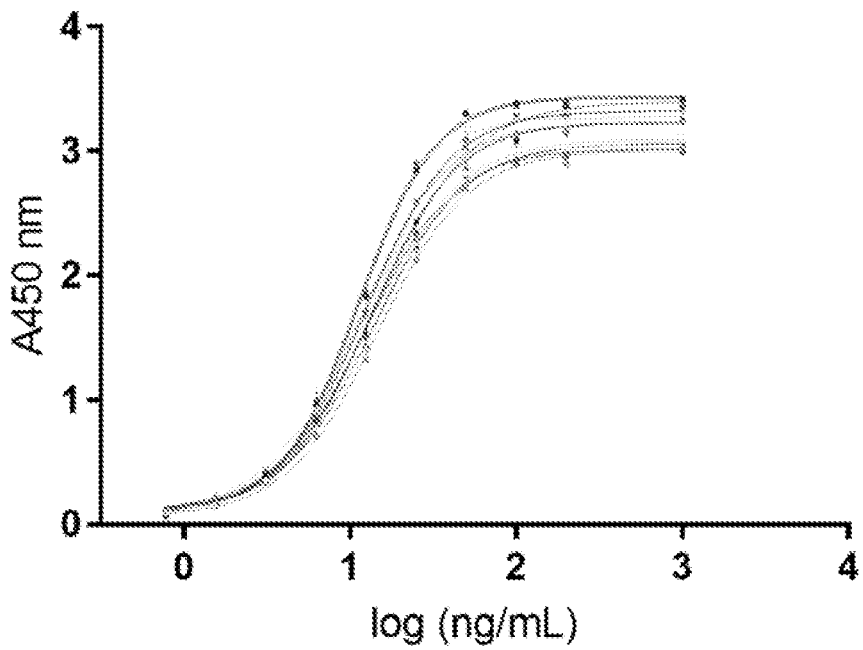
FIG. 25 shows the standard calibration curves generated using the Prealbumin ELISA kit (human) from Aviva Systems Biology.

A standard curve was generated for each ELISA plate using GraphPad PRISM software. The log (ng/mL) of the standards were plotted on the X axis and the reference corrected 450 nm absorbance values were plotted on the Y axis. The data were fit using a sigmoidal 4 parameter curve. The log (ng/mL) of the pooled human serum and MAD serum samples were interpolated from the standard curves. The log (ng/mL) values were transformed into serum TTR concentrations in mg/L and corrected for sample dilution. The standard curves generated using the supplied calibrant were reproducible (FIG. 25) and the kit successfully differentiated pooled human serum samples at increasing dilution ratios from 1:5000 to 1:20000. The Aviva ELISA kit was thus used for testing.

Figure 26:
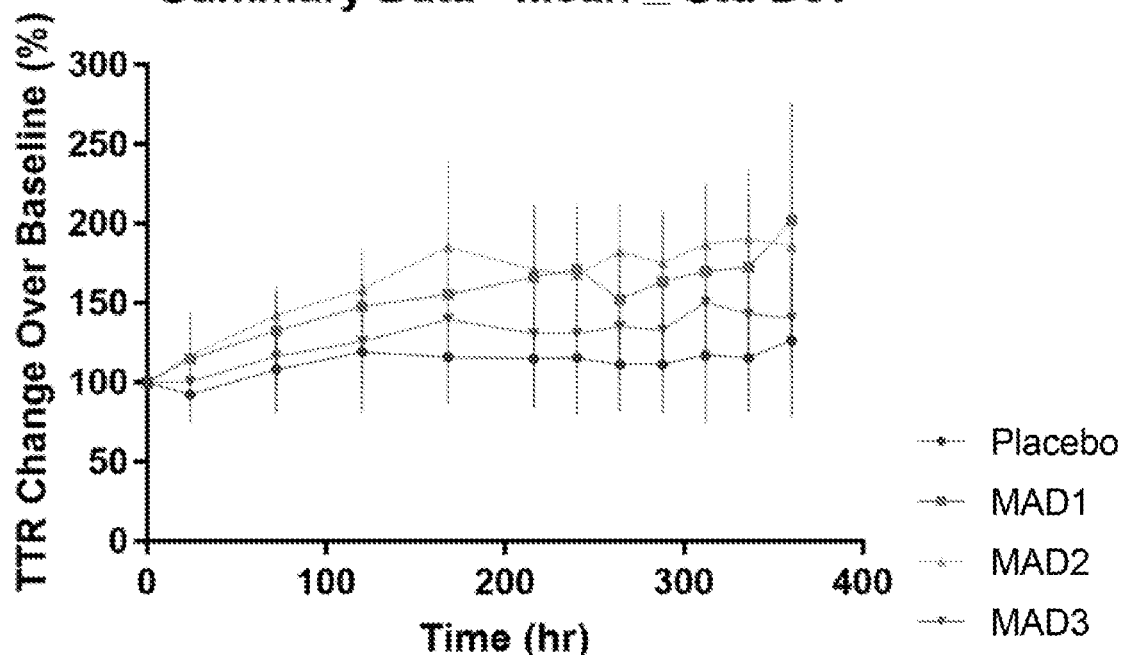
FIG. 26 shows the relative change in TTR concentration over time for each MAD cohort (Total number of Healthy Volunteers Dosed=24; Placebo:Active=1:3; MAD1 cohort=100 mg Q12h for 12 days; MAD2 cohort=300 mg Q12h for 12 days; MAD3 cohort=800 mg Q12h for 12 days). The change was calculated by normalizing against baseline values.
Figure 27:
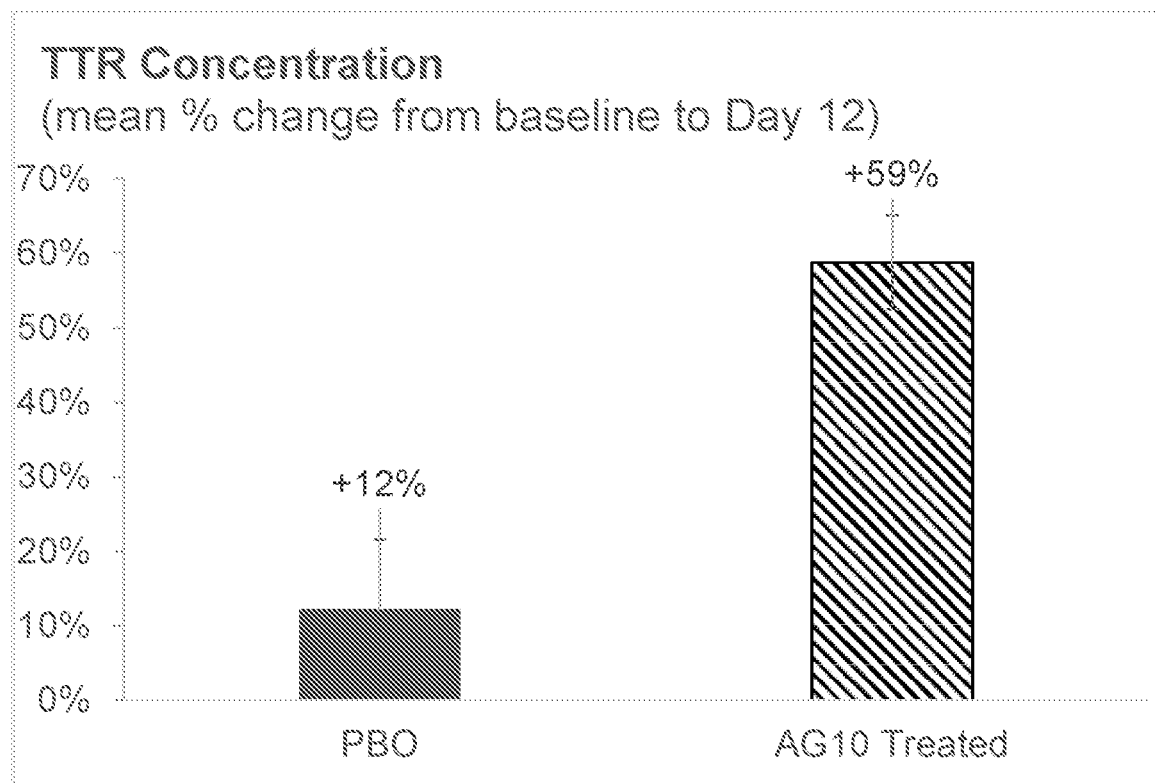
FIG. 27 illustrates the mean percent change in blood serum TTR concentration from baseline to Day 12 in all placebo and AG10 treated MAD subjects.
Figure 28:
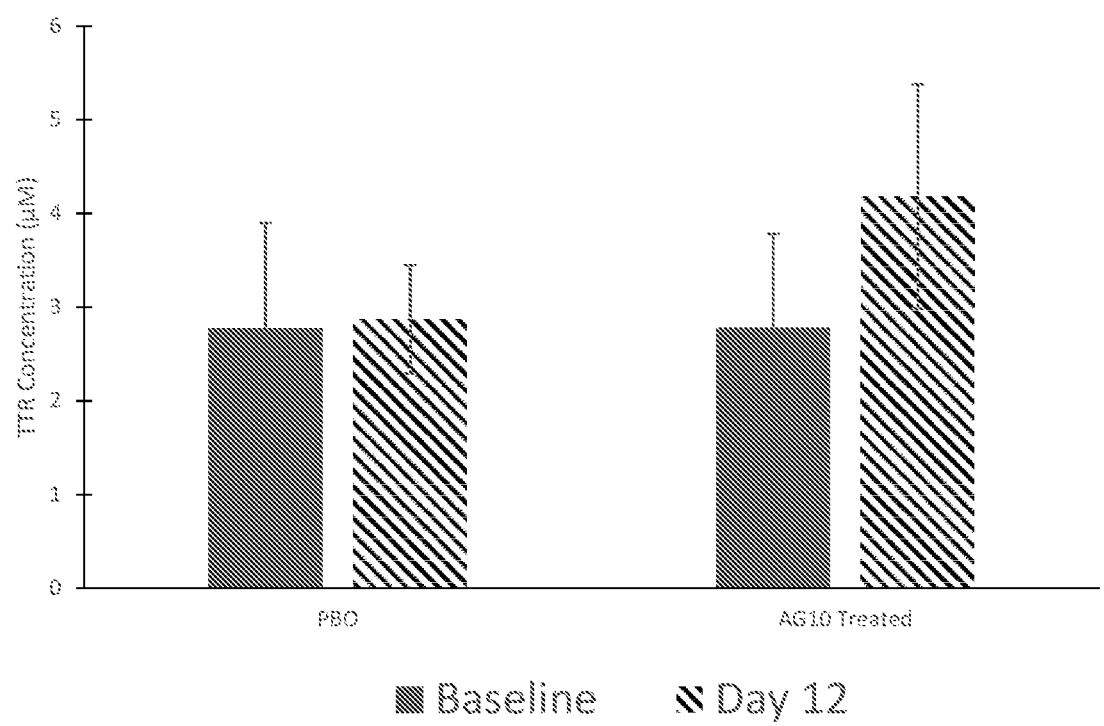
FIG. 28 plots the baseline and day 12 blood serum TTR concentration in all placebo and AG10 HCl treated cohorts (Total number of Healthy Volunteers Dosed=24; Placebo: Active=1:3; MAD1 cohort=100 mg Q12h for 12 days; MAD2 cohort=300 mg Q12h for 12 days; MAD3 cohort=800 mg Q12h for 12 days).
Figure 29:
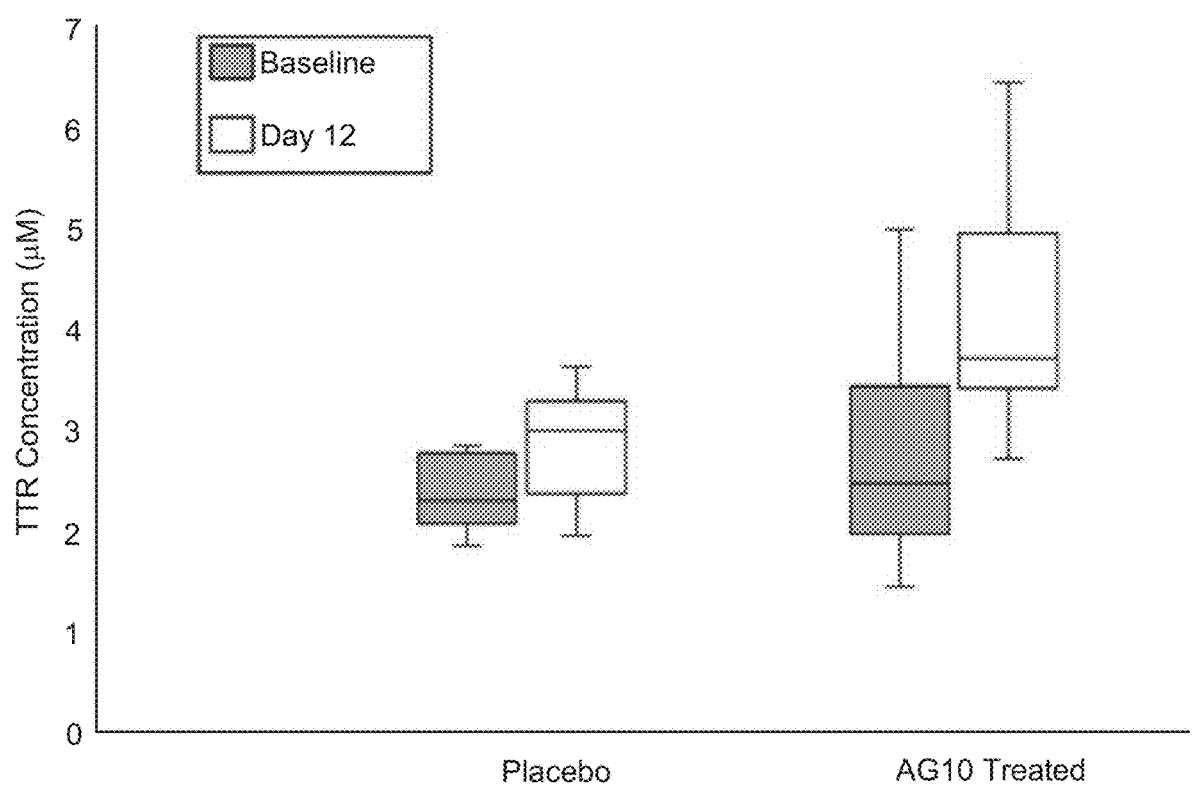
FIG. 29 plots the baseline and day 12 blood serum TTR concentration in all placebo and AG10 treated cohorts (Total number of Healthy Volunteers Dosed=24; Placebo:Active=1:3; MAD1 cohort=100 mg Q12h for 12 days; MAD2 cohort=300 mg Q12h for 12 days; MAD3 cohort=800 mg Q12h for 12 days).

Human normal volunteer samples from three cohorts of the MAD study (100, 300, 800 mg AG10 HCl dosed twice daily for twelve consecutive days) as well as placebo cohorts were tested using the Aviva ELISA kit. The relative change in TTR concentration over time for each cohort was calculated by normalizing against baseline values (FIG. 26). FIG. 27 shows the mean percent change in blood serum TTR concentration from baseline to Day 12 in all placebo and AG10 treated cohorts. FIG. 28 and FIG. 29 plot the baseline and day 12 blood serum TTR concentration in all placebo and AG10 HCl treated cohorts (Total number of Healthy Volunteers Dosed=24; Placebo:Active=1:3; MAD1 cohort=100 mg Q12h for 12 days; MAD2 cohort=300 mg Q12h for 12 days; MAD3 cohort=800 mg Q12h for 12 days).

ARUP Prealbumin Assay (Immunoturbidimetry Assay)

An ARUP Prealbumin assay was also used to analyze TTR blood serum concentration in the MAD cohorts tested. ARUP analyzes samples for prealbumin using the prealbumin reagent kit provided by Roche Diagnostics and run on the Roche Diagnostics c702 module. Lowest reportable limit is 3 mg/dL.

Table 6 summarizes the baseline and post dose (after 24 hours) blood serum TTR concentration measured for each cohort. In each tested group, there is a measurable increase in TTR concentration over the 24 h measurement period.

TABLE 6

MAD Cohorts 1-3 PK Parameters -- Blood Serum TTR Concentration

| Treatment | Baseline (mg/dL) | Postdose (mg/dL) | Change from Baseline (mg/dL) |
|---|---|---|---|
| 100 mg AG10 HCl (fasted) | 25.1 (17.2) [n = 6] | 28.0 (14.5) [n = 6] | 2.63 (38.9) [n = 6] |
| 300 mg AG10 HCl (fasted) | 21.8 (22.9) [n = 6] | 23.7 (16.4) [n = 6] | 2.64 (38.7) [n = 6] |
| 800 mg AG10 HCl (fasted) | 26.8 (15.2) [n = 6] | 29.0 (13.0) [n = 6] | 2.71 (28.4) [n = 6] |
| Placebo (pooled fasted) | 24.5 (12.5) [n = 6] | 23.5 (13.9) [n = 6] | . |

100 mg AG10 HCl (fasted): Administration of multiple oral doses of 100 mg AG10 HCl following an 8 hour fast
300 mg AG10 HCl (fasted): Administration of multiple oral doses of 300 mg AG10 HCl following an 8 hour fast
800 mg AG10 HCl (fasted): Administration of multiple oral doses of 800 mg AG10 HCl following an 8 hour fast
Placebo (pooled fasted): Administration of placebo following an 8 hour fast
Geometric mean change from baseline for placebo was set to missing since only 1/6 subjects had positive values and were included in the calculation. The remainder of subjects (5/6) were excluded due to negative change from baseline results.
. = Value missing or not reportable
Baseline, postdose and change from baseline values are presented as geometric mean and geometric CV%.

Example 7: Phase 2 Clinical Study Results—Individuals with ATTR-CM

The phase 2 clinical study was performed essentially as described in Example 3. A total of 49 patents were included instead of 45: 16 receiving 400 mg bid; 16 receiving 800 mg bid; and 17 receiving placebo.

Baseline characteristics for the individuals participating in the study are shown in Table 7, below.

TABLE 7

Baseline Characteristics

| Characteristic | Placebo N = 17 | AG10 HCl 400 mg N = 16 | AG10 HCl 800 mg N = 16 | Total N = 49 |
|---|---|---|---|---|
| Age, mean (range) | 73.2 (60-85) | 73.8 (60-83) | 75.4 (67-86) | 74.1 (60-86) |
| Male, n (%) | 17 (100%) | 14 (88%) | 14 (88%) | 45 (92%) |
| ATTRm, n (%) | 3 (18%) | 6 (37%) | 5 (31%) | 14 (29%) |
| ATTRwt, n (%) | 14 (82%) | 10 (63%) | 11 (69%) | 35 (71%) |
| Race, n (%) | | | | |
| White | 13 (76%) | 10 (63%) | 12 (75%) | 35 (72%) |
| Black | 3 (18%) | 4 (25%) | 3 (19%) | 10 (20%) |
| Other | 1 (6%) | 2 (12%) | 1 (6%) | 4 (8%) |

TABLE 7-continued

Baseline Characteristics

| Characteristic | Placebo N = 17 | AG10 HCl 400 mg N = 16 | AG10 HCl 800 mg N = 16 | Total N = 49 |
|---|---|---|---|---|
| NT-proBNP (pg/mL)[1] | 3151 ± 3705 | 3589 ± 3020 | 3377 ± 2806 | 3368 ± 2789 |
| Troponin I (ng/mL)[2] | 0.17 ± 0.30 | 0.22 ± 0.24 | 0.10 ± 0.06 | 0.16 ± 0.22 |
| TTR (mg/dL)[3] | 23.4 ± 5.5 | 23.2 ± 5.7 | 19.5 ± 4.2 | 22.0 ± 5.4 |

Results

TTR stabilization was measured ex vivo using the FPE and Western blot assays described at the beginning of the examples section. TTR stabilization was measured in vivo by monitoring TTR serum concentrations in trial participants.

Figure 30:
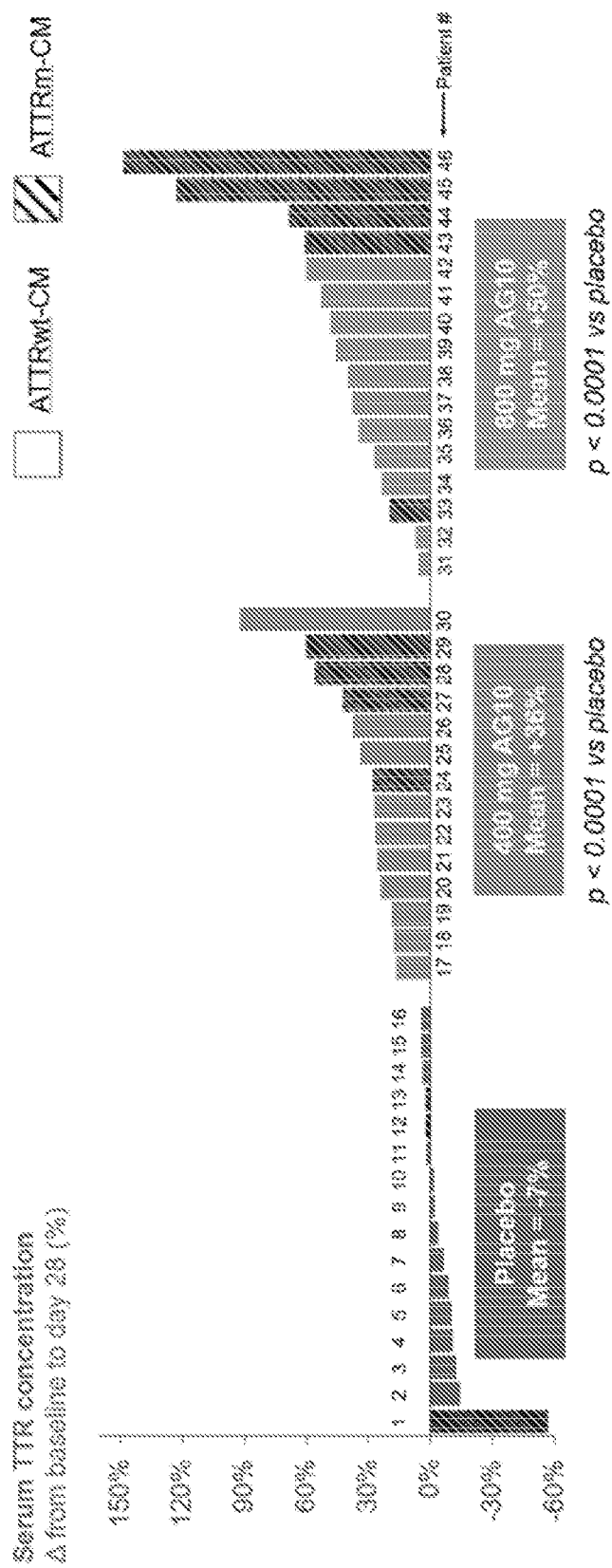
FIG. 30 illustrates the dose-response change in serum TTR levels for subjects in each treatment group. The data is reported as the percent change from baseline to day 28.

FIG. 30 illustrates the dose-response change in serum TTR levels for subjects in each treatment group. The data is reported as the percent change from baseline to day 28. Individuals receiving 400 mg of AG10 HCl twice a day had a mean increase in serum TTR levels of 36%, and individuals receiving 800 mg of AG10 HCl twice a day had a mean increase in serum TTR levels of 50%. Comparatively, the placebo treatment group had a mean decrease in serum TTR levels of 7%.

Figure 31:
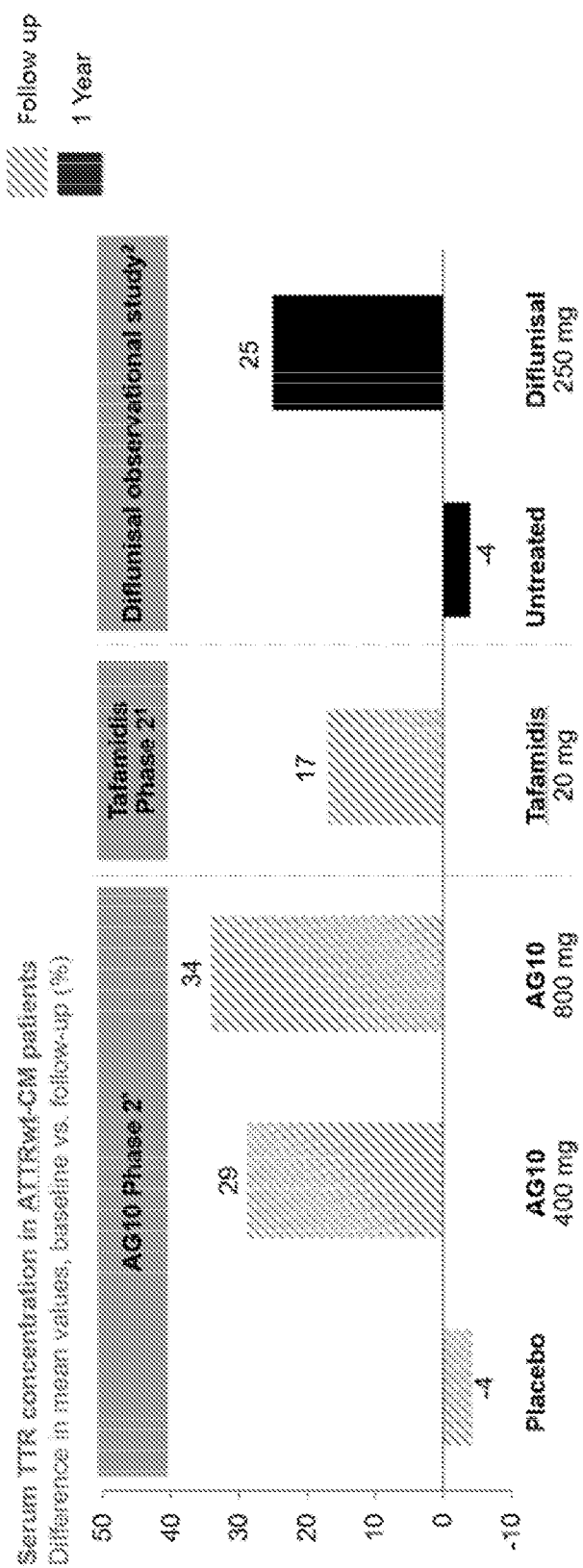
FIG. 31 shows that AG10 and TTR stabilizers Tafamidis and difusinal all increase TTR serum concentrations. The reported TTR serum concentrations for ΔG10 cohorts are after 28 days of treatment. The reported TTR serum concentration of Tafamidis is a 28 day interpolation based on reported 2-week and 6-week values. The reported TTR serum concentrations of Diflunisal is after 1 year of treatment.

The increase in serum TTR levels in the AG10 HCl dosing groups (both 400 mg and 800 mg b.i.d.) tracks the previously reported observation for TTR stabilizers previously tested. FIG. 31 plots the mean percent change from baseline to day 28 of dosing for each treatment group in this study. Also plotted is the percent change in serum TTR levels reported for Tafamidis Phase 2 (FDA CDER Advisory Committee Meeting background package) and a diflunisal observational study (Hanson, J. L. S. et al. Circ Heart Fail 2018 11:e004000). As can be seen in the figure, AG10, Tafamidis, and diflunisal all increased serum TTR levels.

Figure 32:
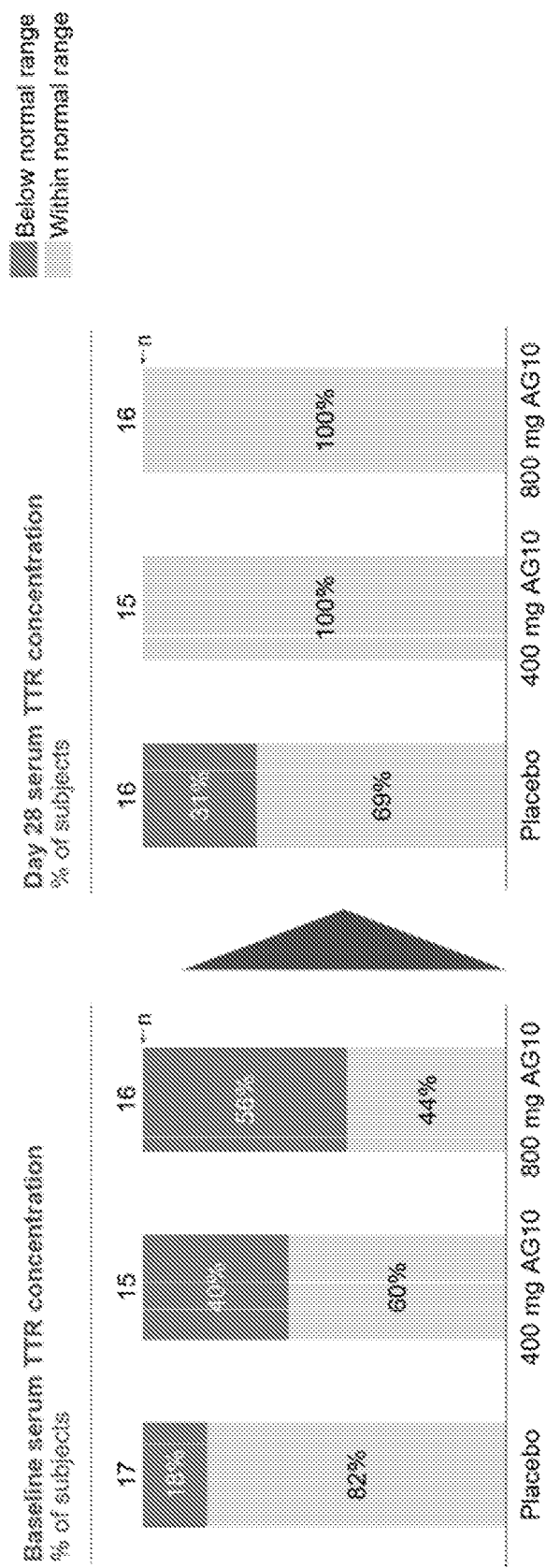
FIG. 32 shows that AG10 treatment restores low TTR levels to the normal range in ATTR-CM patients. The percent of ATTR-CM patients in each treatment group (placebo, 400 mg b.i.d., and 800 mg b.i.d.) that express low and normal levels of serum TTR concentration are reported before treatment (left hand side) and after 28 days of treatment (right hand side).
Figure 33:
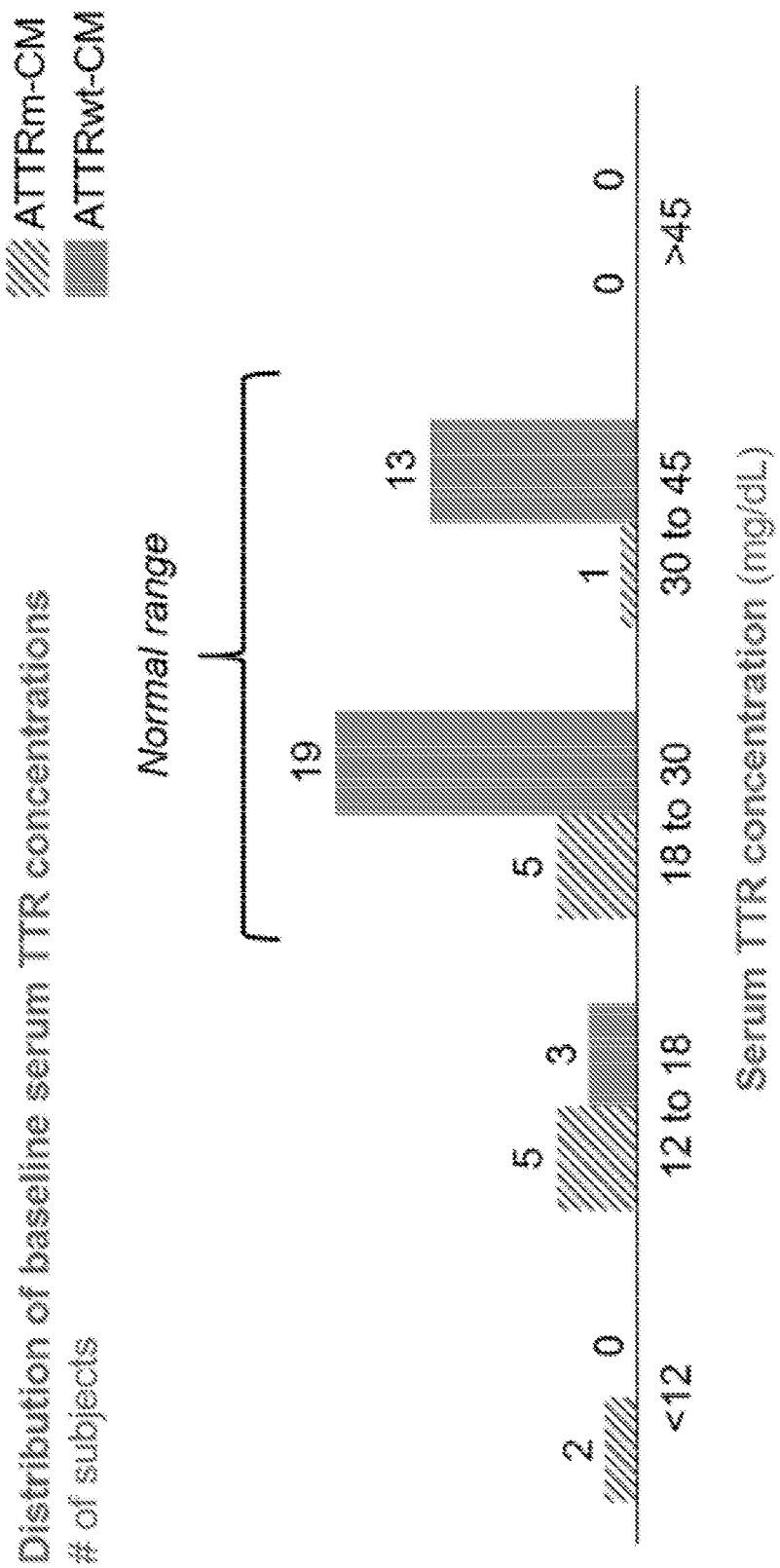
FIG. 33 plots the distribution of baseline serum TTR concentrations of each individual participating in the phase 2 study.

Before treatment 40% of subjects in the 400 mg b.i.d. treatment group, and 56% of subjects in the 800 mg b.i.d. treatment group had serum TTR levels that were below normal TTR levels (normal levels of TTR is 20-40 mg/dL (3.6-7.3 µM)). After 28 days of treatment, 100% of each active cohort had serum TTR concentrations within normal range (i.e., all treated patients had normal serum TTR levels by the end of the 28 day treatment regimen). Comparatively, 18% of placebo individuals had serum TTR levels that were below normal TTR levels before treatment. After 28 days of treatment, that number increased to 31% of placebo individuals who did not have normal levels of serum TTR concentration. See, FIG. 32. The baseline distribution of serum TTR concentrations for the individuals in the study is shown in FIG. 33.

Figure 34:
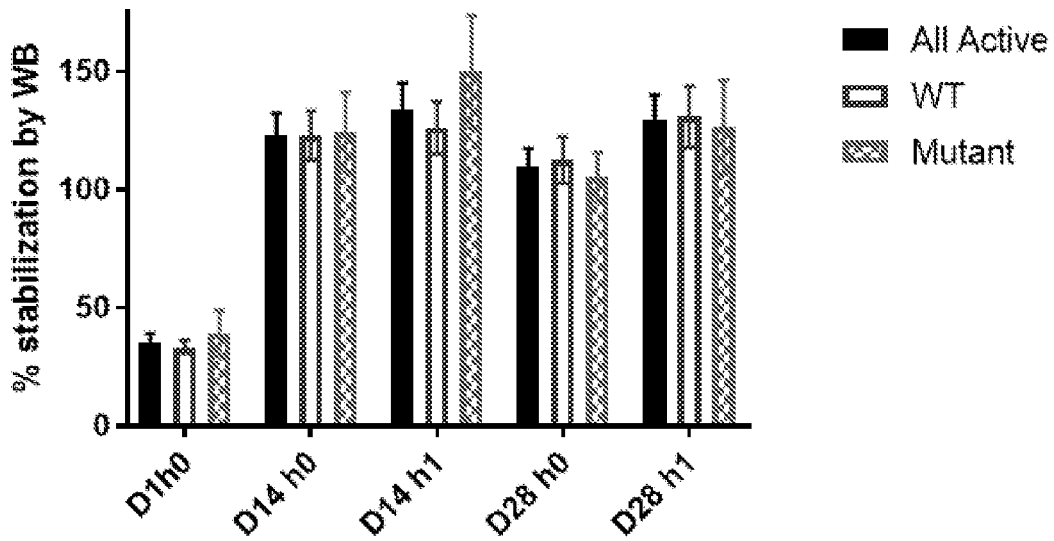
FIG. 34 illustrates the percent stabilization of TTR as determined by western blot assay for evaluating stabilization of tetrameric TTR. The data provided is for all individuals in the study (left column), individuals with WT TTR (middle column), and individuals with mutant TTR (right column). Error bars provided are the standard error of the mean.

Ex vivo western blot analysis confirms that each of the dosing levels of AG10 HCl, 400 mg b.i.d. and 800 mg b.i.d., effectively stabilized TTR. See, FIG. 34, illustrating high levels of TTR stabilization the day 14 and 28 trough (h0) and peak (h1) time points as compared to low levels of stabilization at the pre-dose time point (D1 h0). Error bars provided are the standard error of the mean.

Figure 35:
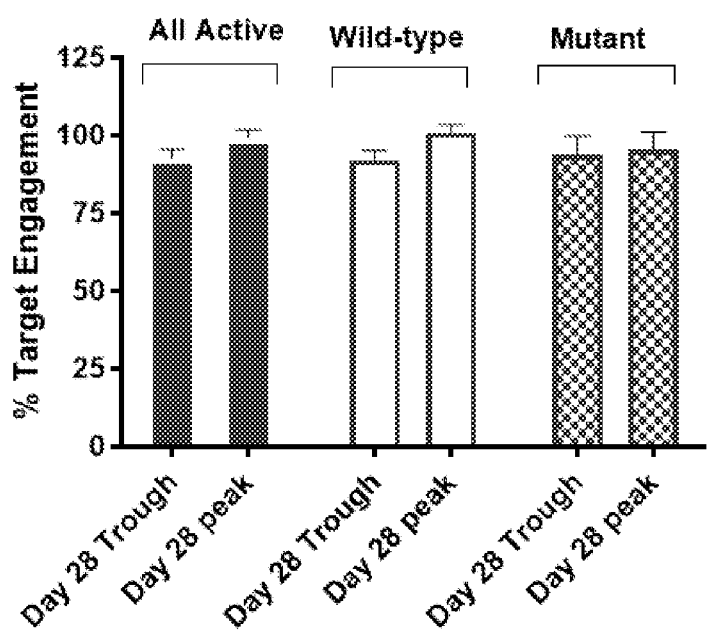
FIG. 35 illustrates the % occupancy of AG10 as determined by the fluorescence probe assay at the day 28 trough (pre-dose) and day 28 peak (1 hour after dose). The data provided is for all individuals in the study (filled columns), individuals with WT TTR (white columns), and individuals with mutant TTR (checkered columns).

This western blot result is further confirmed by the fluorescence probe assay, which shows high levels of TTR stabilization at the day 28 trough (pre-dose) and day 28 peak (1 hr after dose) in individuals with both wild-type and mutant TTR. See, FIG. 35.

Figure 36:
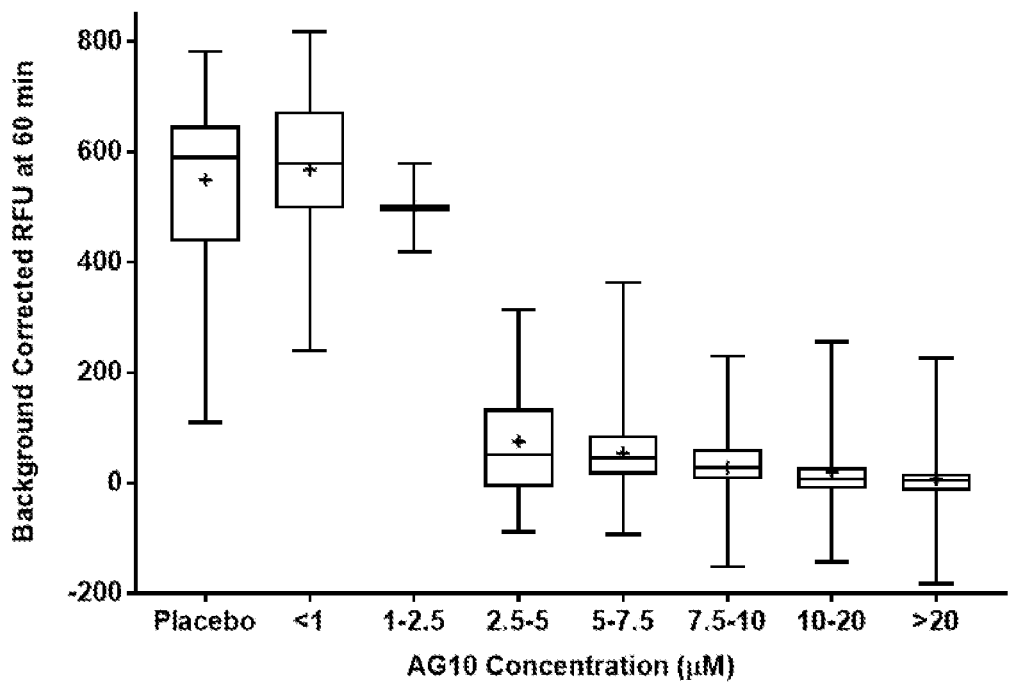
FIG. 36 plots the relationship between fluorescence probe binding and the concentration of AG10 in blood plasma. When the florescent probe is bound to TTR, the probe fluorescence is measured, when the fluorescent probe cannot bind to TTR, due to the occupancy of AG10, no fluorescence is measured.

When plotting the relationship between AG10 circulating blood plasma concentration and occupancy by AG10 in the thyroxine binding pocket of tetrameric TTR, it was determined that significant target engagement (occupancy by AG10) occurs around a blood plasma concentration of 5 µM and full target engagement occurs at about 7.5 µM. See, FIG. 36.

Figure 37:
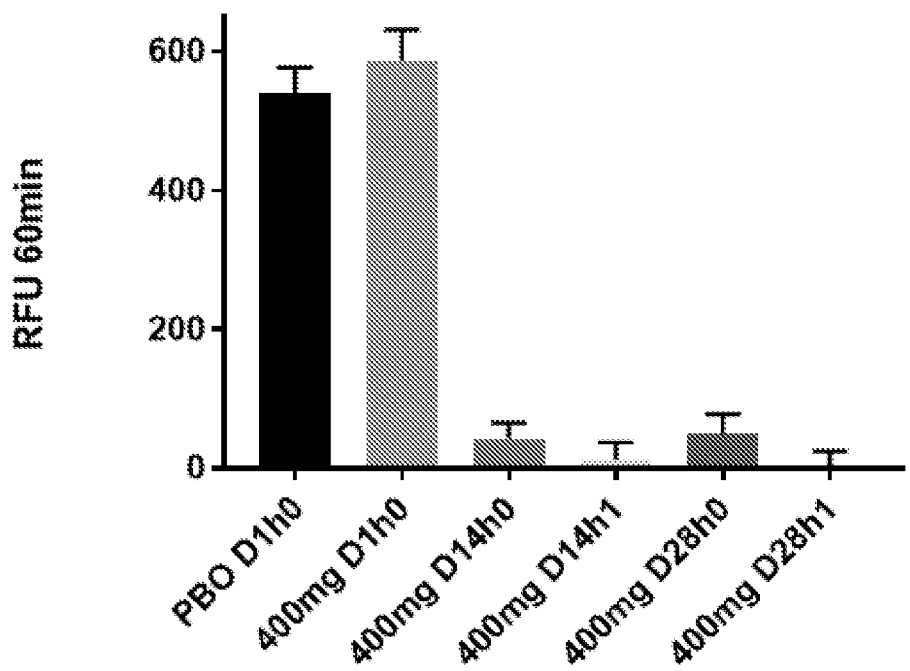
FIG. 37 plots the relative fluorescence units measured in the fluorescent probe assay at the indicated time points. Pre-dose is the trough level, while 1 hour pose dose is the peak level. The y-axis represents the mean value of 60 minute relative fluorescence units corrected for background. The data present is from individuals receiving 400 mg AG10 HCl salt b.i.d.
Figure 38:
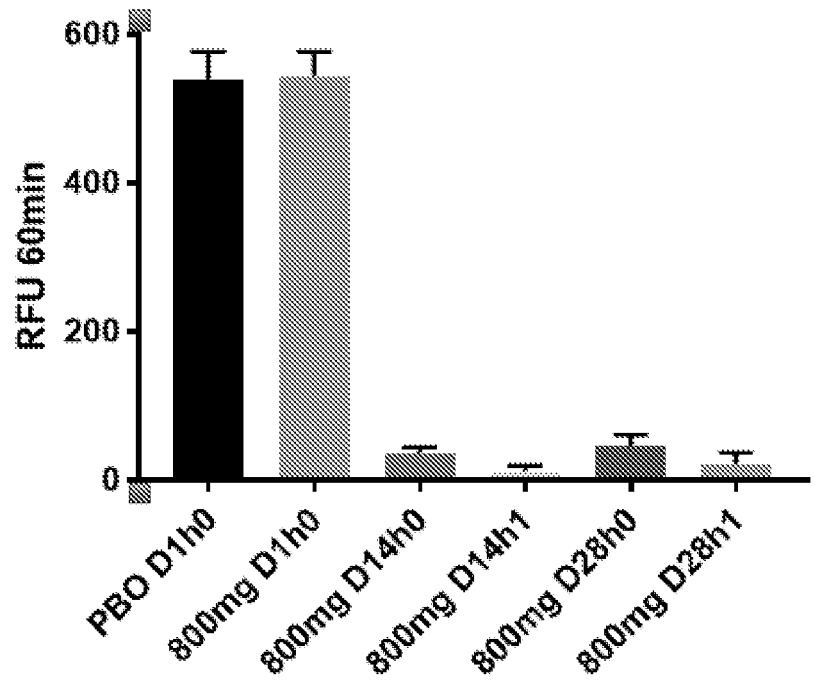
FIG. 38 plots the relative fluorescence units measured in the fluorescent probe assay at the indicated time points. The y-axis represents the mean value of 60 minute relative fluorescence units corrected for background. Pre-dose is the trough level, while 1 hour pose dose is the peak level. The data present is from individuals receiving 800 mg of AG10 HCl salt b.i.d.
Figure 39:
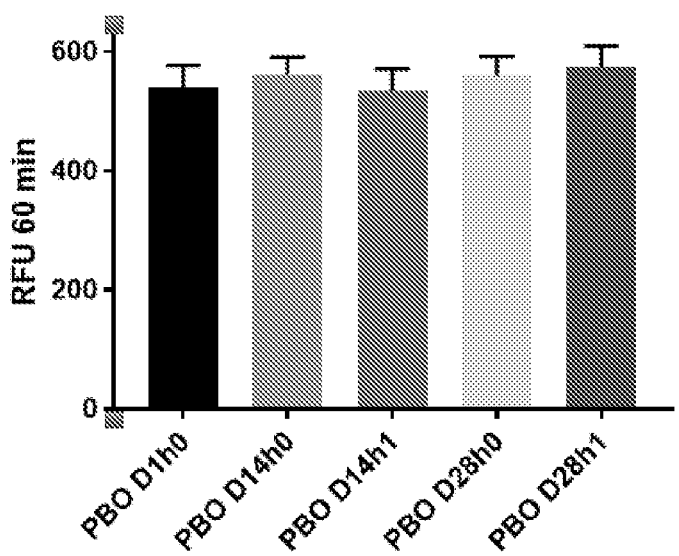
FIG. 39 plots the relative fluorescence units measured in the fluorescent probe assay at the indicated time points. The y-axis represents the mean value of 60 minute relative fluorescence units corrected for background. Pre-dose is the trough level, while 1 hour pose dose is the peak level. The data present is from individuals receiving placebo treatment.

FIG. 37 and FIG. 38 plot the relative fluorescence units measured at day 1 pre-dose, day 14 pre-dose (trough), day 14 1 hour post dose (peak), day 28 pre-dose (trough), and day 28 1 hr post-dose (peak) for the 400 mg b.i.d. cohort (FIG. 37) and the 800 mg b.i.d. cohort (FIG. 38) in the fluorescence probe assay. As can be seen in both figures, the fluorescence probe assay indicates that there is near full target engagement by day 14 in both the 400 mg b.i.d. and 800 mg b.i.d. cohorts at both the trough and peak time points. Comparatively, FIG. 39 plots the relative fluorescence units measured at each of the above referenced time points in the placebo control group. This plot demonstrates lack of target engagement for the placebo control group.

Collectively, the data presented herein indicated that AG10 was well tolerated in symptomatic ATTR-CM patients for 28 days, AG10 increases serum TTR concentrations in a dose-dependent manner, AG10 restores low TTR levels to normal levels, and AG10 completely stabilizes TTR across the both dosing levels tested.

When looking at wild-type and particular mutant TTR populations in the cohorts tested, each active dosing group—regardless of TTR genotype—showed an increase in blood serum TTR concentrations at the end of dosing as compared to the starting levels. The TTR blood serum data was analyzed using the ARUP Prealbumin assay described in Example 6 and is shown in Table 8 below.

TABLE 8

Blood Serum TTR Concentration in Phase II Cohorts

| Genotype | N | Average Change | Std Dev |
| --- | --- | --- | --- |
| 400 mg | 16 | 36% | 21% |
| T60A | 2 | 42% | 20% |
| V122I | 4 | 51% | 13% |
| WT | 10 | 32% | 22% |
| 800 mg | 16 | 50% | 38% |
| V122I | 4 | 90% | 57% |
| V30M | 1 | 61% | NA |
| WT | 11 | 35% | 18% |
| Placebo | 17 | −7% | 15% |
| V122I | 3 | −17% | 34% |
| WT | 14 | −4% | 7% |

Figure 40:
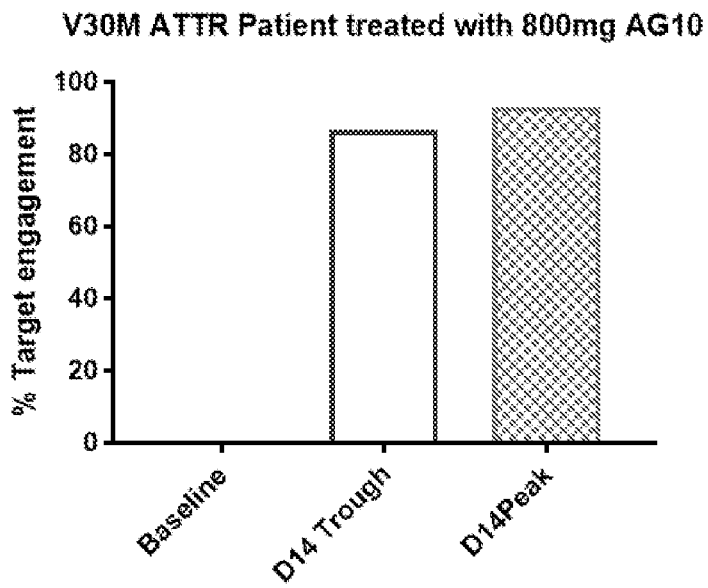
FIG. 40 illustrates the % occupancy of AG10 as determined by the fluorescence probe assay at the day 14 trough (pre-dose) and day 14 peak (0.5 hour after dose). The data provided is for an individual in the 800 mg b.i.d dosing group. AG10 HCl treatment group with a TTR protein having a V30M mutation.
Figure 41:
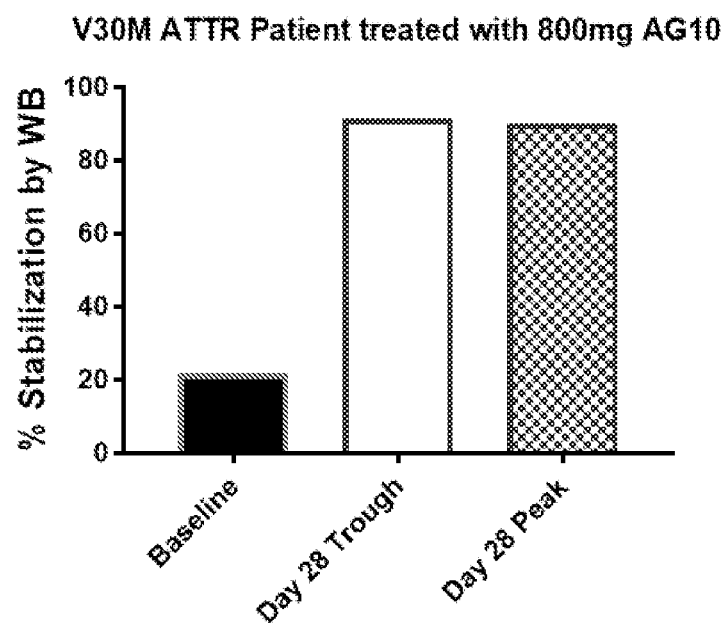
FIG. 41 illustrates the percent stabilization of TTR as determined by western blot assay for evaluating stabilization of tetrameric TTR. The data provided is for an individual in the 800 mg b.i.d. AG10 HCl treatment group with a TTR protein having a V30M mutation.

Specifically looking at the data for individuals with a V30M TTR mutation (a highly prevalent mutation associated with familial ATTR polyneuropathy (ATTRm-PN), near complete target engagement at day 14 and near complete TTR stabilization at day 28 of treatment was observed for this patient population using the FPE and western blot assays, respectively. See, FIG. 40 and FIG. 41.

Example 8: Commonly Used Diuretics do not Interfere with Exposure of AG10

ATTR-CM patients with clinical evidence of heart failure often manifest signs and symptoms of volume overload or elevated intracardiac pressure. This requires treatment with diuretics (*Ruberg & Berk Circulation* 2012 126:1286-300). Diuretics such as Furosemide or Torsemide were the most common medications used in the AG10-201 Phase 2 study in ATTR-CM patients. See, Table 9.

TABLE 9

Summary of Subjects Receiving Diuretic Treatment

| Dose | Total #of subjects | Subjects with Furosemide/Torsemide |
| --- | --- | --- |
| Placebo | 17 | 14 |
| 400 mg BID AG10 | 16 | 14 |
| 800 mg BID AG10 | 16 | 11 |

For Population PK analysis, a formal 3-step covariate selection process was employed to investigate their impact on AG10 Pharmacokinetics. While multiple covariates were identified as significant during forward addition, only disease state on central volume of distribution was found to be insignificant during the backward elimination at the significance level of α=0.01. Thus, the final model retained disease state on the central volume of distribution.

Population PK analysis was used to determine if co-administration of diuretics like furosemide had any impact on the pharmacokinetics of AG10. Of the 32 subjects in Phase 2 who were dosed with AG10, 25 were being treated with furosemide or torsemide. Of the 17 subjects who were on placebo, 14 were on furosemide or torsemide.

Figure 42A:
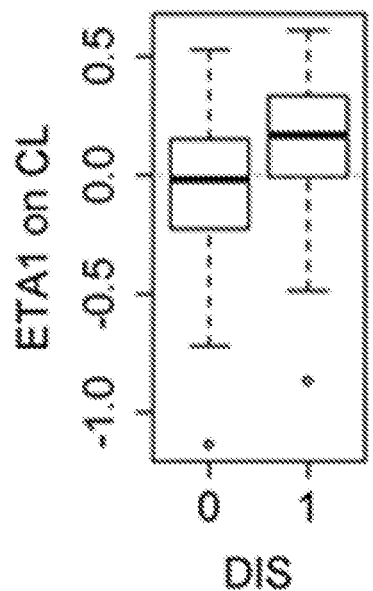
FIG. 42A-D plots Random Effects (ETA) vs. Categorical Covariate Plots in a Population PK Model. Panels A and B plot the effect on clearance, while Panels C and D plot the effect on volume. In the plots labeled "DIS" (Panel A and C) 0=healthy volunteers, 1=diseased subjects. In the plots labeled "ConMed 1" (Panel B and D) 0=Subjects received either Furosemide or Torsemide, 1=Patients did not receive either Furosemide or Torsemide. DIS: 0 (n=42)=All AG10 treated healthy adult volunteers from AG10-001 (SAD and MAD). 1 (n=32)=These are all active ATTR-CM patients from AG10-201 who were included in the population PK analysis. 16 in 400 mg bid group and 16 in 800 mg bid group. ConMed 1: 0 (n=49)=Subjects not receiving concomitant diuretics: Furosemide or Torsemide (42 healthy adult volunteers, 7 ATTR-CM patients) 1 (n=25)=subjects receiving either Furosemide or Torsemide.
Figure 42B:
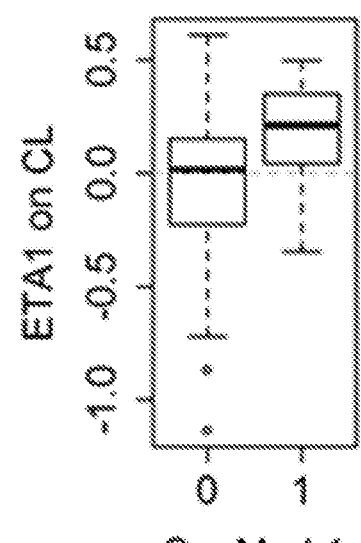

No difference in clearance of AG10 was observed between healthy adult volunteers in Phase 1 and subjects in Phase 2 based on patient status or diuretics (furosemide/torsemide) (FIG. 42A,B).

Figure 42C:
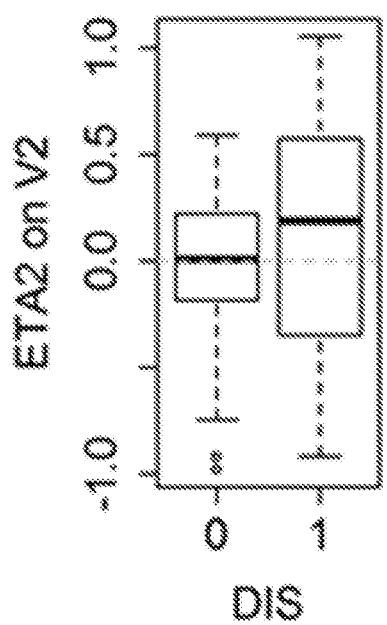
Figure 42D:
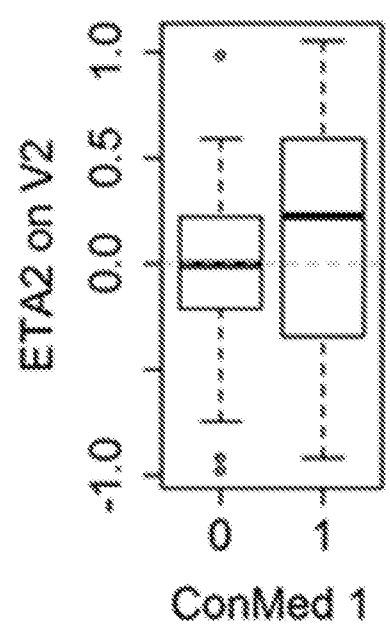
Figure 43:
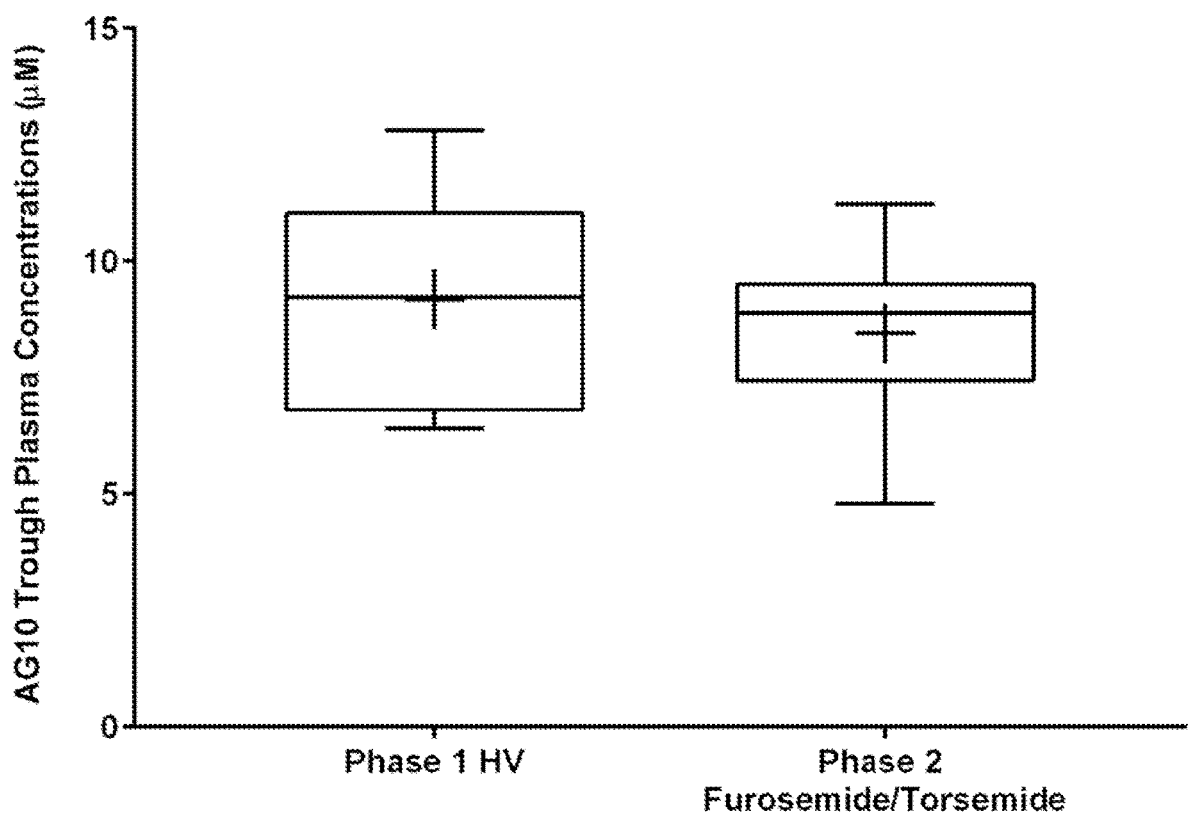
FIG. 43 plots the comparison of trough levels of AG10 on Day 12 from MAD 3 (Study AG10-001) to trough level in ATTR-CM patients dosed with 800 mg BID (AG10-201). Box and whiskers plot shows $25^{th}$ to $75^{th}$ percentile of results with whiskers spanning smallest to highest value in each group. Line denotes median and + denotes mean. Both studies used 200 mg AG10 tablets for dosing.

As previously stated, central volume of distribution was affected by disease state of ATTR-CM. Lower volume (FIG. 42C,D) was observed in:
  a) ATTR-CM patients in Phase 2 vs healthy adult volunteers in Phase 1
  b) ATTR-CM patients receiving furosemide or torsemide vs not receiving furosemide or torsemide Thus, volume of distribution was lower in subjects on furosemide/torsemide as compared to healthy adult volunteers. No distinction could be made between a drug-disease interaction (i.e., the effects of chronic heart failure on volume of distribution) and a drug-drug interaction (the effect of diuretics on volume of distribution). A variation in volume of distribution mainly affects the peak plasma concentration of a drug. Both Phase 1 (AG10-001) healthy adult volunteer study (MAD 3, 800 mg Q12h) and Phase 2 in ATTR-CM patients (AG10-201) have demonstrated that a circulating trough concentration of ~8 µM AG10 is a suitable target based on stabilization of TTR. As shown in FIG. 43, 800 mg bid dosing of AG10 attains suitable concentrations in both patients treated with furosemide or torsemide and in subjects who are not on concomitant diuretics.

Figure 44:
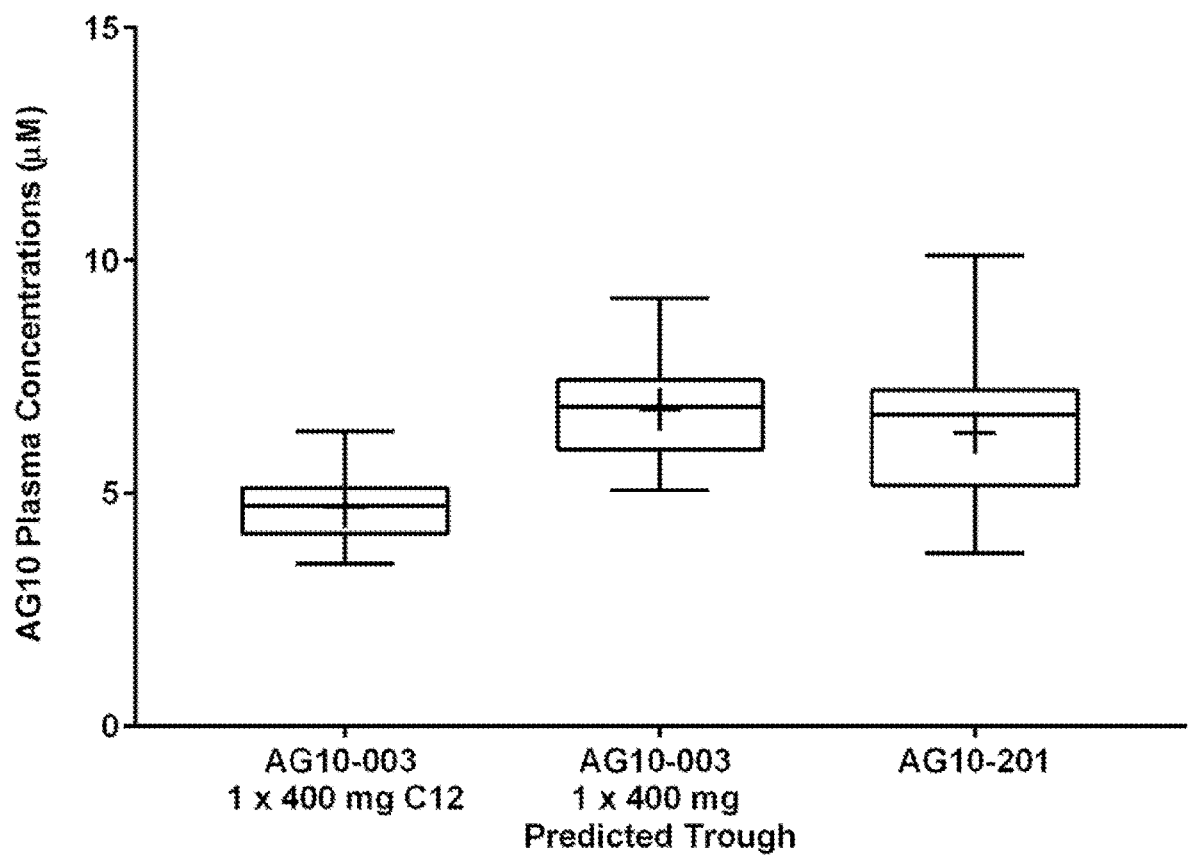
FIG. 44 plots the comparison of trough levels of AG10 in healthy subjects treated with 400 mg tablets with trough level in ATTR-CM patients dosed 400 mg BID from AG10-201. Box and whiskers plot shows $25^{th}$ to $75^{th}$ percentile of results with whiskers spanning smallest to highest value in each group. Line denotes median and + denotes mean. The healthy volunteer study (AG10-003) used 400 mg AG10 tablets for dosing and Phase 2 study AG10-201 used 200 mg tablets for dosing.

Mean accumulation ratios for plasma AG10 $C_{max}$ in repeat dosing of healthy volunteers ranged from 1.3 to 1.6. The accumulation ratio was used to predict pharmacokinetic profile of dosing AG10 400 mg tablets at steady state. FIG. 44 compares plasma level of AG10 12 hours after administration of single 400 mg AG10 tablet, predicted trough steady state circulating concentration of AG10, assuming an accumulation ratio of 1.45 (post repeat dosing of 400 mg tablets) and actual circulating concentrations of AG10 in ATTR-CM patients dosed with AG10 400 mg BID in Phase 2. Analogous to the results obtained with daily 800 mg BID dose (4×200 mg AG10 tablets twice daily), the predicted trough levels with the higher dose strength tablet (400 mg) also matched trough profile of the Phase 2 lower daily dose group of 400 mg BID (2×200 mg AG10 tablets twice daily).

Thus, commonly used diuretics do not interfere with exposure of AG10.

Example 9: Phase 3 Clinical Study—ATTR-CM

This prospective, randomized, multicenter, parallel-group study will evaluate the efficacy and safety of AG10 in symptomatic subjects compared to placebo, administered on a background of stable heart failure therapy. Screening and randomization will be followed by a total of 30 months of blinded, placebo-controlled treatment. At the end of 12 months of treatment (Part A) efficacy of AG10 will be assessed through analyses of the functional (6MWT) and health-related QoL (as measured by HF-specific instrument KCCQ) endpoints. At the end of 30 months of treatment (Part B) efficacy of AG10 will be further assessed through analysis of all-cause mortality and CV-related hospitalization.

There are currently no approved therapies indicated for the treatment of ATTR-CM. No other investigational treatments or therapies used off-label or as nonprescription supplements for the treatment of ATTR-CM will be permitted. However, in the event that other therapies are granted regulatory approval with a specific indication for the treatment of ATTR-CM in one or more geographies during the conduct of the trial, there are several potential pathways for study subjects:

Subjects will be encouraged to remain in the trial for at least 12 months of blinded study therapy regardless of the availability of any approved, indicated products. If a subject chooses to exit the trial at any time they will be encouraged to complete an early termination visit and associated procedures.

Any study subject who has already completed at least 24 months of blinded study therapy and thereafter gains access to an approved, indicated product will be encouraged to remain in the trial and continue blinded study treatment even after initiating therapy with that product. Subjects initiating therapy with an approved indicated product and remaining in the trial should have an unscheduled visit with study assessments prior to initiation of the concomitant therapy.

All subjects who complete 30 months of blinded study therapy and the final assessments of the double-blind treatment period may be eligible to participate in an open label extension study of long-term AG10 treatment.

Eligible subjects will be randomized in a 2:1 ratio to AG10 800 mg or matching placebo administered orally BID. Subjects will be stratified at randomization based on whether they have wild-type ATTR-CM (ATTRwt-CM) or mutant ATTR-CM (ATTRm-CM) with a targeted minimum of 20% of subjects with ATTRm-CM. Every effort will be made to confirm TTR status (wild-type or a variant) by genotyping. In exceptional circumstances (when subject refuses to get genetic testing), approval can be requested from Medical Monitor or a designee to enroll a subject without a documented genotyping. If approved, and subject is enrolled in the study, such subject with unknown TTR status will be stratified in the "wild-type TTR" stratum. Subjects will also be stratified according to NT-proBNP level ($\leq$3000 vs >3000 pg/mL) and renal function defined by eGFR ($\geq$45 vs <45 mL/min/1.73 m$^2$) at Screening.

Samples for plasma PK and serum/plasma PD will be collected in the PopPK-PD substudy.

Information on AEs and concomitant medications will be collected throughout the study. The safety and conduct of the study will be monitored by an independent Data Monitoring Committee (DMC).

Figure 45:
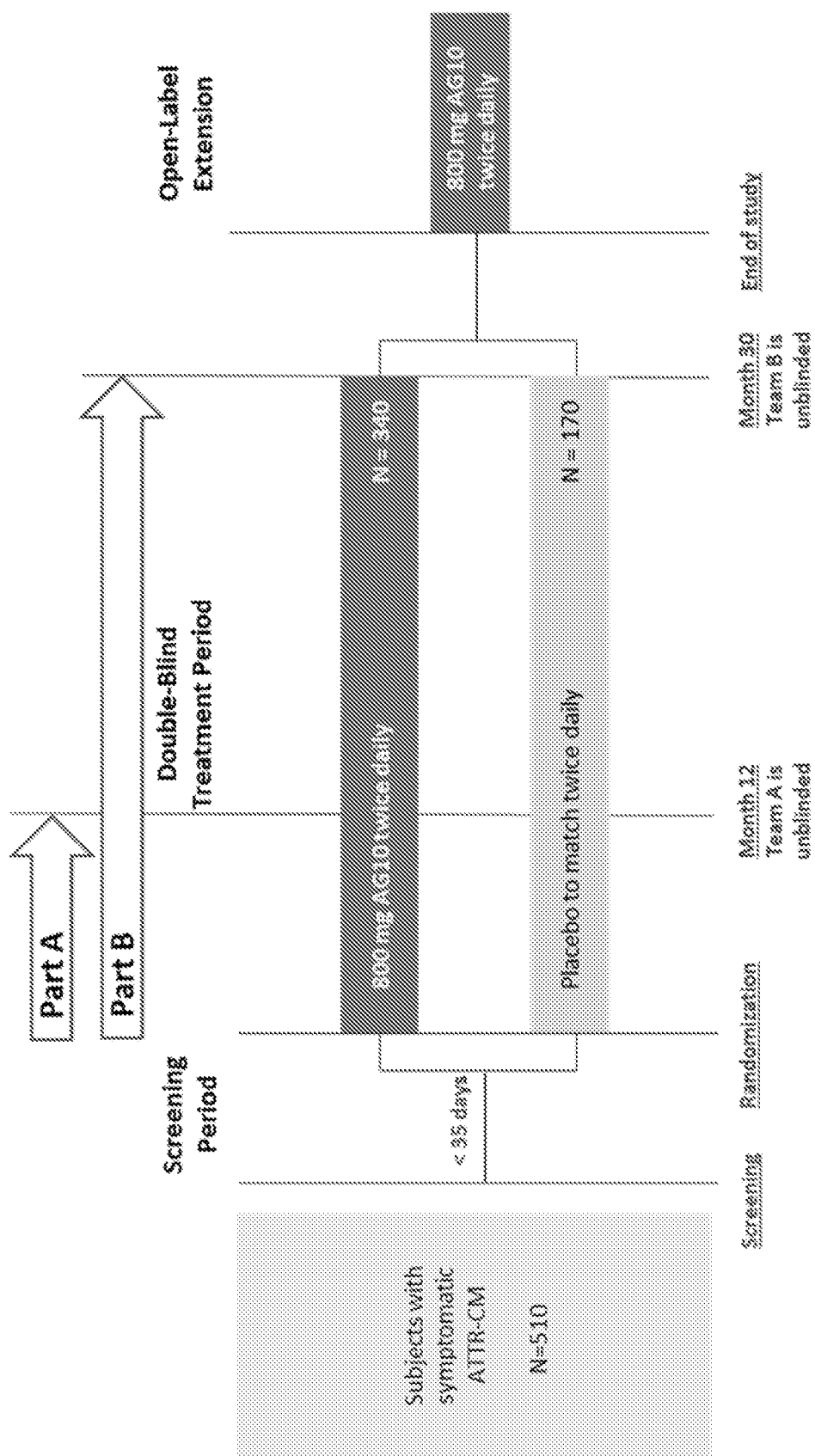
FIG. 45 displays a summary of the trial design for the Phase 3 clinical study in subjects with ATTR-CM.

A summary of the trial design is shown in FIG. 45.

Part A of this study will determine the efficacy of AG10 in the treatment of subjects with symptomatic transthyretin amyloid cardiomyopathy (ATTR-CM) by evaluating the difference between the AG10 and placebo groups in the change from baseline in the Six-Minute Walk test (6MWT) after 12 months of treatment.

Part B of this study will determine the efficacy of AG10 in the treatment of subjects with symptomatic ATTR-CM by evaluating the difference between the AG10 and placebo groups in the combined endpoint of All-Cause Mortality and the cumulative frequency of cardiovascular (CV)-related hospitalization over a 30-month period.

Subject Population and Stratification

Approximately 510 males and females $\geq$18 and $\leq$90 years of age with chronic, stable, symptomatic (NYHA Class I-III) ATTR-CM will be randomized in a 2:1 ratio (340 subjects to active treatment, 170 to matching placebo) in the study. Subjects will be stratified at randomization according to whether they have ATTRm-CM or ATTRwt-CM with a targeted minimum of 20% of subjects with ATTRm-CM. Every effort will be made to confirm TTR status (wild-type or a variant) by genotyping. In exceptional circumstances (when subject refuses to get genetic testing), approval can be requested from Medical Monitor or a designee to enroll a subject without a documented genotyping. If approved, and subject is enrolled in the study, such subject with unknown TTR status will be stratified in the "wild-type TTR" stratum. Subjects will also be stratified according to NT-proBNP level ($\leq$3000 vs >3000 pg/mL) and renal function defined by eGFR ($\geq$45 vs <45 mL/min/1.73 m$^2$) at Screening.

Duration of Treatment

Subjects will be treated with the study drug (AG10 or placebo) for 30 months unless it is not well tolerated. Eligible subjects who complete 30 months of treatment may continue to an OLE to receive AG10, at the discretion of the Investigator.

Part A, Part B and the OLE will be reported separately. The trial is complete after data for all subjects completing a post treatment final visit have been included in the final database and a final report of the trial has been completed.

Treatments Administered

Subjects who meet eligibility criteria will be randomized in a 2:1 manner (AG10: placebo) to receive the following treatment arms in a double-blind fashion:

800 mg AG10 BID, orally (two 400 mg AG10 tablets, BID)

Matching placebo BID, orally (two matching placebo tablets, BID)

In the event that the Investigator determines that a dose adjustment is warranted, based on a subject's report of AEs that may indicate the study medication is not well tolerated, the blinded dose may be decreased to 400 mg AG10 or matching placebo administered BID. This will be accomplished by having the study staff instruct the subject to take one tablet of study medication BID instead of two. Any dose adjustment will be documented in the database.

Prohibited Medications

1. Use of patisiran, inotersen, tafamidis [see Note below] or any other investigational agent for the treatment of ATTR-CM is prohibited during the study.

2. Use of diflunisal, doxycycline; natural products or derivatives used as unproven therapies for ATTR-CM (e.g., green tea extract, tauroursodeoxycholic acid [TUDCA]/ursodiol is prohibited.
3. Use of calcium channel blockers (e.g., verapamil, diltiazem) or *digitalis* is prohibited.

Note: If, during participation in the study, tafamidis becomes commercially available and subjects have access to it, subjects will be permitted to initiate therapy with tafamidis as a concomitant medication if they have completed at least 24 months of blinded study therapy.

Study Procedures
Schedule of Assessments

The descriptions of the procedures to be performed throughout the study are provided below.

Screening (Day −35 to Day −1)

Screening will be performed within 35 days before administration of the first dose of IMP. The following procedures will be performed at Screening:
- Informed consent administration
- Review Inclusion/Exclusion criteria to confirm subject is eligible
- Submission of source documents required for the Diagnostic Confirmation Committee should be completed as early as possible during the Screening period and must include either:
  1. endomyocardial biopsy report; OR
  2. planar Images of a positive $^{99m}$Tc-pyrophosphate or -bisphosphonate scan, AND clinical laboratory evidence excluding the diagnosis of AL amyloidosis (based on both immunofixation electrophoresis (IFE) of serum and/or urine, and serum free light chain (sFLC) analysis);

Note: subjects with concurrent monoclonal gammopathy of undetermined significance (MGUS) may require confirmation of the diagnosis of ATTR-CM by endomyocardial biopsy with mass spectrometric analysis.
- Medical and surgical history assessment
- NYHA Class assessment
- Physical examination including body weight and height measurements
- Vital signs assessment
- 12-lead resting ECG
- Resting transthoracic echocardiogram (ECHO), if LV wall (interventricular septum or LV posterior wall) thickness not documented in medical history based on echocardiogram or CMR
- Six-Minute Walk Test (6MWT), two assessments >24 hours to ≤2 weeks apart
- Blood sample collection for hematology, serum chemistry (including circulating biomarkers), urinalysis
- Blood sample collection for serum and plasma exploratory tests
- Urine pregnancy test, female subjects of child bearing potential only
- Prior medication use assessment Treatment Days Study procedures are listed below by study day, ideally performed in the order listed below, for each day.

Day 1 and Every 3 Months (±7 Days)

These assessments will occur at Day 1 and Months 3, 6, 9, 15, 18, 21, 24, and 27:
- Review Inclusion/Exclusion criteria to confirm subject is eligible (Day 1)
- Randomize subject to treatment arm and assign randomization number (Day 1)
- NYHA Class assessment
- Physical examination including body weight measurement
- Vital signs assessment
- 12-lead resting ECG
- Kansas City Cardiomyopathy Questionnaire (KCCQ)
- EuroQoL-5 Dimensions (EQ-5D-5L)
- Six-Minute Walk Test (6MWT), at Months 6, 9, 18, 24 (
- Blood sample collection for hematology, serum chemistry (including circulating biomarkers), urinalysis
- Urine pregnancy test, female subjects of child bearing potential only
- PD blood sample collection for analysis of TTR stabilization (predose) in PopPK-PD substudy
- PK blood sample collection (predose) in PopPK-PD substudy
- Prealbumin blood sample collection (predose)
- Dispense/collect and administer IMP with designated witness (i.e., site personnel)
- Concomitant medication use assessment
- AE/Vital status assessment/Hospitalization determination
- IMP compliance assessment (all visits except Day 1)

Day 28 (±3 Days)
- NYHA Class assessment
- Physical examination including body weight measurement
- Vital signs assessment
- 12-lead resting ECG, predose and at 1 hour postdose
- Blood sample collection for hematology, serum chemistry (including circulating biomarkers), urinalysis
- Urine pregnancy test, female subjects of child bearing potential only
- PD blood sample collection for analysis of TTR stabilization (predose and at 1 hour postdose) in PopPK-PD substudy
- PK blood sample collection (predose and at 1 hour postdose) in PopPK-PD substudy
- Prealbumin blood sample collection (predose)
- Dispense/collect and administer IMP with designated witness (i.e., site personnel)
- Concomitant medication use assessment
- AE/Vital status assessment/Hospitalization determination
- IMP compliance assessment Month 12 (±7 Days)
- NYHA Class assessment
- Physical examination including body weight measurement
- Vital signs assessment
- 12-lead resting ECG
- Kansas City Cardiomyopathy Questionnaire (KCCQ)
- EuroQoL-5 Dimensions (EQ-5D-5L)
- Six-Minute Walk Test (6MWT)
- Blood sample collection for hematology, serum chemistry (including circulating biomarkers), urinalysis
- Urine pregnancy test, female subjects of child bearing potential only
- PD blood sample collection for analysis of TTR stabilization (predose) in PopPK-PD substudy
- PK blood sample collection (predose) in PopPK-PD substudy
- Prealbumin blood sample collection (predose)
- Dispense/collect and administer IMP with designated witness (i.e., site personnel)
- Concomitant medication use assessment
- AE/Vital status assessment/Hospitalization determination
- IMP compliance assessment Monthly Telephone Contact (±7 Days)

These telephone contacts will occur at Months 2, 4, 5, 7, 8, 10, 11, 13, 14, 16, 17, 19, 20, 22, 23, 25, 26, 28, and 29:
  Concomitant medication use assessment
  AE/Vital status assessment/Hospitalization determination
  IMP compliance assessment If a subject discontinues study drug and study assessments, all efforts must be made to continue to follow the subject for the course of the study by completing monthly contact for vital status or until withdrawal of consent.

Month 30 (±7 Days) and Open Label Extension Start

Subjects who complete 30 months of double-blind treatment period will continue in the OLE to receive AG10.
  NYHA Class assessment
  Physical examination including body weight measurement
  Vital signs assessment
  12-lead resting ECG
  Kansas City Cardiomyopathy Questionnaire (KCCQ)
  EuroQoL-5 Dimensions (EQ-5D-5L)
  Six-Minute Walk Test (6MWT)
  Blood sample collection for hematology, serum chemistry (including circulating biomarkers), urinalysis
  Urine pregnancy test, female subjects of child bearing potential only
  PD blood sample collection for analysis of TTR stabilization (predose) in PopPK-PD substudy
  PK blood sample collection (predose) in PopPK-PD substudy
  Prealbumin blood sample collection (predose)
  Dispense/collect and administer IMP with designated witness (i.e., site personnel)
  Concomitant medication use assessment
  AE/Vital status assessment/Hospitalization determination
  IMP compliance assessment Month 1 Post Open Label Extension Start (±3 Days)
  NYHA Class assessment
  Physical examination including body weight measurement
  Vital signs assessment
  12-lead resting ECG
  Blood sample collection for hematology, serum chemistry (including circulating biomarkers), urinalysis
  Urine pregnancy test, female subjects of child bearing potential only
  PD blood sample collection for analysis of TTR stabilization (predose) in PopPK-PD substudy
  PK blood sample collection (predose) in PopPK-PD substudy
  Prealbumin blood sample collection (predose)
  Dispense/collect and administer IMP with designated witness (i.e., site personnel)
  Concomitant medication use assessment
  AE/Vital status assessment/Hospitalization determination
  IMP compliance assessment Every 3 Months Post Open Label Extension Start (±7 Days)
  NYHA Class assessment
  Physical examination including body weight measurement
  Vital signs assessment
  12-lead resting ECG
  Kansas City Cardiomyopathy Questionnaire (KCCQ)
  EuroQoL-5 Dimensions (EQ-5D-5L)
  Six-Minute Walk Test (6MWT), every 6 months
  Blood sample collection for hematology, serum chemistry (including circulating biomarkers), urinalysis
  Urine pregnancy test, female subjects of child bearing potential only
  PD blood sample collection for analysis of TTR stabilization (predose) in PopPK-PD substudy
  PK blood sample collection (predose) in PopPK-PD substudy
  Prealbumin blood sample collection (predose)
  Dispense/collect and administer IMP with designated witness (i.e., site personnel)
  Concomitant medication use assessment
  AE/Vital status assessment/Hospitalization determination
  IMP compliance assessment Drug Concentration Measurements PK Blood Draw Schedule In a subgroup of subjects at participating sites, PK samples will be collected at the following times to determine AG10 plasma concentrations:
  Day 1, and at every 3 months study visits: Predose
  Day 28: Predose and at 1 hour postdose
  Month 1 post OLE start and OLE every 3 months: Predose ET PD Blood Draw Schedule In a subgroup of subjects at participating sites, PD properties of AG10 will be assessed by established assays of TTR stabilization, including fluorescent probe exclusion (FPE) assay and Western blot. Sampling will be done at the following times to perform these PD assays:
  Day 1, and at every 3 months study visits: Predose
  Day 28: Predose and at 1 hour postdose
  Month 1 post OLE start and OLE every 3 months: Predose ET Prealbumin Blood Sampling Procedures Sampling to measure prealbumin concentrations will be done at the following times:
  Days 1, 28, and at every 3 months study visits: Predose
  Month 1 post OLE start and OLE every 3 months: Predose ET Six-Minute Walk Test (6MWT)

Prior to randomization, two 6MWTs will be conducted >24 hours to ≤2 weeks apart. The walking distances must be ≥150 meters and the distance walked must be within 15% on 2 consecutive tests on different days. If the 2 test results are not within the 15%, an additional 6MWT should be repeated within 24 hours to 2 weeks of one of the 6MWTs. If the last attempt is still not within 15% of one of the 6MWTs, the subject will not be eligible for participation.

The 6MWT should be conducted after completion of the KCCQ and EQ-5D-5L at the visits where required.

The 6MWT with Borg Scale will be conducted according to the guidelines of the American Thoracic Society. Complete details on the procedures for the 6MWT are provided in the Study Procedures Manual.

Kansas City Cardiomyopathy Questionnaire (KCCQ)

The KCCQ is a 23-item questionnaire developed to measure health status and health-related quality of life in subjects with heart failure. Items include heart failure symptoms, impact on physical and social functions, and how their heart failure impacts their quality of life (QoL). It should be completed by the subject at predose. Complete details are provided in the Study Procedures Manual.

EuroQoL-5 Dimensions (EQ-5D-5L)

EQ-5D-5L is a brief, self-administered generic health status instrument that takes about 5 minutes to complete and should be conducted after completion of the KCCQ. The instrument includes two parts. In the first part, respondents are asked to rate their current health state on 5 dimensions (mobility, self-care, usual activities, pain or discomfort, and anxiety or depression) with each dimension having five levels of function (1-no problem, 2-slight problem, 3-moderate problem, 4-severe problem, and 5-extreme problem). The second part is a respondents self-rating of current health status on a Visual Analog Scale (EQ VAS) with endpoints labeled "best imaginable health state" (score of 100) and "worst imaginable health state" (score of 0). The scores from the 5 dimensions may be used to calculate a single index value, also known as a utility score. Complete details administration and scoring are provided in the Study Procedures Manual.

Clinical Laboratory Determinations

Blood and urine samples for clinical laboratory tests will be collected. At Screening, the Investigator will assess the clinical significance of any values outside the reference ranges provided by the laboratory, and subjects with abnormalities judged to be clinically significant will be excluded from the study.

The following clinical laboratory tests will be performed:

| | |
|---|---|
| Hematology | Hemoglobin, hematocrit, white blood cell (WBC) count, platelet count, complete blood count (CBC), and differential |
| Chemistry | Sodium, potassium, chloride, carbon dioxide (bicarbonate), glucose, blood urea nitrogen (BUN), creatinine, aspartate aminotransferase (AST), alanine aminotransferase (ALT), total protein, albumin, prealbumin, retinol-binding protein (RBP), free thyroxine (FT4), alkaline phosphatase, calcium, phosphorus, total and fractionated (indirect or direct) bilirubin, uric acid, thyroid-stimulating hormone (TSH), troponin I, creatine kinase (CK), CK-MB, and NT- proBNP |
| Urinalysis | Complete urinalysis (specific gravity, pH, glucose, protein, hemoglobin, leukocyte esterase, and nitrite. Additionally, albumin to creatinine ratio and a microscopic urinalysis will be performed on every specimen and will specifically look for casts, bacteria, white blood cells, epithelial cells, and red blood cells |
| Others | Follicle-stimulating hormone (FSH) only to confirm postmenopausal status at Screening in female subjects who do not have menses for at least 12 months and are not using hormonal contraception or hormone replacement therapy. A postmenopausal state is defined as no menses for 12 months without an alternative medical cause. |
| Pregnancy test | Highly sensitive urine test at all visits as outlined in the Schedule of Assessments (female subjects of childbearing potential only) |

Vital Signs

Study center staff will assess vital signs pre- and postdose after a 5 minute rest. Any abnormal vital sign that is deemed clinically significant (i.e., is associated with symptoms and/or requires medical intervention) will be recorded as an AE.

Electrocardiograms

A standard 12-lead ECG will be assessed, ECGs will be performed in the supine position after a 5 minute rest at predose. The 1 hour postdose ECG on Day 28 will be conducted until additional Phase 1 data on the PK-PD relationship to QTc have been collected and analyzed. Based on the results of the PK-PD data, the 1 hour postdose ECG on Day 28 may no longer be required in order to reduce subject burden. All Investigators will be informed of this change through routine communication.

The Investigator or qualified Sub-Investigator will review all ECG interpretations and interval duration measurements for clinical significance. Any ECG interpretation deemed to be clinically significant (i.e., is associated with symptoms and/or requires medical intervention) will be reported as an AE.

Physical Examinations

Subjects will undergo a complete physical examination (PE) including body weight and height measurements, which is to be completed by a physician or an appropriately trained health professional. Any abnormal physical examination finding that is deemed clinically significant (i.e., is associated with symptoms and/or requires medical intervention) will be recorded as an AE.

Definition of CV-Related Hospitalization

Cardiovascular-related hospitalization is defined as non-elective admission to an acute care setting for medical therapy that results in at least 24 hours stay (or a date change if the time of admission/discharge is not available), or a hospital stay of less than 24 hours if the discharge diagnosis and interventions indicate that the purpose of the hospital stay was for intravenous diuretic therapy for management of decompensated heart failure. Investigator is responsible for ensuring potential study endpoints, including dates of admissions and discharge are collected and documented; providing Investigator assessment whether the hospitalization is CV-related; and submitting Adverse Event notification for all AEs that result in deaths or hospitalization.

Example 10: Phase 3 Clinical Study—ATTR-PN

This prospective, randomized, multicenter, parallel-group study will evaluate the safety and efficacy of AG10 in symptomatic subjects with ATTR-PN compared to placebo. Screening and randomization will be followed by an 18-month, double-blind, placebo-controlled treatment period.

Eligible subjects will be randomized in a 1:1 ratio to AG10 800 mg or matching placebo administered orally BID. Subjects will be stratified at randomization based on Screening Neuropathy Impairment Score (NIS) cutoff of <30 points and ≥30 points, and according to whether they are currently taking tafamidis (Vyndagel®, Pfizer) or not (in those countries or regions where it is available).

Information on AEs and concomitant medications will be collected throughout the study. The safety and conduct of the study will be monitored by an independent Data Monitoring Committee (DMC).

Figure 46:
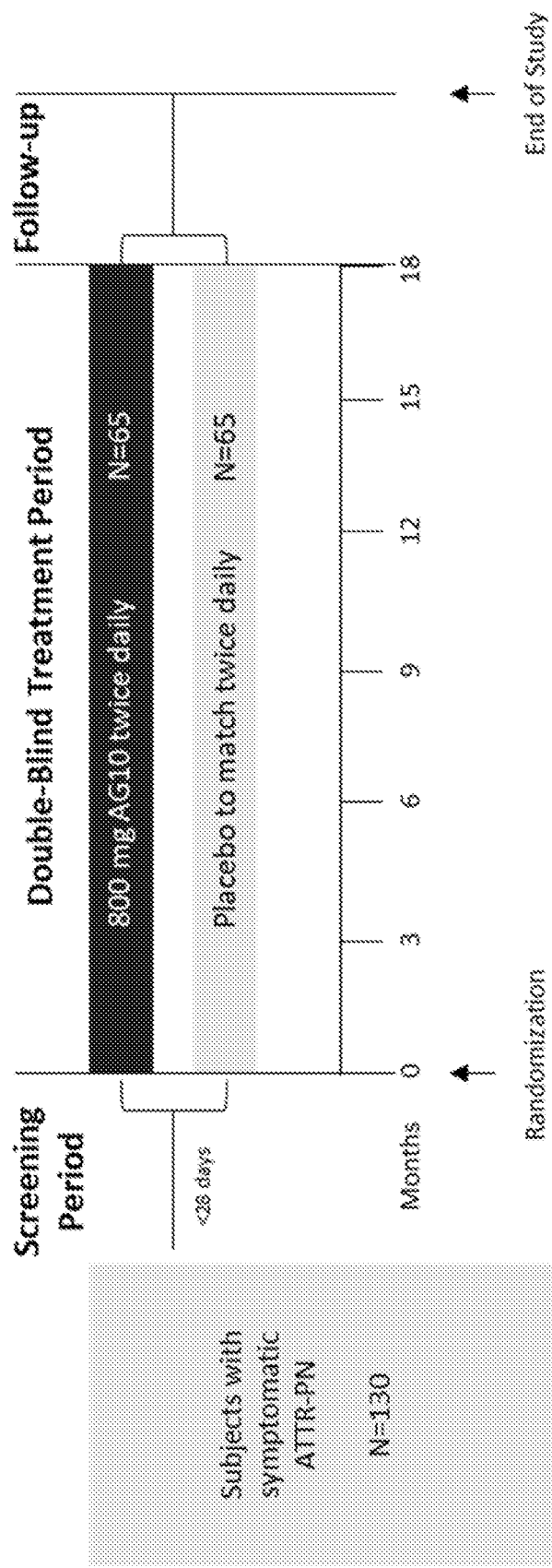
FIG. 46 displays a summary of the trial design for the Phase 3 clinical study in subjects with ATTR-PN.

A summary of the trial design is shown in FIG. 46.

Subject Population and Stratification

Documentation of a positive genotype is required to confirm an established diagnosis of ATTR-PN. Key eligibility criteria were selected to identify a subject population with disease sufficiently advanced to show progression in the placebo group, but not so advanced as to preclude detection of a change in disease status (e.g., PND score ≤IIIa and Karnofsky performance score ≥60%). As many patients with ATTR-PN also have cardiac involvement, subjects with NYHA Class IV symptoms are excluded given the high mortality associated with that degree of cardiomyopathy. Concomitant use of other therapies which modulate transthyretin production or stability are excluded (with the possible exception of tafamidis 20 mg/d, if available) to better clarify the efficacy and safety signals attributable to AG10.

The Neuropathy Impairment Score (NIS) is a neurological assessment that is relatively easy to administer representing a summation of clinical impairments (weakness, decrease in reflexes and sensory loss) using standard groups of muscles, reflexes and sensory modalities and specific sites. It is calculated on a scale of 0 to 244 with higher scores indicating worsening of disease. Because the NIS has been shown to correlate with other measures of disease severity and prognosis and because median values of ~30 have been reported in large cohorts of patients with ATTR-PN, stratification of NIS score at Screening (<30 and ≥30) is included to mitigate against potential imbalances in severity of neuropathy across treatment arms (Adams 2015). Subjects will also be stratified according to whether they are taking tafamidis 20 mg/d as indicated for the treatment of ATTR-PN in some countries or regions where it is available.

Duration of Treatment

Subjects will be treated with the study drug (AG10 or placebo) for 18 months.

Based on longitudinal assessment observed in several published cohorts, the rate of progression in this subject population at Month 18 would be expected to be ~12.5 to 17 points on the mNIS+7 (Adams 2017, Berk 2013). Because disease progression in placebo subjects as measured by mNIS+7 is gradual, a worsening of at least 12 points is expected over an 18 month trial duration (Adams 2017, Berk 2013). As AG10 is expected to halt disease progression by preventing ongoing amyloidogenesis, 18 months is likely to be sufficiently long to detect a clinically meaningful placebo-adjusted change in mNIS+7 scores.

Treatments Administered

Subjects will be randomized in a 1:1 manner (AG10: placebo) to receive the following treatment arms in a double-blind fashion:
  800 mg AG10 BID, orally (two 400 mg AG10 tablets, BID)
  Matching placebo BID, orally (two matching placebo tablets, BID)

In the event that the Investigator determines that a dose adjustment is warranted, based on a subject's report of AEs that may indicate the study medication is not well tolerated, the blinded dose may be decreased to 400 mg AG10 or matching placebo administered BID. This will be accomplished by having the study staff instruct the subject to take one tablet of study medication BID instead of two. Any dose adjustment will be documented in the database.

Prohibited Medications

1. Use of patisiran, inotersen, or any other approved or investigational agent for the treatment of ATTR-PN (other than tafamidis 20 mg dose) is prohibited during the study.
2. Use of approved products without an indication for the treatment of ATTR (e.g., diflunisal, doxycycline), or natural products or derivatives used as unproven therapies for ATTR (e.g., green tea extract, tauroursodeoxycholic acid [TUDCA]/ursodiol) is prohibited during the study.

Study Procedures

Schedule of Assessments

The descriptions of the procedures to be performed throughout the study are provided below.

Screening (Day −28 to Day −1)

Screening will be performed within 28 days before administration of the first dose of IMP. The following procedures will be performed at Screening:
  Informed consent administration
  Review Inclusion/Exclusion criteria to confirm subject is eligible
  Medical and surgical history assessment
  NYHA Class assessment
  Karnofsky performance status
  Physical examination including mBMI
  Vital signs assessment
  12-lead resting ECG
  PND score
  NIS
  mNIS+7
  10-meter Walk Test (10MWT), two assessments >24 hours to <1 week apart
  Blood sample collection for hematology, serum chemistry (including circulating biomarkers), urinalysis
  Blood sample collection for serum and plasma exploratory tests
  Urine pregnancy test, female subjects of child bearing potential only
  Prior medication use assessment Treatment Days Study procedures are listed below by study day, ideally performed in the order listed below, for each day.

Day 1 and Every 3 Months (±7 Days)

These assessments will occur at Day 1 and Months 3, 6, 9, 15:
  Review Inclusion/Exclusion criteria to confirm subject is eligible (Day 1)
  Randomize subject to treatment arm and assign randomization number (Day 1)
  NYHA Class assessment
  Physical examination including mBMI
  Vital signs assessment
  12-lead resting ECG
  PND score
  Dyck/Rankin score
  mNIS+7
  Norfolk QOL-DN
  COMPASS-31
  10-meter Walk Test (10MWT)
  Blood sample collection for hematology, serum chemistry (including circulating biomarkers), urinalysis
  Urine pregnancy test, female subjects of child bearing potential only
  PD blood sample collection for analysis of TTR stabilization (predose)
  PK blood sample collection (predose)
  Prealbumin blood sample collection (predose)
  Dispense/collect and administer IMP with designated witness (i.e., site personnel)
  Concomitant medication use assessment
  AE/Vital status assessment
  IMP compliance assessment (all visits except Day 1)

Month 18 (±7 Days)
  NYHA Class assessment
  Physical examination including mBMI
  Vital signs assessment
  12-lead resting ECG
  PND score
  Dyck/Rankin score
  mNIS+7
  Norfolk QOL-DN
  COMPASS-31
  10-meter Walk Test (10MWT)
  Blood sample collection for hematology, serum chemistry (including circulating biomarkers), urinalysis
  Urine pregnancy test, female subjects of child bearing potential only
  PD blood sample collection for analysis of TTR stabilization (predose)
  PK blood sample collection (predose)
  Prealbumin blood sample collection (predose)
  Dispense/collect and administer IMP with designated witness (i.e., site personnel)
  Concomitant medication use assessment
  AE/Vital status assessment
  IMP compliance assessment Monthly Telephone Contact (±7 Days)

These telephone contacts will occur at Months 2, 4, 5, 7, 8, 10, 11, 13, 14, 16, 17:

Concomitant medication use assessment

AE/Vital status assessment

IMP compliance assessment

If a subject discontinues study drug and study assessments, all efforts must be made to continue to follow the subject for the course of the study by completing monthly contact for vital status or until withdrawal of consent.

Drug Concentration Measurements

PK Blood Draw Schedule

In a subgroup of subjects at participating sites, PK samples will be collected at the following times to determine AG10 plasma concentrations:

Day 1, and at every 3 months study visits: Predose

PD Blood Draw Schedule

In a subgroup of subjects at participating sites, PD properties of AG10 will be assessed by established assays of TTR stabilization, including fluorescent probe exclusion (FPE) assay and Western blot. Sampling will be done at the following times to perform these PD assays:

Day 1, and at every 3 months study visits: Predose

Prealbumin Blood Sampling Procedures

Sampling to measure prealbumin concentrations will be done at the following times:

Days 1, 28, and at every 3 months study visits: Predose

Assessments

The following assessments will be completed:

10-meter Walk Test (10MWT)

Neuropathy Impairment Score (NIS)

Modified Neurologic Impairment Score (mNIS+7)

COMPASS-31

Dyck/Rankin score

Nutritional status (calculated based on mBMI)

10-meter Walk Test (10MWT)

The 10MWT is a performance measure used to assess walking speed in meters per second over a short distance. It is employed to determine functional mobility, git, and vestibular function. Prior to randomization, two 10MWTs will be conducted >24 hours to <1 week apart.

Neuropathy Impairment Score (NIS)

The NIS is a neurological assessment that represents a summation of clinical impairments (weakness, decrease in reflexes and sensory loss) using standard groups of muscles, reflexes and sensory modalities and specific sites.

Modified Neurologic Impairment Score (mNIS+7)

The mNIS+7 nerve test is a composite scale to assesses, in part, muscle weakness, sensory loss, and decreased muscle stretch reflexes.

Composite Autonomic Symptom Score-31 (COMPASS-31)

The COMPASS-31 is used to quantify the impact of TTR amyloidosis on each subject's autonomic symptoms.

Dyck/Rankin Score

Quality of Life will be assessed using the Dyck/Rankin score.

Nutritional Status

Nutritional status will be assessed based on changes in mBMI.

Clinical Laboratory Determinations

Blood and urine samples for clinical laboratory tests will be collected. At Screening, the Investigator will assess the clinical significance of any values outside the reference ranges provided by the laboratory, and subjects with abnormalities judged to be clinically significant will be excluded from the study.

The following clinical laboratory tests will be performed:

| | |
|---|---|
| Hematology | Hemoglobin, hematocrit, white blood cell (WBC) count, platelet count, complete blood count (CBC), and differential |
| Chemistry | Sodium, potassium, chloride, carbon dioxide (bicarbonate), glucose, blood urea nitrogen (BUN), creatinine, aspartate aminotransferase (AST), alanine aminotransferase (ALT), total protein, albumin, prealbumin, retinol-binding protein (RBP), free thyroxine (FT4), alkaline phosphatase, calcium, phosphorus, total and fractionated (indirect or direct) bilirubin, uric acid, thyroid-stimulating hormone (TSH), troponin I, creatine kinase (CK), CK-MB, and NT- proBNP |
| Urinalysis | Complete urinalysis (specific gravity, pH, glucose, protein, hemoglobin, leukocyte esterase, and nitrite. Additionally, albumin to creatinine ratio and a microscopic urinalysis will be performed on every specimen and will specifically look for casts, bacteria, white blood cells, epithelial cells, and red blood cells |
| Others | Follicle-stimulating hormone (FSH) only to confirm post-menopausal status at Screening in female subjects who do not have menses for at least 12 months and are not using hormonal contraception or hormone replacement therapy. A postmenopausal state is defined as no menses for 12 months without an alternative medical cause. |
| Pregnancy test | Highly sensitive urine test at all visits as outlined in the Schedule of Assessments (female subjects of childbearing potential only) |

Vital Signs

Study center staff will assess vital signs pre- and postdose after a 5 minute rest. Any abnormal vital sign that is deemed clinically significant (i.e., is associated with symptoms and/or requires medical intervention) will be recorded as an AE.

Electrocardiograms

A standard 12-lead ECG will be assessed. ECGs will be performed in the supine position after a 5 minute rest at predose. The Investigator or qualified Sub-Investigator will review all ECG interpretations and interval duration measurements for clinical significance. Any ECG interpretation deemed to be clinically significant (i.e., is associated with symptoms and/or requires medical intervention) will be reported as an AE.

Physical Examinations

Subjects will undergo a complete physical examination (PE) including mBMI, which is to be completed by a physician or an appropriately trained health professional. Any abnormal physical examination finding that is deemed clinically significant (i.e., is associated with symptoms and/or requires medical intervention) will be recorded as an AE.

Karnofsky Scale

| | | |
|---|---|---|
| Able to carry on normal activity and to work; no special care needed. | 1100 | Normal no complaints; no evidence of disease. |
| | 990 | Able to carry on normal activity; minor signs or symptoms of disease. |
| | 880 | Normal activity with effort; some signs or symptoms of disease. |
| Unable to work; able to live at home and care for most personal needs; varying amount of assistance needed. | 770 | Cares for self; unable to carry on normal activity or to do active work. |
| | 660 | Requires occasional assistance, but is able to care for most of his personal needs |
| | 550 | Requires considerable assistance and frequent medical care. |
| Unable to care for self; requires equivalent of institutional or hospital care; disease may be progressing rapidly. | 440 | Disabled; requires special care and assistance |
| | 330 | Severely disabled; hospital admission is indicated although death not imminent. |

-continued

| | |
|---|---|
| 220 | Very sick; hospital admission necessary; active supportive treatment necessary. |
| 110 | Moribund; fatal processes progressing rapidly. |
| 0 | Dead |

Polyneuropathy Disability Score (PND Score)

| Stage | Description |
|---|---|
| 0 | No symptoms |
| I | Sensory disturbances but preserved walking capability |
| II | Impaired walking capacity but ability to walk without a stick or crutches |
| IIIA | Walking with the help of one stick or crutch. |
| IIIB | Walking with the help of two sticks or crutches. |
| IV | Confined to a wheelchair or bedridden. |

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

```
SEQUENCES

<210> SEQ ID NO: 1
<211> LENGTH: 127
<212> TYPE: PRT
<213> ORGANISM: Homo sapiens
Yoshikazu et al. J Biol. Chem. (1974)
249(21): 6796-805
<400> SEQUENCE: 1
GPTGTGESKCPLMVKVLDAVRGSPA                25

INVAVHVFRKAADDTWEPFASGKTS                50

ESGELHGLTTEEEFVEGIYKVEIDT                75

KSYWKALGISPFHEHAEVVFTANDS                100

GPRRYTIAALLSPYSYSTTAVVTNP                125

KE                                       127
```

```
SEQUENCE LISTING

<160> NUMBER OF SEQ ID NOS: 1

<210> SEQ ID NO 1
<211> LENGTH: 127
<212> TYPE: PRT
<213> ORGANISM: Homo sapiens

<400> SEQUENCE: 1

Gly Pro Thr Gly Thr Gly Glu Ser Lys Cys Pro Leu Met Val Lys Val
1               5                   10                  15

Leu Asp Ala Val Arg Gly Ser Pro Ala Ile Asn Val Ala Val His Val
            20                  25                  30

Phe Arg Lys Ala Ala Asp Asp Thr Trp Glu Pro Phe Ala Ser Gly Lys
        35                  40                  45

Thr Ser Glu Ser Gly Glu Leu His Gly Leu Thr Thr Glu Glu Glu Phe
    50                  55                  60

Val Glu Gly Ile Tyr Lys Val Glu Ile Asp Thr Lys Ser Tyr Trp Lys
65                  70                  75                  80

Ala Leu Gly Ile Ser Pro Phe His Glu His Ala Glu Val Val Phe Thr
                85                  90                  95

Ala Asn Asp Ser Gly Pro Arg Arg Tyr Thr Ile Ala Ala Leu Leu Ser
            100                 105                 110

Pro Tyr Ser Tyr Ser Thr Thr Ala Val Val Thr Asn Pro Lys Glu
        115                 120                 125
```

What is claimed is:

1. A method of treating transthyretin amyloidosis (ATTR) cardiomyopathy in a subject in need thereof, the method comprising orally administering to a subject in need thereof a total daily dosage of about 1,600 milligrams (mg) of Compound 1 in HCl salt form or an equivalent amount of Compound 1 in freebase or in a different salt form, wherein Compound 1 has the Formula:

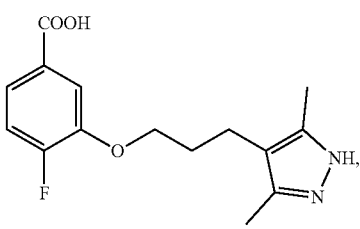 [SMILES: Cc1n[nH]c(C)c1CCCOc1cc(C(=O)O)ccc1F]

(Compound 1)

wherein Compound 1 in HCl salt form or an equivalent amount of Compound 1 in freebase or in a different salt form is administered twice daily.

2. The method of claim 1, wherein administration of Compound 1 in HCl salt form or an equivalent amount of Compound 1 in freebase or in a different salt form improves and/or reduces the decline in a six-minute walk test compared to subjects who did not receive treatment with Compound 1 in HCl salt form or an equivalent amount of Compound 1 in freebase or in a different salt form.

3. The method of claim 1, wherein the subject maintains about the same six minute walking distance as prior to treatment with Compound 1 in HCl salt form or an equivalent amount of Compound 1 in freebase or in a different salt form.

4. The method of claim 1, wherein the ATTR cardiomyopathy is wild-type ATTR cardiomyopathy (ATTRwt-CM).

5. The method of claim 1, wherein the ATTR cardiomyopathy is variant ATTR cardiomyopathy (ATTRv-CM).

6. The method of claim 5, wherein the ATTRv-CM is characterized by a transthyretin (TTR) protein that comprises a valine to isoleucine mutation at position 122 (V122I).

7. The method of claim 5, wherein the ATTRv-CM is characterized by a transthyretin (TTR) protein that comprises a threonine to proline mutation at position 49 (T49P), a valine to methionine mutation at position 30 (V30M), a threonine to alanine mutation at position 60 (T60A), a proline to serine mutation at position 24 (P24S), an aspartic acid to alanine mutation at position 38 (D38A), or a leucine to histidine mutation at position 58 (L58H).

8. A method of slowing the progression of transthyretin amyloidosis (ATTR) cardiomyopathy in a subject in need thereof, the method comprising orally administering to a subject in need thereof a total daily dosage of about 1,600 milligrams (mg) of Compound 1 in HCl salt form or an equivalent amount of Compound 1 in freebase or in a different salt form, wherein Compound 1 has the Formula:

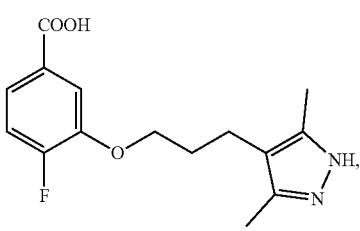

(Compound 1)

wherein Compound 1 in HCl salt form or an equivalent amount of Compound 1 in freebase or in a different salt form is administered twice daily.

9. The method of claim 1, wherein the administration of Compound 1 in HCl salt form or an equivalent amount of Compound 1 in freebase or in a different salt form decreases the frequency of cardiovascular-related hospitalizations as compared to subjects who did not receive treatment with Compound 1 in HCl salt form or an equivalent amount of Compound 1 in freebase or in a different salt form.

10. The method of claim 1, wherein the administration of Compound 1 in HCl salt form or an equivalent amount of Compound 1 in freebase or in a different salt form decreases mortality as compared to subjects who did not receive treatment with Compound 1 in HCl salt form or an equivalent amount of Compound 1 in freebase or in a different salt form.

11. The method of claim 10, wherein mortality is reduced by about 6% as compared to subjects who did not receive treatment with Compound 1 in HCl salt form or an equivalent amount of Compound 1 in freebase or in a different salt form after 30 months of administration.

12. The method of claim 10, wherein mortality is reduced by about 10% as compared to subjects who did not receive treatment with Compound 1 in HCl salt form or an equivalent amount of Compound 1 in freebase or in a different salt form after 30 months of administration.

13. The method of claim 10, wherein mortality is reduced by about 24% as compared to subjects who did not receive treatment with Compound 1 in HCl salt form or an equivalent amount of Compound 1 in freebase or in a different salt form after 30 months of administration.

14. The method of claim 10, wherein Compound 1 in HCl salt form or an equivalent amount of Compound 1 in freebase or in a different salt form is in HCl salt form.

15. The method of claim 1, wherein the administration of Compound 1 in HCl salt form or an equivalent amount of Compound 1 in freebase or in a different salt form increases transthyretin (TTR) blood serum concentration relative to a baseline level.

16. The method of claim 1, wherein the administration of Compound 1 in HCl salt form or an equivalent amount of Compound 1 in freebase or in a different salt form increases transthyretin (TTR) blood serum concentration by at least 10% relative to a baseline level after 28 days of treatment.

17. The method of claim 1, wherein the administration of Compound 1 in HCl salt form or an equivalent amount of Compound 1 in freebase or in a different salt form decreases serum blood levels of N-terminal pro-brain natriuretic peptide (N-terminal pro-BNP).

18. The method of claim 17, wherein serum blood levels of N-terminal pro-BNP of the subject decreases at least 10% after 30 months of administration as compared to a baseline level of N-terminal pro-BNP in the subject prior to treatment with Compound 1 in HCl salt form or an equivalent amount of Compound 1 in freebase or in a different salt form.

19. The method of claim 1, wherein the administration of Compound 1 in HCl salt form or an equivalent amount of Compound 1 in freebase or in a different salt form improves, stabilizes or delays worsening in the Kansas City Cardiomyopathy Questionnaire (KCCQ) classification of subjects.

20. The method of claim 19, wherein subjects have an average improvement of at least one level in the Kansas City Cardiomyopathy Questionnaire (KCCQ) classification of subjects.

* * * * *